US007611521B2

(12) United States Patent
Lubbers et al.

(10) Patent No.: US 7,611,521 B2
(45) Date of Patent: Nov. 3, 2009

(54) APPARATUS AND METHODS FOR TENDON OR LIGAMENT REPAIR

(75) Inventors: Lawrence M. Lubbers, Columbus, OH (US); Kenneth E. Hughes, Pataskala, OH (US); Carl R. Coleman, Powell, OH (US); Warren P. Williamson, IV, Loveland, OH (US); Craig B. Berky, Milford, OH (US); Thomas J. Ward, Columbus, OH (US); Matthew J. Huddleston, Backlick, OH (US); Mark A. Goldin, Orlando, FL (US); William J. Christy, Winter Park, FL (US); Perry DeFazio, Chicopee, MA (US); Brian Scott Schumacher, Orlando, FL (US); Terence Lee Murphy, Maitland, FL (US); Nickola Symone Lewis, Orlando, FL (US); Jeremy Jarrett, Cincinnati, OH (US); Joseph E. Young, Loveland, OH (US)

(73) Assignees: Tendon Technology, Ltd., Pataskala, OH (US); Ortheon Medical L.L.C., Orlando, FL (US)

( * ) Notice: Subject to any disclaimer, the term of this patent is extended or adjusted under 35 U.S.C. 154(b) by 707 days.

(21) Appl. No.: 10/816,725

(22) Filed: Apr. 2, 2004

(65) Prior Publication Data
US 2004/0193217 A1    Sep. 30, 2004

Related U.S. Application Data

(63) Continuation of application No. PCT/US02/31481, filed on Oct. 2, 2002, which is a continuation-in-part of application No. 09/969,947, filed on Oct. 3, 2001, now Pat. No. 6,984,241, which is a continuation-in-part of application No. PCT/US99/24098, filed on Oct. 18, 1999, which is a continuation-in-part of application No. 08/928,866, filed on Sep. 12, 1997, now Pat. No. 6,083,244.

(60) Provisional application No. 60/026,101, filed on Sep. 13, 1996, provisional application No. 60/043,086, filed on Apr. 8, 1997.

(51) Int. Cl.
*A61B 17/58* (2006.01)
*B25B 23/00* (2006.01)
(52) U.S. Cl. .................................. 606/104; 81/436
(58) Field of Classification Search ................. 606/104, 606/72, 73, 151, 232, 99; 227/67, 68; 81/436
See application file for complete search history

(56) References Cited

U.S. PATENT DOCUMENTS 2,075,508 A    3/1937    Davidson (Continued)

FOREIGN PATENT DOCUMENTS

DE           1810800          6/1970

(Continued)

OTHER PUBLICATIONS

L. Gordon et al., *Flexor Tendon Repair Using a Stainless Steel Internal Anchor*, Article, The Journal of Hand Surgery, vol. 23B N. 1, Feb. 1998.

*Primary Examiner*—Julian W Woo
(74) *Attorney, Agent, or Firm*—Wood, Herron & Evans, L.L.P.

(57) ABSTRACT

Apparatus and methods for repairing damaged tendons or ligaments. Various repair apparatus include an elongate tensile member and a pair of anchor assemblies connected for movement along the tensile member on either side of a repair site, such as a tear or laceration. The anchor assemblies or structures may take many forms, and may include barbed, helical, and crimp-type anchors. In the preferred embodiments, at least one anchor structure is movable along the elongate tensile member to assist with adjusting a tendon segment to an appropriate repair position and the anchor structure or structures are then lockable onto the elongate tensile member to assist with affixing the tendon at the repair position. Tendon and/or ligament-to-bone repair apparatus and methods employ similar concepts.

19 Claims, 37 Drawing Sheets

U.S. PATENT DOCUMENTS

| | | |
|---|---|---|
| 2,243,717 A * | 5/1941 | Moreira .................... 606/104 |
| 2,421,193 A | 5/1947 | Gardner .................... 128/335 |
| 2,472,009 A | 5/1949 | Gardner .................... 128/335 |
| 2,489,870 A | 11/1949 | Dzus .......................... 606/73 |
| 2,726,091 A * | 12/1955 | Topar .......................... 81/436 |
| 2,760,488 A | 8/1956 | Pierce |
| 3,123,077 A | 3/1964 | Alcamo ..................... 606/228 |
| 3,216,471 A * | 11/1965 | Wendel ....................... 81/436 |
| 3,489,143 A | 1/1970 | Halloran |
| 3,664,345 A | 5/1972 | Dabbs |
| 3,716,058 A | 2/1973 | Tanner, Jr. ................. 128/337 |
| 3,753,438 A | 8/1973 | Wood et al. |
| 4,430,998 A | 2/1984 | Harvey et al. ............... 128/335 |
| 4,535,772 A | 8/1985 | Sheehan |
| 4,537,185 A | 8/1985 | Stednitz |
| 4,549,545 A | 10/1985 | Levy .......................... 606/223 |
| 4,585,458 A | 4/1986 | Kurland .................... 623/13.17 |
| 4,590,928 A | 5/1986 | Hunt et al. |
| 4,592,346 A | 6/1986 | Jurgutis ....................... 128/92 |
| 4,637,380 A | 1/1987 | Orejola ...................... 128/334 |
| 4,643,178 A | 2/1987 | Nastari et al. |
| 4,723,548 A | 2/1988 | Lalonde .................... 128/335 |
| 4,741,330 A | 5/1988 | Hayhurst |
| 4,750,492 A | 6/1988 | Jacobs ....................... 606/230 |
| 4,796,612 A | 1/1989 | Reese |
| 4,832,026 A | 5/1989 | Jones |
| 4,834,752 A | 5/1989 | Van Kampen |
| 4,870,957 A | 10/1989 | Goble et al. ................. 128/92 |
| 4,873,976 A | 10/1989 | Schreiber ................... 128/334 |
| 4,901,721 A | 2/1990 | Hakki ........................ 606/103 |
| 4,927,421 A | 5/1990 | Goble et al. |
| 4,946,462 A | 8/1990 | Watanabe |
| 4,950,270 A | 8/1990 | Bowman et al. |
| 4,955,910 A | 9/1990 | Bolesky .................... 623/13.13 |
| 4,978,347 A | 12/1990 | Ilizaroy |
| 4,979,956 A | 12/1990 | Silvestrini ................... 623/13 |
| 4,988,351 A | 1/1991 | Paulos et al. ............... 606/72 |
| 5,006,023 A | 4/1991 | Kaplan ...................... 411/17 |
| 5,013,316 A | 5/1991 | Goble et al. |
| 5,041,129 A | 8/1991 | Hayhurst et al. ............ 606/232 |
| 5,053,047 A | 10/1991 | Yoon .......................... 606/223 |
| 5,061,283 A | 10/1991 | Silvestrini .................. 623/13 |
| 5,084,050 A | 1/1992 | Draenert .................... 606/77 |
| 5,123,914 A | 6/1992 | Cope |
| 5,152,765 A * | 10/1992 | Ross et al. .................. 606/99 |
| 5,156,616 A | 10/1992 | Meadows et al. |
| 5,236,431 A | 8/1993 | Gogolewski et al. |
| 5,254,127 A | 10/1993 | Wholey et al. |
| 5,258,015 A | 11/1993 | Li et al. |
| 5,263,973 A | 11/1993 | Cook |
| 5,269,290 A | 12/1993 | Barrett et al. ................. 128/4 |
| 5,269,809 A | 12/1993 | Hayhurst et al. |
| 5,306,290 A | 4/1994 | Martins et al. |
| 5,309,927 A | 5/1994 | Welch ........................ 128/898 |
| 5,342,376 A | 8/1994 | Ruff |
| 5,354,305 A | 10/1994 | Lewis et al. ................. 606/152 |
| 5,380,334 A | 1/1995 | Torrie et al. ................. 606/104 |
| 5,383,897 A | 1/1995 | Wholey ....................... 606/213 |
| 5,395,374 A | 3/1995 | Miller et al. |
| 5,411,523 A | 5/1995 | Goble ......................... 606/232 |
| 5,417,699 A | 5/1995 | Klein et al. .................. 606/139 |
| 5,425,747 A | 6/1995 | Brotz ......................... 606/228 |
| 5,426,843 A | 6/1995 | Bartky ........................ 29/516 |
| 5,433,607 A | 7/1995 | Schmid et al. ............... 433/173 |
| 5,464,424 A | 11/1995 | O'Donnell, Jr. ............. 606/228 |
| 5,472,452 A | 12/1995 | Trott .......................... 606/232 |
| 5,480,403 A | 1/1996 | Lee et al. .................... 606/72 |
| 5,486,197 A | 1/1996 | Le et al. ..................... 606/232 |
| 5,500,000 A | 3/1996 | Feagin et al. |
| 5,505,735 A | 4/1996 | Li .............................. 606/72 |
| 5,507,775 A | 4/1996 | Ger et al. .................... 606/216 |
| 5,520,691 A | 5/1996 | Branch |
| 5,520,700 A | 5/1996 | Beyar et al. ................. 606/139 |
| 5,527,342 A | 6/1996 | Pietrzak et al. .............. 606/232 |
| 5,531,232 A | 7/1996 | Hill ............................ 128/898 |
| 5,531,761 A | 7/1996 | Yoon .......................... 606/223 |
| 5,531,790 A | 7/1996 | Frechet et al. ............... 623/15 |
| 5,536,270 A | 7/1996 | Songer et al. |
| 5,556,428 A | 9/1996 | Shah .......................... 623/13 |
| 5,562,689 A | 10/1996 | Green et al. ................. 606/151 |
| 5,571,139 A | 11/1996 | Jenkins, Jr. |
| 5,582,616 A | 12/1996 | Bolduc et al. ............... 606/143 |
| 5,584,859 A | 12/1996 | Brotz ......................... 606/228 |
| 5,593,425 A | 1/1997 | Bonutti et al. ............... 606/232 |
| 5,601,557 A | 2/1997 | Hayhurst ..................... 606/72 |
| 5,626,613 A | 5/1997 | Schmieding |
| 5,643,289 A | 7/1997 | Sauer et al. .................. 606/139 |
| 5,643,320 A | 7/1997 | Lower et al. ................. 606/232 |
| 5,662,714 A | 9/1997 | Charvin et al. .............. 623/15 |
| 5,669,917 A | 9/1997 | Sauer et al. .................. 606/139 |
| 5,681,352 A | 10/1997 | Clancy, III et al. .......... 606/232 |
| 5,683,417 A | 11/1997 | Cooper |
| 5,690,632 A | 11/1997 | Schwartz et al. ............. 606/73 |
| 5,693,046 A | 12/1997 | Songer et al. |
| 5,702,397 A | 12/1997 | Goble et al. |
| 5,707,394 A | 1/1998 | Miller et al. ................. 606/232 |
| 5,707,395 A | 1/1998 | Li .............................. 606/232 |
| 5,720,765 A | 2/1998 | Thal |
| 5,723,008 A | 3/1998 | Gordon ....................... 623/13 |
| 5,723,009 A | 3/1998 | Frechet et al. ............... 623/15 |
| 5,728,135 A | 3/1998 | Bregen et al. ................ 606/228 |
| 5,728,136 A | 3/1998 | Thal ........................... 606/232 |
| 5,741,260 A | 4/1998 | Songer et al. |
| 5,755,065 A | 5/1998 | Sorkin ........................ 52/223.13 |
| 5,772,668 A | 6/1998 | Summers et al. ............. 623/1.11 |
| 5,782,844 A | 7/1998 | Yoon et al. .................. 606/139 |
| 5,797,913 A | 8/1998 | Dambreville et al. ......... 606/72 |
| 5,800,544 A | 9/1998 | Demopulos et al. .......... 623/13 |
| 5,810,851 A | 9/1998 | Yoon .......................... 606/148 |
| 5,824,008 A | 10/1998 | Bolduc et al. ............... 606/43 |
| 5,891,168 A | 4/1999 | Thal ........................... 606/232 |
| 5,897,591 A | 4/1999 | Kobayashi .................. 623/13.11 |
| 5,916,224 A | 6/1999 | Esplin ........................ 606/151 |
| RE36,289 E | 8/1999 | Le et al. ..................... 606/232 |
| 5,951,590 A | 9/1999 | Goldfarb .................... 606/232 |
| 5,954,747 A | 9/1999 | Clark ......................... 606/216 |
| 5,957,953 A | 9/1999 | DiPolo et al. ............... 606/232 |
| 5,964,772 A | 10/1999 | Bolduc et al. ............... 606/142 |
| 5,972,001 A | 10/1999 | Yoon .......................... 606/139 |
| 5,980,557 A | 11/1999 | Iserin et al. .................. 606/220 |
| 6,074,409 A | 6/2000 | Goldfarb .................... 606/232 |
| 6,083,244 A | 7/2000 | Lubbers et al. .............. 606/232 |
| 6,102,947 A | 8/2000 | Gordon ....................... 623/13.11 |
| 6,106,556 A | 8/2000 | Demopulos et al. .......... 623/13.16 |
| 6,129,762 A | 10/2000 | Li .............................. 623/13.11 |
| 6,132,442 A | 10/2000 | Ferragamo et al. .......... 606/151 |
| 6,149,669 A | 11/2000 | Li .............................. 606/232 |
| 6,168,596 B1 | 1/2001 | Wellisz et al. ............... 606/69 |
| 6,190,401 B1 | 2/2001 | Green et al. |
| 6,241,747 B1 | 6/2001 | Ruff |
| 6,296,656 B1 | 10/2001 | Bolduc et al. ............... 606/213 |
| 6,306,159 B1 | 10/2001 | Schwartz et al. ............. 606/232 |
| 6,319,257 B1 * | 11/2001 | Carignan et al. ............. 606/99 |
| 6,368,326 B1 | 4/2002 | Dakin et al. |
| 6,395,010 B1 | 5/2002 | Wotton, III |
| 6,485,503 B2 | 11/2002 | Jacobs et al. ................ 606/215 |
| 6,666,877 B2 | 12/2003 | Morgan et al. |
| 2001/0044637 A1 | 11/2001 | Jacobs et al. |
| 2002/0029063 A1 | 3/2002 | Wittmann |
| 2002/0173807 A1 | 11/2002 | Jacobs |

FOREIGN PATENT DOCUMENTS

| | | |
|---|---|---|
| DE | 3227984 A1 | 2/1984 |
| DE | 19840881 | 3/2000 |
| EP | 0092334 | 10/1983 |
| EP | 0478949 A1 | 4/1992 |
| EP | 0535802 | 4/1993 |
| GB | 2164562 | 3/1986 |
| WO | WO 97-07744 | 3/1997 |
| WO | WO 00/49983 | 8/2000 |

OTHER PUBLICATIONS

L. Gordon et al., *Flexor Tendon Repair Using a Stainless Steel External Splint*, Article, Journal of Hand Surgery, vol. 24B, No. 6, Dec. 1999.

U.S. Patent and Trademark Office, Office Action in U.S. Appl. No. 10/620,932, Jun. 1, 2009.

U.S. Patent and Trademark Office, Office Action in U.S. Appl. No. 10/620,932, Apr. 3, 2007.

US 6,447,535, 09/2002, Jacobs et al. (withdrawn)

* cited by examiner

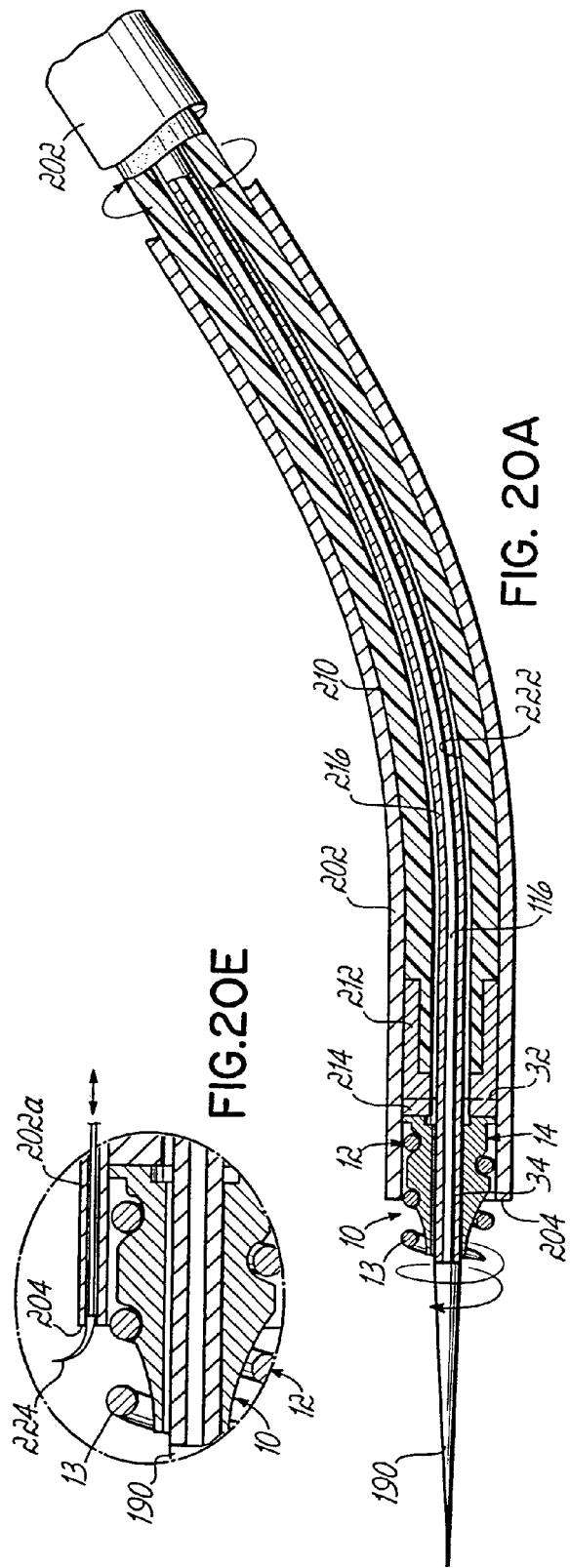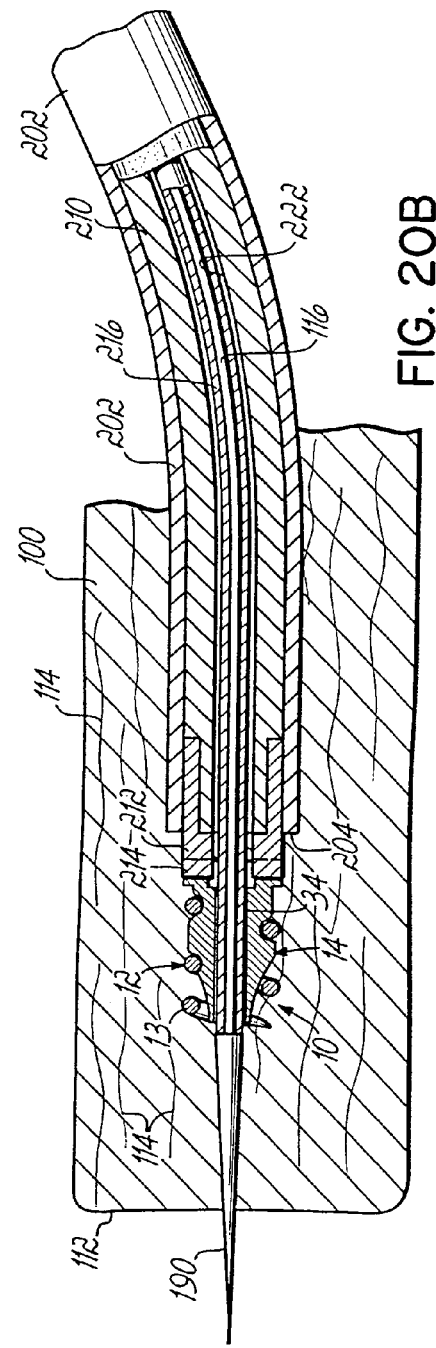

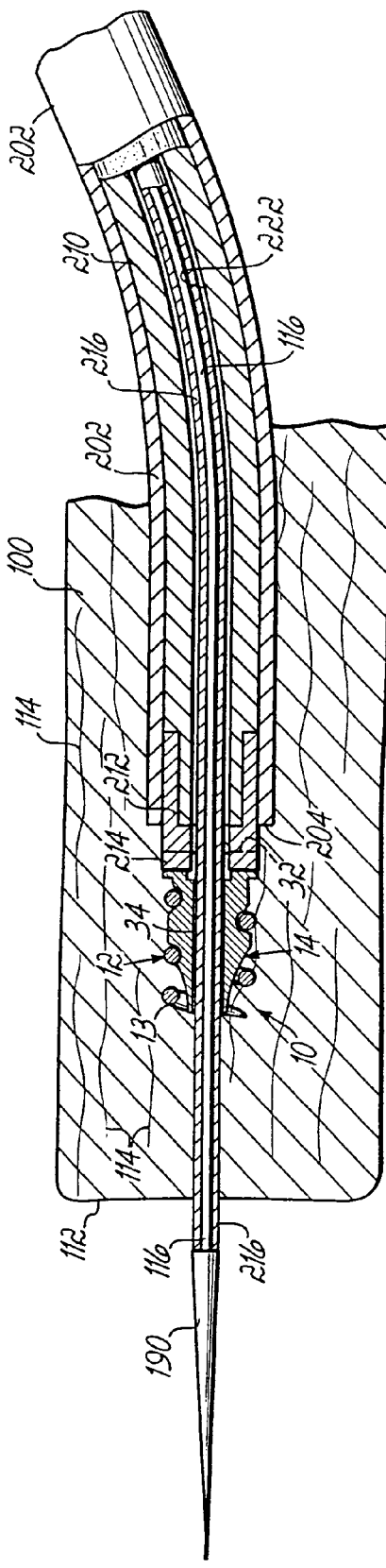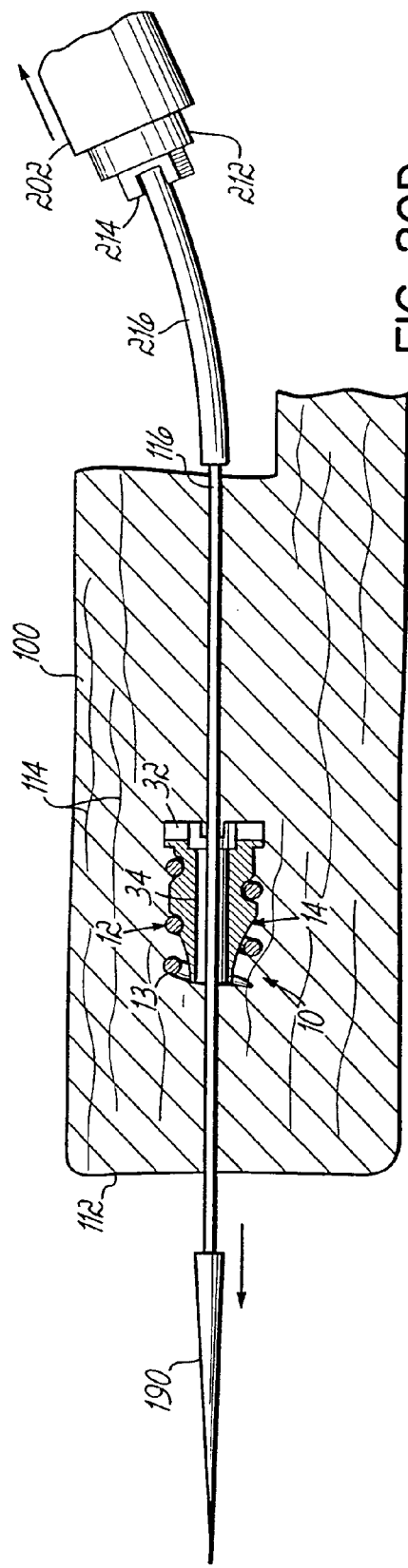
FIG. 20C
FIG. 20D

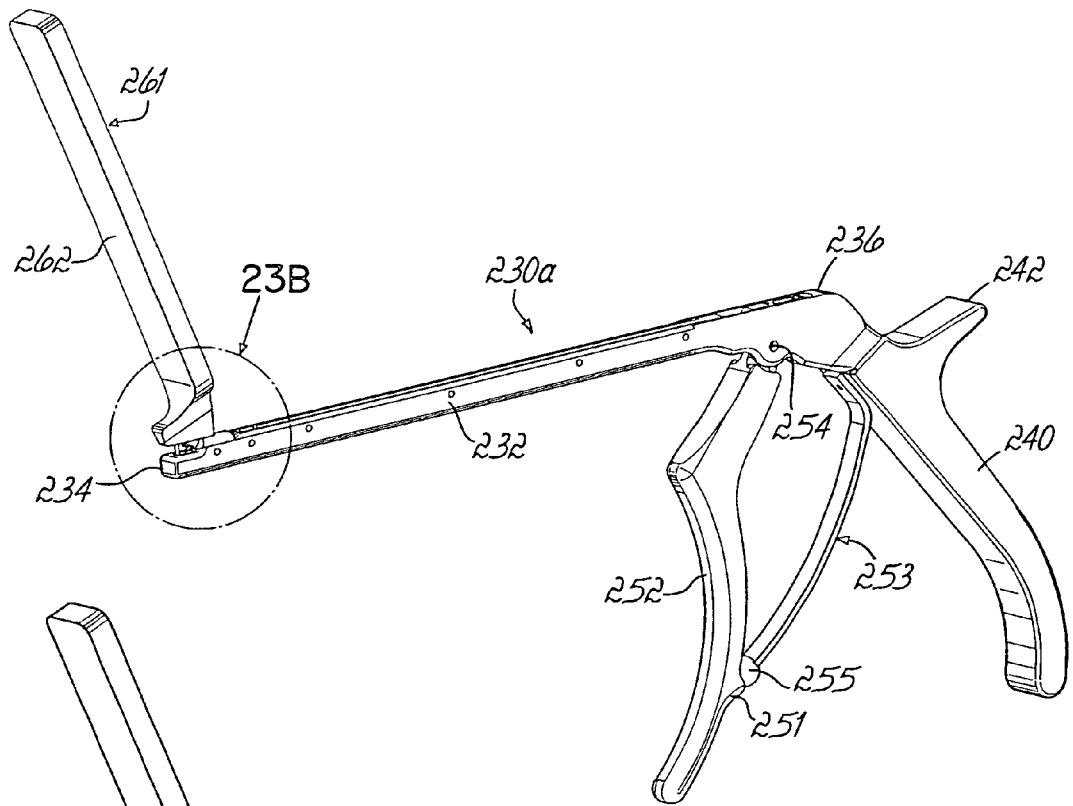
FIG. 23A
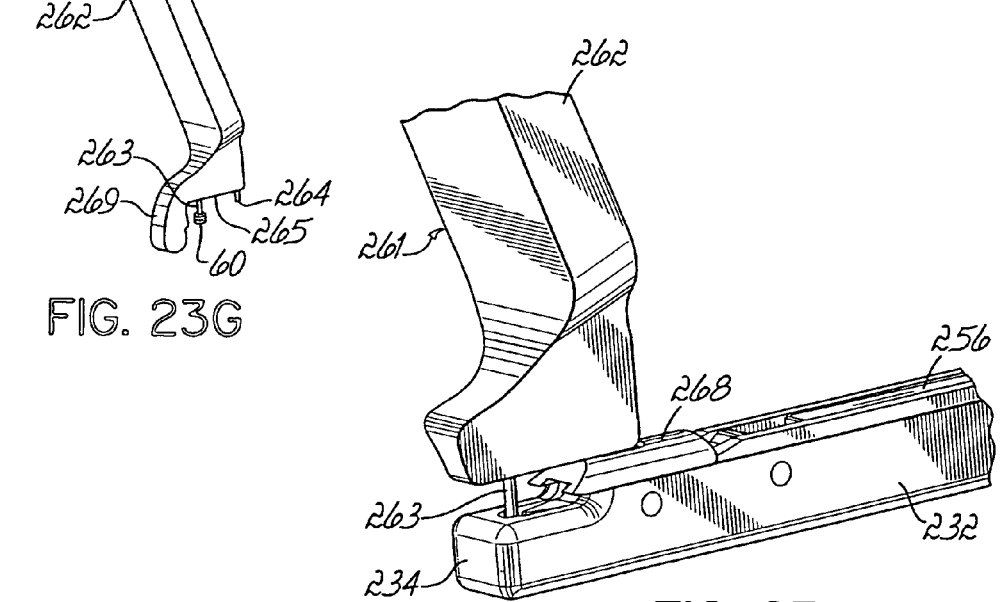
FIG. 23G
FIG. 23B

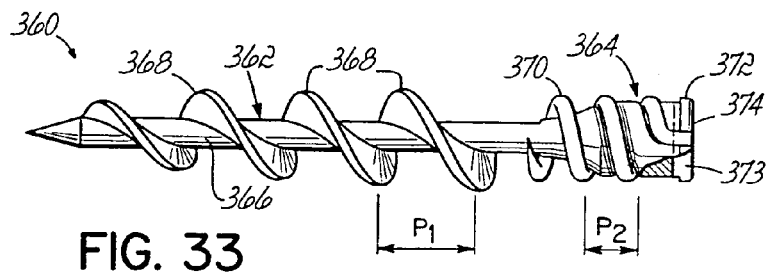
FIG. 33
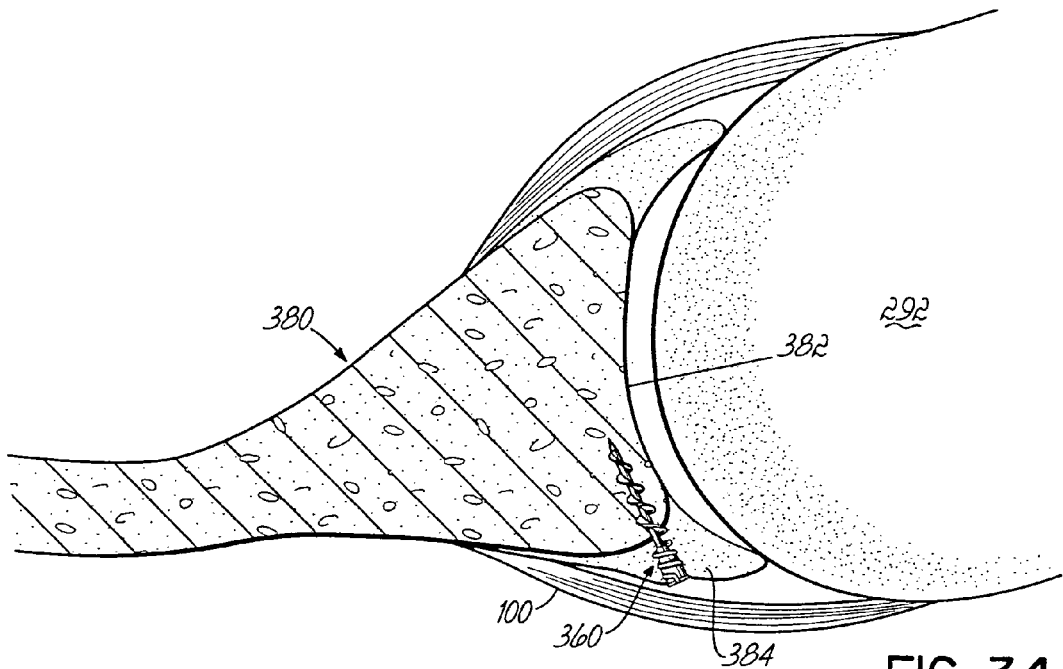
FIG. 34
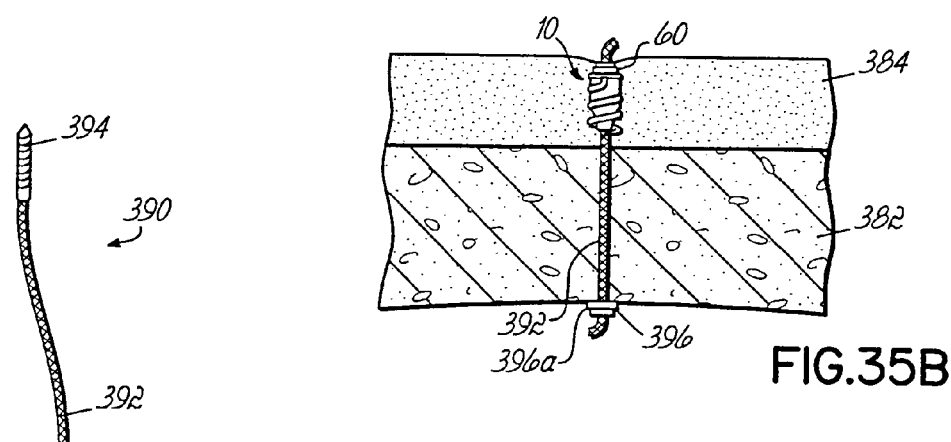
FIG. 35A
FIG. 35B
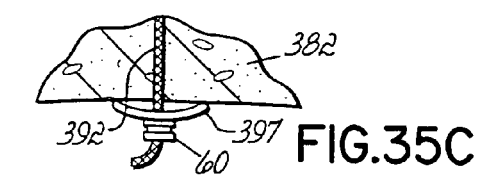
FIG. 35C

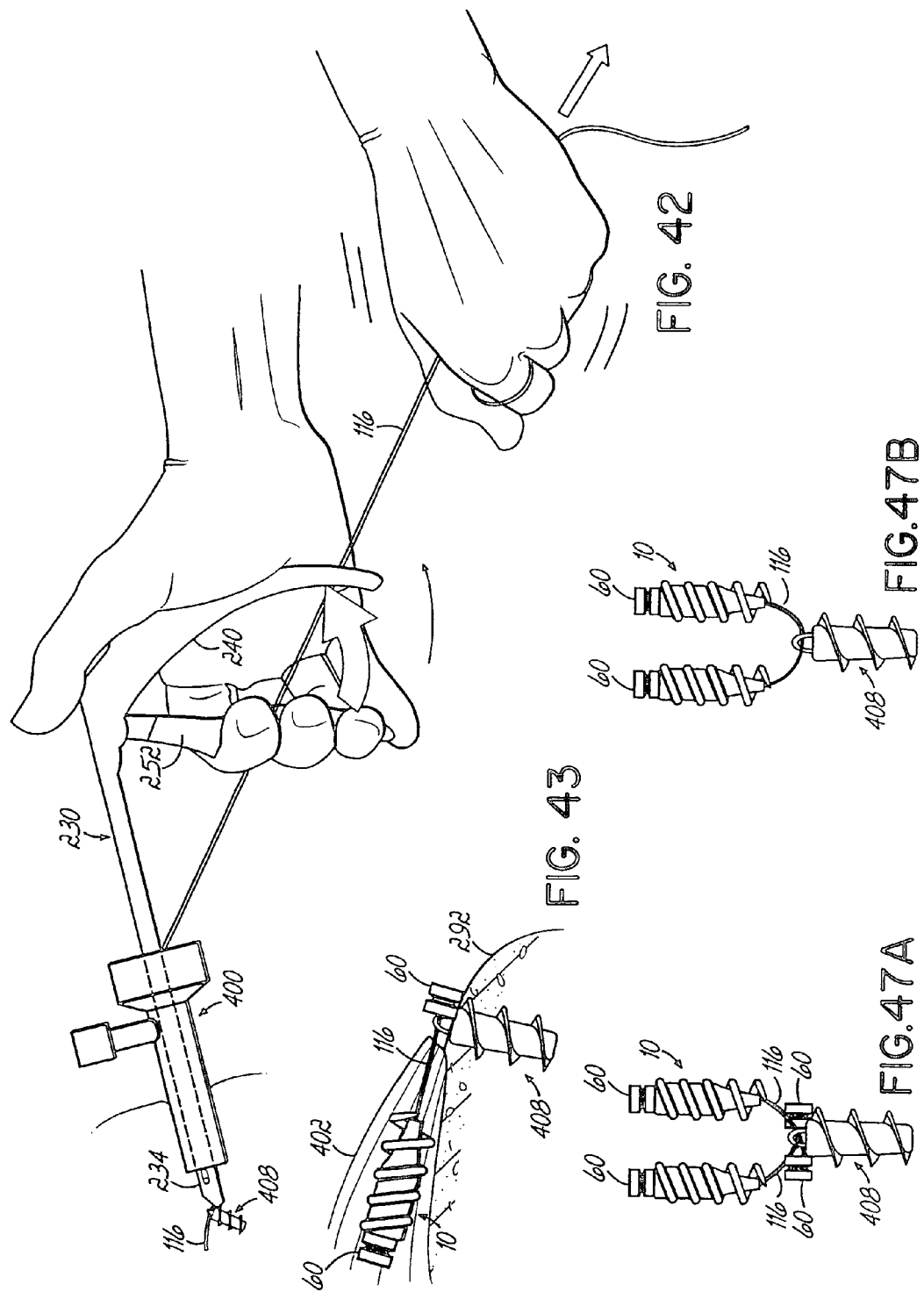

APPARATUS AND METHODS FOR TENDON OR LIGAMENT REPAIR

The present application is a continuation of PCT Serial No. PCT/US02/31481 filed on Oct. 2, 2002, now pending, which is a continuation-in-part of U.S. application Ser. No. 09/969,947, filed on Oct. 3, 2001, now U.S. Pat. No. 6,984,241, which is a continuation-in-part of PCT Serial No. PCT/US99/24098 filed on Oct. 18, 1999, now expired, which is a continuation-in-part of U.S. Ser. No. 08/928,866, filed on Sep. 12, 1997, now U.S. Pat. No. 6,083,244, which is based on provisional patent application Ser. No. 60/026,101, filed Sep. 13, 1996, now abandoned, and provisional patent application Ser. No. 60/043,086, filed on Apr. 8, 1997, now abandoned. The disclosures of each of these prior related applications are hereby fully incorporated by reference herein.

FIELD OF THE INVENTION

The present invention generally relates to tendon or ligament repair apparatus and methods. More specifically, the invention relates to the repair of severed or otherwise damaged tendons or ligaments and the attachment of tendons or ligaments to bone. As used in the specification and claims, the terms "tendon" and "ligament" are used in an interchangeable manner.

BACKGROUND OF THE INVENTION

The repair of tendons or ligaments is a challenging and complication-prone area of surgery. Over the past 40 years, improvements in the art of tendon and ligament repair have focused primarily on suture techniques used to repair tendons and ligaments. Tendons can sustain high tensile forces resulting from muscle contraction, yet are flexible enough to bend around bony surfaces and deflect beneath retinacula to change the final direction of muscle pull. Tendons attach muscle to bone and transmit tensile loads from muscle to bone, thereby producing joint movement. Ligaments attach bone to bone and can flex to allow natural movement of the bones that they attach, but are strong and inextensible so as to offer suitable resistance to applied forces. Ligaments augment the mechanical stability of the joints.

Bundles of collagen fibers embedded in a connecting matrix, known as ground substance, provide the load carrying elements of natural tendons and ligaments. The tensile strength of tendons and ligaments is provided by the lengthwise parallel collagen fibers, which give them the ability to withstand high tensile loads. The arrangement of collagen fibers is nearly parallel in tendons, equipping them to withstand high unidirectional loads. The less parallel arrangement of the collagen fibers in ligaments allows these structures to sustain predominant tensile stresses in one direction and smaller stresses in other directions. The ground substance in both tendons and ligaments acts generally as a cementing matrix to hold the collagen fibers together.

Today, the most common methods of repairing torn, severed or otherwise damaged tendons involve approximating the severed ends of the tendons and suturing one side of the tendon to the other, thereby returning the tendon to its natural position. Most suture methods employ an internal suture with external knots distal and proximal to the laceration, or within the laceration. Most sutures typically include a continuous running external suture at the junction of the repair, known as an epitendinous suture, to approximate the tendon ends. Other methods of repairing a damaged tendon involve the placement of prosthetic material either within or around the tendon. Whether prosthetics are used or the repair is done using only sutures, both methods involve external sutures or knots which have the disadvantage of creating sites for the development of adhesions, the growth of cells around the foreign material, as a result of the body's natural healing process. The development of adhesions and the external foreign material promote increased work of flexion of the repaired tendons and ligaments. Increased risk of adhesions and increased work of flexion is exacerbated when the number of suture strands increases, or the amount of suture material or prosthetic material is increased, as is commonly done to affect a stronger repair.

The effectiveness of sutures depends upon many factors, including the techniques used to create the sutures. These techniques are difficult to master and very tedious to perform. The use of internal or external prosthetic splints also pose increased risk for the development of adhesions, and large slits that are created for the insertion of splints within the tendons create risk of structural damage to the internal blood supply, which may cause tissue degeneration.

Another problem of conventional tendon repair methods relates to the softening of the damaged tendon ends, which begins shortly after the damage or injury occurs and continues for approximately 12 days. This softening results in a weakening of the tendon fibers, which may contribute to the formation of a gap at the repair site during the early phases of tendon healing. It is believed that gaps form at the repair site due to a loss of purchase by the grasping portion of the suture at the tendon-suture interface. The grasping suture may even completely tear out, resulting in a failure of repair called "rake out."

The ideal repair for a tendon or ligament is one which exhibits high strength, high flexibility, and the ability to join the ends of the tendon or ligament without any foreign material on the outside surface of the tendon or ligament. Current and past tendon or ligament repair techniques have concentrated on increasing the tensile strength of the repair by adding more structural components to the repair (for example, sleeves, splints, additional suture strands, additional knots). All of these techniques trade off between early tensile strength at the repair site and increased work of flexion and increased risk of adhesions or other problems. None of these techniques have utilized the physiological make up of the tendon to provide a stronger repair.

The attachment of tendons, ligaments, and other soft tissue to bone, such as in arthroscopic shoulder stabilization or rotator cuff repair, presents problems similar to those experienced in intra-tendon or intra-ligament repair. In this regard, simply suturing soft tissue to a bone anchor or using external soft tissue anchor members may not provide the necessary strength of repair. These techniques also promote the formation of adhesions on tendons ligaments, and other soft tissue and increase the work of flexion of the tendons and ligaments, as discussed above.

Finally, retrieval of soft tissue has also been a problematic area of repair surgery. Typically, a surgeon must use a small grasping tool with thin, movable jaws similar to needle-nose pliers to grasp the end of the soft tissue and pull and transfix it in an appropriate operating position. Unfortunately, gripping soft tissue in this manner often damages the tissue and makes the tissue less able to hold the epitendinous suture. These damaged ends will also form scar tissue or adhesions which further adversely affect the repair.

There is thus a need for tendon repair techniques and apparatus that utilize harness the intrinsic strength of soft tissue fibers, but allow the tendon to flex while moving. These repair apparatus should resist any gapping or rupture during immediate post-operative physical therapy, and reside in the interior of the soft tissue to reduce or possibly eliminate post-operative adhesions. The repair apparatus should also produce low work of flexion while gliding unhindered through the tendon sheaths. There is generally a need for soft tissue repair apparatus and methods that allow the patient to immediately begin active physical therapy without risking any tendon repair failure while minimizing or eliminating the need for sutures or other repair structure on the external surfaces of the soft tissue, thereby reducing the formation of adhesions. There is a further need for soft tissue-to-bone repair techniques and apparatus with at least some of these attributes. Finally, there is a need for a soft tissue retrieval device which also utilizes the inherent strength of the fibers and minimizes damage to the retrieved end of the soft tissue.

SUMMARY OF THE INVENTION

The present invention provides various apparatus and methods for repairing torn, or otherwise damaged, tendons, ligaments and other soft tissue wherein the inventive apparatus and methods overcome various drawbacks of the prior art. Although various aspects of this invention are discussed with respect to illustrative tendon and ligament repair, it will be appreciated that the invention is generally applicable to other soft tissue procedures as well.

In one aspect of the invention, a soft tissue anchor assembly has an anchor configured to be inserted within the interior of a tendon or ligament and a retaining member which is coupled to the anchor such that when the anchor and retaining member are driven into a tendon or ligament, the anchor assembly grasps and holds the fibers of the tendon or ligament between the anchor and the retaining member. In an exemplary embodiment, the anchor comprises one or more helical coils which may be driven into the interior of the tendon or ligament to gather fibers as it is rotated and translated into the tendon or ligament. The retaining member includes a slot for engaging a drive tool such that the retaining member and helical anchor may be simultaneously driven into a tendon or ligament with the drive tool.

In further accordance with the invention, the soft tissue anchor assembly is coupled to an elongate tensile member such as a flexible, multi-filament suture, and is secured to the elongate tensile member by a stop member to thereby fix the location of the elongate tensile member relative to the anchor assembly. The stop member may be secured to the elongate tensile member by various methods, such as crimping the stop member or by engagement of the stop member with a contoured surface of the elongate tensile member. Alternatively, the soft tissue anchor assembly itself may be constructed for securing the anchor assembly to an elongate tensile member.

In another aspect of the invention, a soft tissue anchor assembly includes a helical anchor and an expandable retaining member coupled to the helical anchor. The retaining member is expandable from a contracted state, wherein fibers of the tendon or ligament may be received between the retaining member and the helical anchor when the anchor assembly is driven into a tendon or ligament. The retaining member may then be expanded to compress the fibers of the tendon or ligament against the coils of the helical anchor to thereby secure the anchor assembly within the tendon or ligament.

In yet another aspect of the present invention, an exemplary soft tissue anchor assembly includes an anchor body having a bore extending through the body for coupling the anchor assembly to an elongate tensile member. The anchor assembly further includes a plurality of barbs which extend outward from the body and which are configured to grasp fibers of the tendon or ligament when the anchor assembly is driven into the tendon or ligament.

In accordance with the present invention, the various soft tissue anchors may be used with elongate tensile members to repair severed tendons or ligaments wherein one or more of the exemplary anchor assemblies are inserted into each of the segments of a severed tendon or ligament, elongate tensile members are coupled between anchor assemblies on respective segments of the tendon or ligament, and are secured to anchor assemblies on one of the segments. Tension is applied to the elongate tensile members to approximate the tendon or ligament segments and the remaining anchor assemblies are secured to the elongate tensile member to fix the position of the segments relative to one another. In one aspect, the soft tissue anchors may be inserted into a tendon or ligament through a longitudinal surface of the tendon or ligament. In another aspect, the soft tissue anchors may be inserted within a tendon or ligament through a severed end of a tendon or ligament.

In another aspect of the invention, various apparatus and methods for securing tendons or ligaments to bones are provided. In one exemplary method, the soft tissue anchors are used in conjunction with elongate tensile members to secure a tendon or ligament to a bone. According to this method, the surface of the bone is prepared, such as by abrading the surface or forming a trough within the surface, and holes are drilled through the bone. The soft tissue anchors are installed within the tendon or ligament and coupled to the elongate tensile members, as described above, and the elongate tensile members are routed through the holes in the bone. The elongate tensile members then may be tensioned to approximate the tendon or ligament to the bone and then secured to fix the location of the tendon or ligament. The elongate tensile members may be secured to the bone using, for example, washers secured to the ends of the elongate tensile members, or they may be looped through the holes back toward the tendon or ligament to be secured to the tendon or ligament by other soft tissue anchor assemblies, which have been installed within the tendon or ligament.

In yet another aspect of the invention, tendons or ligaments may be secured to a bone using a bone anchor. Various exemplary bone anchors are provided for securing tendons or ligaments in this manner. In one exemplary embodiment, a bone anchor includes an anchor body having a bore extending through the body for coupling the body with an elongate tensile member. The anchor further includes one or more projections which extend outwardly from the body to engage the bone. The bone anchor may be inserted within a hole which has been formed in the bone and the projections engage the bone to prevent removal of the anchor from the bone.

In another exemplary embodiment, the bone anchor includes a flared aperture at one end through which an elongate tensile member coupled to the anchor may extend for connection to a tendon or ligament. Advantageously, the flared aperture permits attachment of the tendon or ligament adjacent the bone anchor without exposing the elongate tensile member to sharp edges. In another exemplary embodiment, the bone anchor further includes a swivel member rotatably coupled to an end of the bone anchor. An elongate tensile member coupled with the bone anchor may extend through an aperture in the swivel member to secure a tendon or ligament adjacent the bone while preventing damage to the elongate tensile member. In yet another exemplary embodiment, the bone anchor includes means for securing an elongate tensile member directly to the bone anchor, such as by crimping onto the elongate tensile member or engaging a contoured surface of the elongate tensile member.

According to one exemplary method for securing a tendon or ligament to a bone, a bone anchor is attached to a bone and a soft tissue anchor is inserted within a tendon or ligament. The bone anchor and soft tissue anchor are coupled together by an elongate tensile member and tension is applied to the elongate tensile member to approximate the tendon or ligament to the bone.

In another aspect of the invention, there is provided an anchor for attaching a tendon, ligament or other soft tissue directly to a bone. The exemplary anchor includes a first portion that is configured to engage the bone, and a second portion that is configured to engage the soft tissue. The first portion includes an elongate shaft having screw threads, barbs, or other structure disposed along the length of the shaft for securing the anchor to the bone. The second portion includes a soft tissue anchor assembly having a helical anchor and a retaining member coupled to the helical anchor, whereby fibers of the soft tissue may be grasped and firmly held between the helical anchor and the retaining member, as described above. According to an exemplary method, the anchor may be used to secure a glenoid labrum to a glenoid socket, whereby the anchor is installed through the glenoid labrum such that the soft tissue anchor assembly becomes attached to and compresses the glenoid labrum and the first portion of the anchor is driven for attachment into the bone. In one embodiment, the first and second portions of the bone anchor are integrally formed. In another exemplary embodiment, the first and second portions are separate and may be coupled together prior to installation within the soft tissue, or they may be coupled together after the second portion has been inserted within the soft tissue.

In yet another aspect of the invention, an exemplary apparatus for attaching a tendon or ligament to a bone includes an elongate tensile member having a first end configured to be driven through soft tissue and bone when the elongate tensile member is rotated about its longitudinal axis, a soft tissue anchor couplable to the elongate tensile member, and at least one stop member securable to the elongate tensile member to fix the position of the elongate tensile member relative to the soft tissue anchor. According to one exemplary method for using this apparatus, a glenoid labrum is attached to a glenoid socket by installing the elongate tensile member through the glenoid socket and glenoid labrum, the soft tissue anchor is inserted within the glenoid labrum, the elongate tensile member is coupled to the soft tissue anchor, and tension is applied to the elongate tensile member to approximate the glenoid labrum and glenoid socket. The opposite end of the elongate tensile member may be secured to the bone using a washer secured with a stop member.

The present invention also provides various tools for facilitating the repair of damaged tendons, ligaments, and other soft tissue using the exemplary soft tissue anchors, bone anchors, elongate tensile members, and stop members of the invention. In one aspect, a tool is provided for inserting a soft tissue anchor within a tendon or ligament. The tool includes a rotatable shaft carried within a tubular housing and a needle-shaped member fixed to one end of the shaft. A soft tissue anchor assembly may be installed within one end of the housing and over the needle-shaped member to engage a drive member located near the end of the shaft. In use, the tool may be positioned within an incision made in a tendon or ligament and the anchor assembly may be driven into the tendon or ligament by manipulating a knob on the tool to rotate and translate the anchor assembly into the tendon or ligament.

In another exemplary embodiment, a tool for inserting a soft tissue anchor within a tendon or ligament further includes a tubular inner member disposed within the shaft and having an inner channel sized to receive an elongate tensile member. The tubular inner member may be extended beyond the end of the housing to drive an elongate tensile member having a sharpened tip through the tendon or ligament after the soft tissue anchor has been inserted within the tendon or ligament.

Another exemplary tool of the invention is useful for crimping stop members onto elongate tensile members. The exemplary tool includes first and second jaws which are movable toward each other. The first jaw is configured to receive and hold a stop member and the second jaw is configured to collapse the crimp member when first and second handles of the tool are manipulated to move the first and second jaws together.

In yet another exemplary embodiment, a retrieval tool is provided for removing an anchor from within a tendon or ligament, as may be desired when the anchor is misinstalled. The retrieval tool includes a shaft having a handle portion at one end and a tool driver portion at the other end for engaging the soft tissue anchor. A needle-shaped member extending from the tool driver portion is configured to couple with a soft tissue anchor which has been installed in a tendon or ligament and the retrieval tool may be manipulated to rotate the soft tissue anchor in a direction which causes the soft tissue anchor to back out of the tendon or ligament.

In yet another exemplary embodiment, a tool for crimping a stop member and cutting an elongate tensile member is provided. The exemplary tool includes an elongate housing having a first end configured to receive a stop member and an elongate tensile member threaded through the stop member. The tool further includes a crimp bit and a cutting member movably disposed near the first end of the housing and configured to crimp the stop member and cut the elongate tensile member when an actuating lever is manipulated by the user.

In yet another exemplary embodiment, a loading tool is provided for loading stop members within the first end of the crimping-and-cutting tool. The loading tool includes a first pin which receives a stop member and a second pin which engages the spring-loaded crimp bit on the crimp-and-cut tool to move the crimp bit away from the crimping jaw whereafter the stop member may be positioned within the crimp jaw by the first pin.

In another aspect of the present invention, a method for repairing a rotator cuff is provided. According to the exemplary method, a soft tissue anchor is installed within a tendon of the rotator cuff, a bone anchor is installed within the head of the humerus bone, an elongate tensile member is coupled to the soft tissue anchor and to the bone anchor, tension is applied to the elongate tensile member to approximate the rotator cuff to the humerus, and stop members are secured to the elongate tensile member to fix the position of the elongate tensile member relative to the bone anchor and the soft tissue anchor.

These and other advantages, objectives and features of the invention will become more readily apparent to those of ordinary skill upon review of the following detailed description of illustrative embodiments of the invention.

BRIEF DESCRIPTION OF THE DRAWINGS

FIGS. 20A-20D are cross-sectional illustrations depicting operation of the tool of FIG. 19 to insert a soft tissue anchor into a tendon or ligament and to drive a tensile member through the tendon or ligament;

FIG. 20E is a partial cross-sectional view of the tool of FIG. 19, illustrating an alternative embodiment having extendable barbs;

FIG. 23A is a perspective view of an alternate embodiment of the tool of FIG. 21, further depicting an exemplary tool for loading a stop member onto the tool;

FIG. 23B is an enlarged perspective view of the end of the tool of FIG. 23A, illustrating the loading tool coupled to its end;

FIG. 23G is a perspective view of an alternate embodiment of the loading tool of FIG. 23A;

FIG. 33 is an elevational view of an exemplary anchor of the present invention, configured to attach a tendon or ligament directly to a bone;

FIG. 34 is a schematic illustration depicting an exemplary method of attaching a glenoid labrum to a glenoid socket using the anchor of FIG. 33;

FIG. 35A is an elevation view of an exemplary apparatus for attaching a glenoid labrum to a glenoid socket;

FIG. 35B-35C are schematic illustrations depiction various methods of using the apparatus of FIG. 35A to attach a glenoid labrum to a glenoid socket;

FIG. 42 is a schematic illustration depicting the use of the tool of FIG. 21 to approximate the rotator cuff tendon and secure a stop member, according to the exemplary method;

FIG. 43 is a schematic illustration depicting a rotator cuff tendon which has been approximated to a humerus bone according to the exemplary method;

FIGS. 47A-47B are schematic illustrations depiction other exemplary methods of securing a rotator cuff tendon to a bone anchor during a rotator cuff repair;

DETAILED DESCRIPTION OF THE PREFERRED EMBODIMENTS

Figure 1:
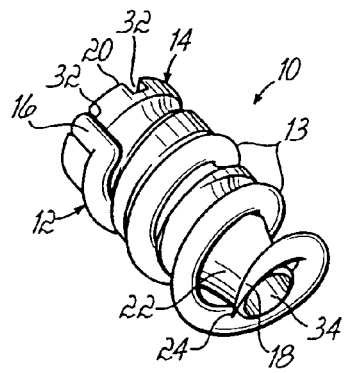
FIG. 1 is a perspective view of a unitary anchor assembly comprising a helical anchor coupled for insertion with a core portion, or tendon fiber-retaining member.
Figure 2:
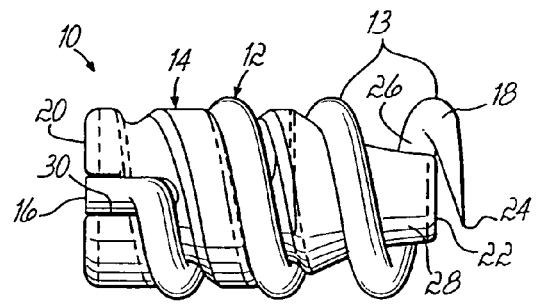
FIG. 2 is an elevational view of the unitary anchor assembly of FIG. 1, illustrating detail of the anchor assembly.

Referring now to FIGS. 1 and 2, an exemplary embodiment of the invention is described in connection with tendon-to-tendon or ligament-to-ligament repair. In this embodiment, a soft tissue anchor assembly 10 comprises a helical anchor 12 and a core portion or tendon fiber retaining member 14. Helical anchor 12 has proximal and distal ends 16, 18 and retaining member 14 likewise has proximal and distal ends 20, 22. The distal end 18 of helical anchor 12 extends distally beyond the distal end 22 of retaining member 14 and is sharpened to a point 24 to aid in insertion. In addition, retaining member 14 is tapered at its distal end 22 creating a space 26 between coils 13 of the helical anchor 12 and the outside surface 28 of the retaining member 14 for receiving and retaining tendon or ligament fibers therein, at least at a location near distal ends 18, 22 as will be discussed more fully below.

The proximal end 16 of helical anchor 12 is fixed to retaining member 14 at its proximal end 20. This may be accomplished in various ways, however, in the preferred embodiment, the proximal end 16 of helical anchor 12 is retained in a slot 30 that extends along a longitudinal axis of retaining member 14 and is welded such as through a laser or resistance welding operation. The proximal end 20 of retaining member 14 further includes a slot 32 for receiving an insertion tool and, if necessary, a removal tool to be described below. Retaining member 14 includes a central longitudinal bore 34 for receiving an elongate, preferably flexible, tensile member as will be described more fully below. The retaining member 14 may be secured to the tensile member by a crimpable stop member 60 provided as a separate member or it may be integral with retaining member 14, as described in copending application Ser. No. 09/969,947, or a different type of locking member may be used instead.

Figure 3:
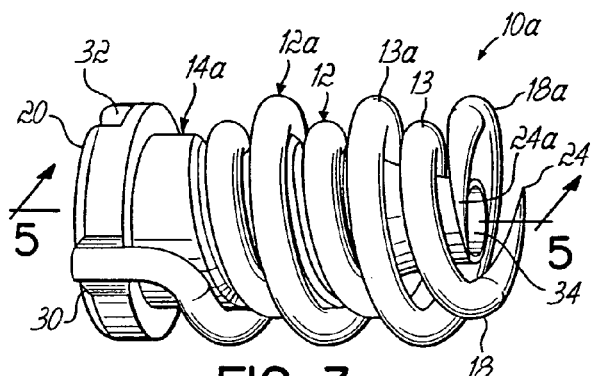
FIGS. 3-4 are perspective views of another exemplary anchor assembly of the present invention.
Figure 4:
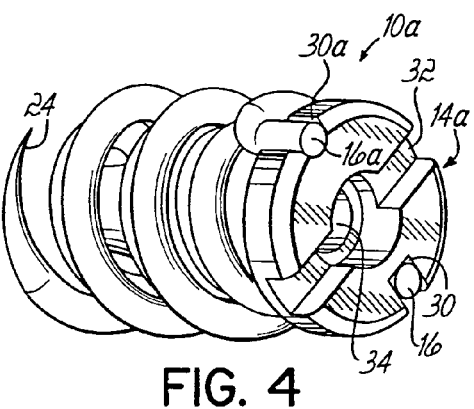
Figure 5:
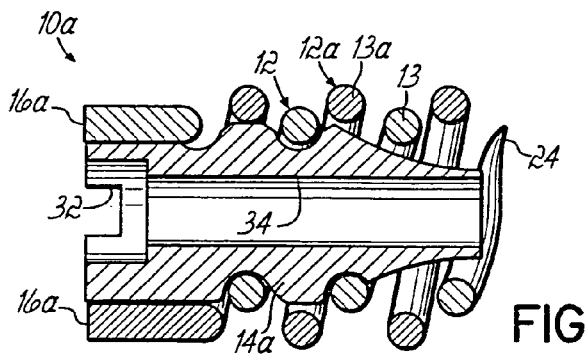
FIG. 5 is a cross-sectional view of the anchor assembly of FIGS. 3-4.

Referring to FIGS. 3-4, there is shown another exemplary soft tissue anchor assembly 10a of the present invention. Soft tissue anchor assembly 10a is similar to the assembly 10 of FIGS. 1 and 2 and similar components have been correspondingly numbered. The tissue anchor assembly 10a comprises first and second helical anchors 12, 12a coupled to a retaining member 14a. The helical anchors 12, 12a are arranged so that the coils 13a of the second helical anchor 12a are disposed between corresponding coils 13 of the first helical anchor 12, as best seen in FIGS. 3 and 5. As shown in FIG. 5, the second helical anchor 12a has a coil diameter which is greater than the coil diameter of the first helical anchor 12, however the helical anchors 12, 12a are otherwise similar. Proximal ends 16, 16a of the first and second helical anchors 12, 12a are secured to the retaining member 14a within slots 30, 30a at the proximal end 20 of the retaining member 14a, as best seen in FIG. 4.

Figure 6:
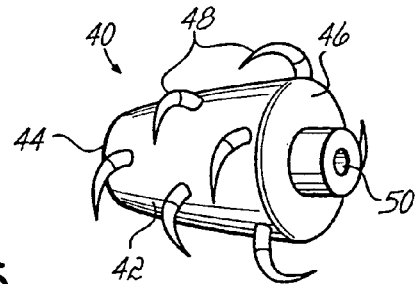
FIG. 6 is a perspective view of yet another exemplary anchor assembly of the present invention.

Another exemplary soft tissue anchor assembly 40 is shown in FIG. 6. The anchor assembly 40 includes an anchor body 42 having a first end 44 and second end 46. In the exemplary embodiment shown, the anchor body 42 tapers from the second end 46 toward the first end 44 to form a generally frustoconically-shaped section. Several barbs extend radially outward from the outer surface of the body and along a circumferential direction of the body so that when anchor assembly 40 is inserted into a tendon or ligament, rotation of the anchor assembly 40 within the tendon or ligament will cause the barbs 48 to engage the fibers of the tendon or ligament. The anchor assembly 40 further includes a central bore 50 extending longitudinally along the body 42 and between the first and second ends 44, 46. The central bore 50 is sized for coupling the anchor assembly 40 to an elongate tensile member, such as a flexible suture. In an exemplary embodiment, anchor assembly 40 is formed from an absorbable, or biodegradable, material, such as polylactide or any other suitable material, as is known in the art. While anchor assembly 40 is particularly suited to being formed from an absorbable material, it will be appreciated that any of the implantable devices described herein may be formed from such material.

Figure 7:
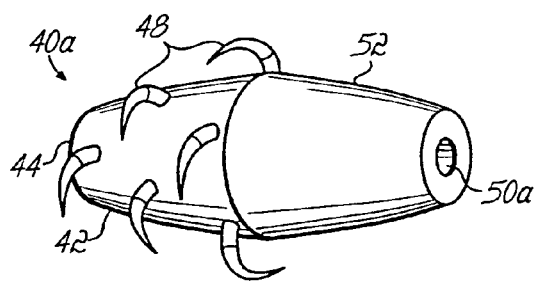
FIG. 7 is a perspective view of another exemplary anchor assembly, similar to the anchor assembly of FIG. 6.

With reference to FIG. 7, there is shown an exemplary anchor assembly 40a, similar to the anchor assembly 40 of FIG. 6. The anchor assembly 40a further includes a second body section 52 adjacent the second end 46 of the anchor body 42 and tapered in a direction opposite the first body section 42. A central bore 50a extends longitudinally through the second body section 52 and communicates with the bore 50 of anchor body 42 to provide a continuous passage by which the anchor assembly 40a may be coupled to an elongate tensile member.

Figure 8:
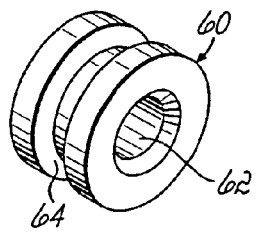
FIG. 8 is a perspective view of an exemplary stop member of the present invention.

In FIG. 8 there is shown an exemplary crimpable stop member 60 having a generally cylindrical shape and including a central bore 62 through the stop member 60 for coupling the stop member 60 to an elongate tensile member. Stop member 60 further includes a circumferential groove 64 which facilitates crimping the stop member on an elongate tensile member and also facilitates registration of the stop member 60 with a crimp tool which will be described below.

Figure 9:
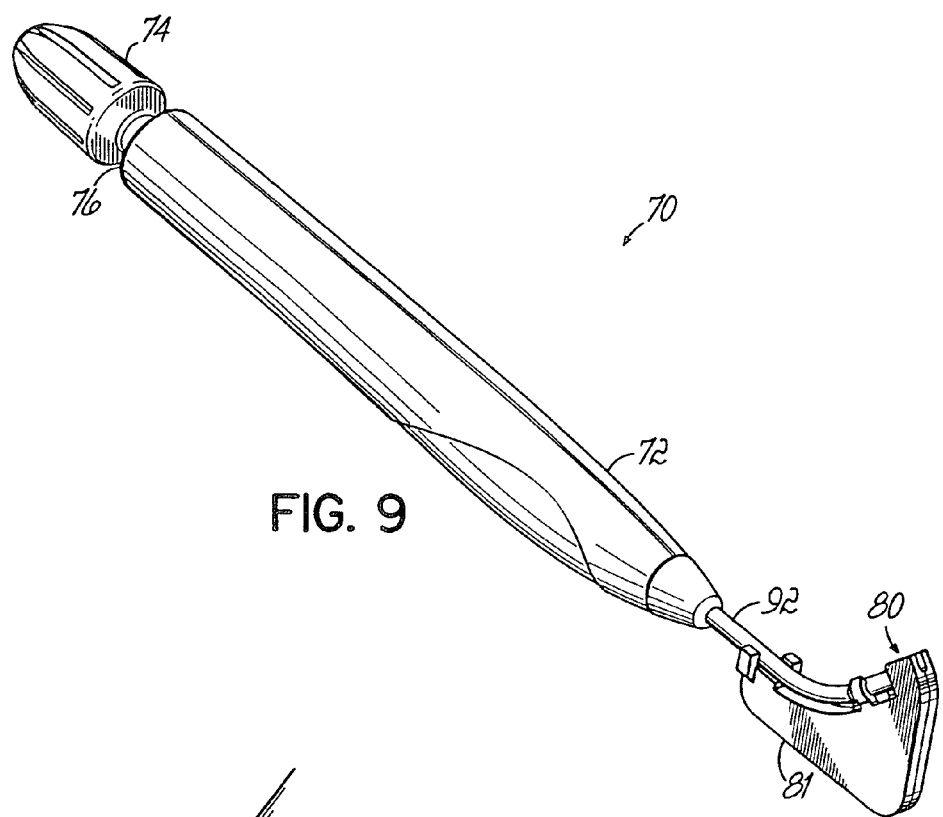
FIG. 9 is a perspective view showing an insertion tool for inserting the assembly of FIG. 1 into a tendon or ligament.
Figure 10:
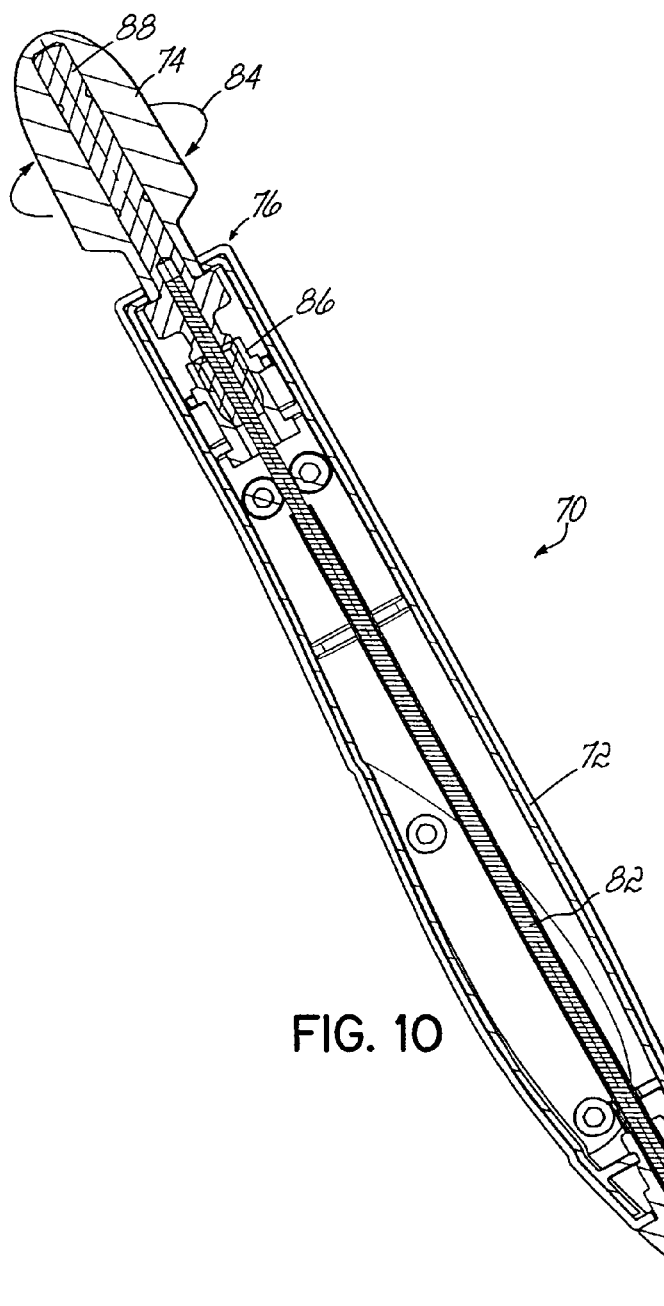
FIG. 10 is a cross-sectional view generally taken along the longitudinal axis of the insertion tool shown in FIG. 9.
Figure 10A:
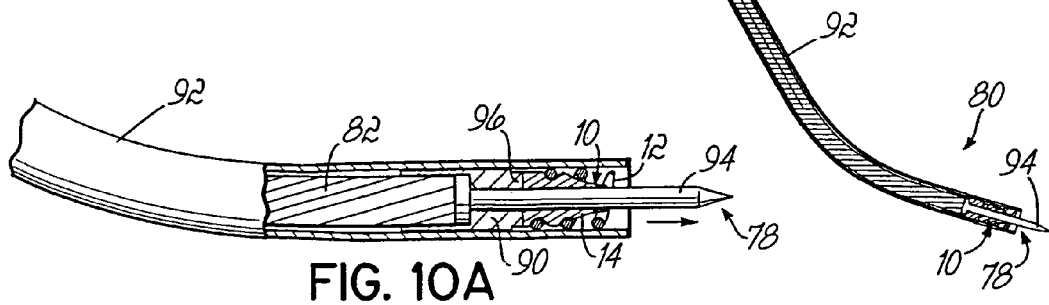
FIG. 10A is an enlarged view, partially cross-sectioned, of the distal end of the tool shown in FIG. 10.

FIGS. 9, 10 and 10A illustrate an exemplary anchor assembly insertion tool 70 for inserting soft tissue anchors, such as anchor assembly 10, 10a of FIGS. 1-4, within a tendon or ligament. Insertion tool 70 comprises an elongate body portion 72 having a rotatable knob 74 at a proximal end 76 and having a needle-shaped drive portion 78 (see FIG. 10) at a distal end 80. The tool 70 may be provided with a guard 81 fixed to the distal end 80, as depicted in FIG. 9, to protect the drive portion 78 prior to use. A flexible cable or shaft 82 is coupled between knob 74 and needle-shaped drive portion 78 and, in the preferred embodiment, this flexible shaft 82 is both rotated and translated as knob 74 is rotated in the direction of arrows 84 (see FIG. 10). A threaded coupling 86 within the elongate body portion 72 allows the simultaneous rotation and translation around and along axis 88 as knob 74 is rotated. Needle-shaped drive portion 78 is rigidly affixed to flexible shaft 82, as shown in FIG. 10A, through the use of a coupling member 90 and, preferably, an anchor assembly, such as anchor assembly 10 shown in FIGS. 1-2, is retained within a curved, tubular housing 92 which does not rotate but retains rotatable shaft 82 therein.

As shown in FIG. 10A, needle-shaped drive portion 78 includes a needle 94 which extends through anchor assembly 10 and further includes a projecting portion 96 which is complimentary to the tool engaging slot portion 32 of anchor assembly 10 (shown most clearly in FIGS. 1 and 4). The projecting portion 96 fits within slot 32 to allow rotation and translation of anchor assembly 10 as the needle 94 is both rotated and translated into a tendon or ligament in the direction of the arrow shown in FIG. 10A.

Figure 11:
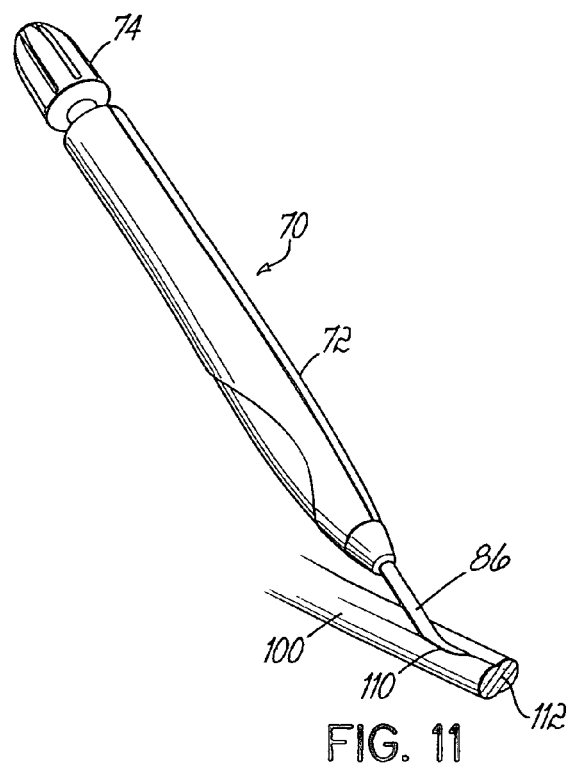
FIG. 11 is a perspective view illustrating the tool of FIG. 9 being used on a tendon or ligament.
Figure 12A:
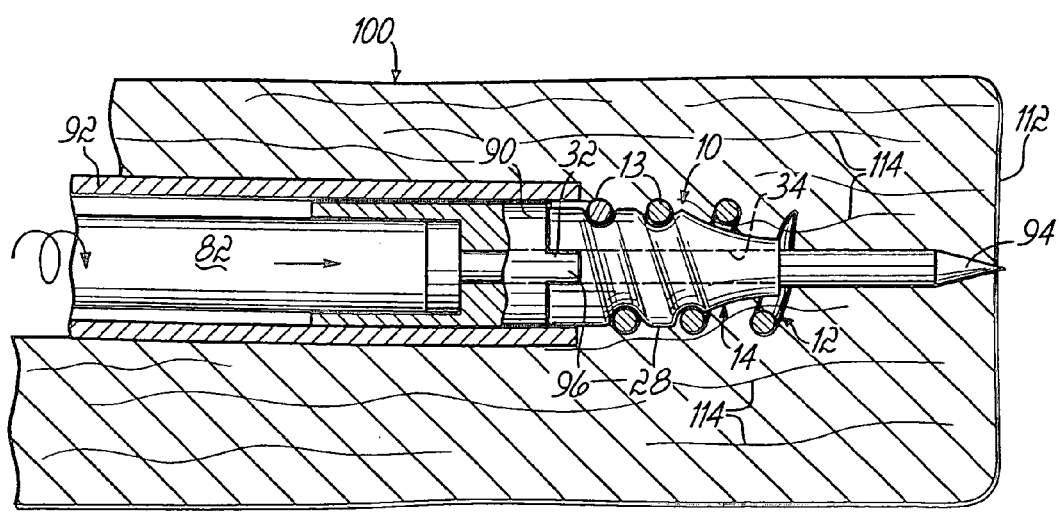
FIG. 12A is an enlarged cross-sectional view of the tool of FIG. 9 being used to drive the unitary anchor assembly of FIG. 1 into a tendon or ligament.

As more specifically shown in FIGS. 11 and 12A, anchor assembly 10 is rotated and translated, or moved axially, into a tendon or ligament 100 generally through an incision 110 proximate a severed end 112 and collagen fibers 114 are captured during this insertion process between the coils 13 of anchor 12 and the outside surface 28 of retaining member 14. During the insertion process, the coils 13 expand slightly outward away from the outer surface 28 of retaining member 14 due to their inherent spring action and, also due to their spring action, the coils 13 spring back to apply a force against the tendon or ligament fibers 114 and against the outer surface 28 of the retaining member 14. This forcefully traps fibers 114 and strengthens the connection between anchor assembly 10 and the tendon or ligament fibers 114.

Figure 12B:
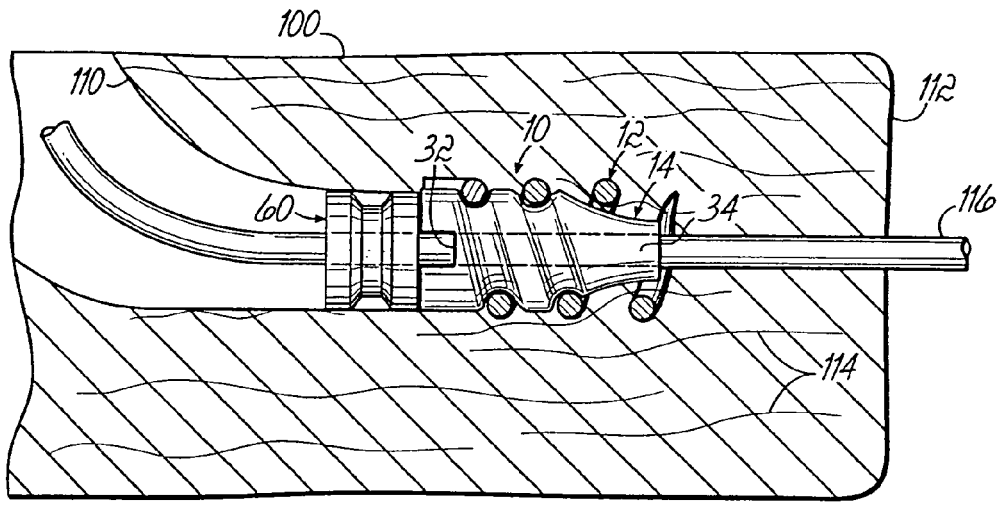
FIG. 12B is a partial cross-sectional view, similar to FIG. 12A, illustrating the anchor assembly inserted into the tendon or ligament and secured to a tensile member.

FIG. 12B shows an anchor 10 installed in the tendon 100 and an elongate tensile member 116 routed through bore 34 of anchor 10 and secured with a crimpable stop member 60 as will be described in more detail below. While FIG. 12B illustrates separate stop member 60 crimped to the elongate tensile member 116, it will be recognized that a stop member may alternatively be provided as an integral portion of retaining member 14 of anchor 10, or some other type of locking member may be used as desired.

Figures 13A, 13B:
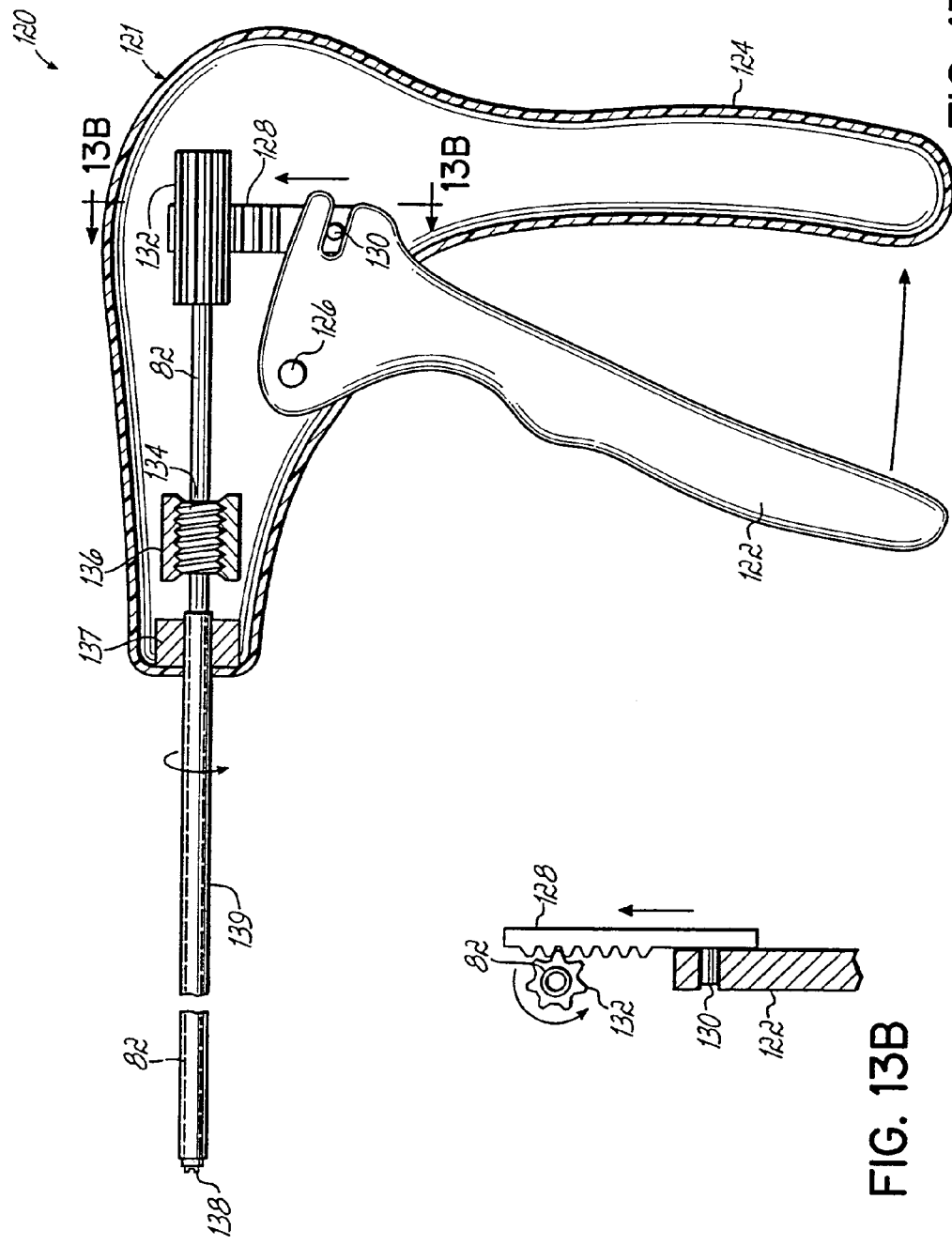
FIG. 13A is a side elevational view schematically showing an alternative pistol grip assembly for the insertion tool of FIG. 9 allowing one-handed operation by a surgeon.
FIG. 13B is a fragmented end view of the pistol grip assembly of FIG. 13A schematically illustrating the interaction between the rack and pinion drive.

FIGS. 13A and 13B illustrate a pistol grip device 120 for driving the shaft 82 of the tool 70, generally shown in FIGS. 9 and 10. Device 120 replaces knob 74 and is coupled to tool 70 by a coupling 138 at the end of flexible shaft 82 to allow one-handed operation by a surgeon. In this embodiment, a firing lever 122 may be actuated toward a handle 124 with a single hand of the surgeon to rotate the firing lever 122 about a pivot 126 and thereby drive a rack gear 128 upwardly, via a connecting pin 130, to rotate a pinion gear 132 coupled for rotation with flexible shaft 82. In this embodiment, shaft 82 includes an externally threaded portion 134 and an internally threaded nut 136 is rigidly affixed, so as not to rotate, within device 120. Shaft 82 extends through a tube 139 that is coupled to housing 121 by collar 137 and threaded portion 134 engages the internal threads of nut 136 and as shaft 82 rotates through the interaction of rack and pinion 128, 132, shaft 82 also translates to the left, as viewed in FIG. 13A to move drive portion 78 and anchor assembly 10 (FIG. 10A) into a tendon or ligament 100. Alternatively, if a translation mechanism were not provided, the surgeon could translate the anchor assembly 10 manually into the tendon or ligament 100 by simultaneously pushing the pistol grip handle assembly 120 while actuating the firing lever 122 to rotate shaft 82. Other forms of pistol grip or other one-handed actuators may be used and configured in any number of ways by those of ordinary skill to simultaneously rotate and, optionally, translate shaft 82.

Figure 14A:
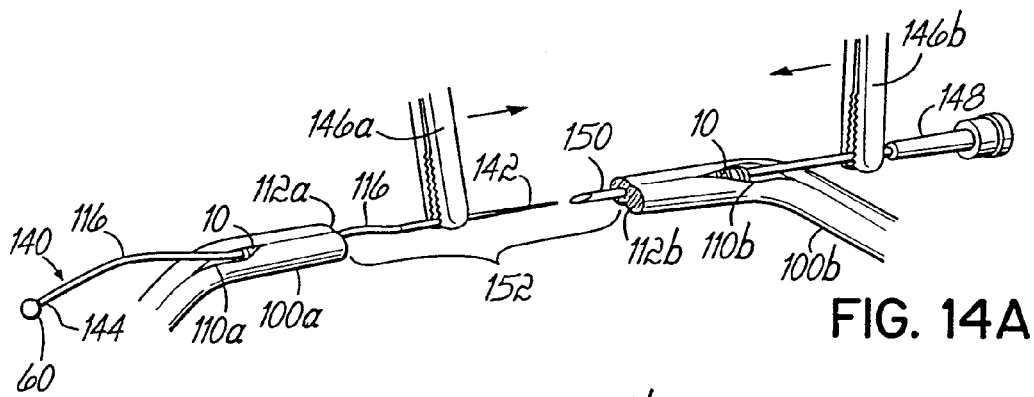
FIGS. 14A-14G are perspective views illustrating a tendon or ligament repair method utilizing two unitary anchor assemblies and an elongate, flexible tensile member.
Figure 14B:
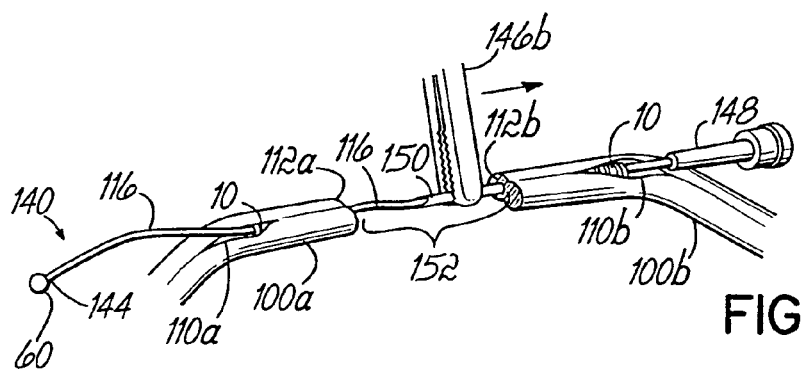
Figure 14C:
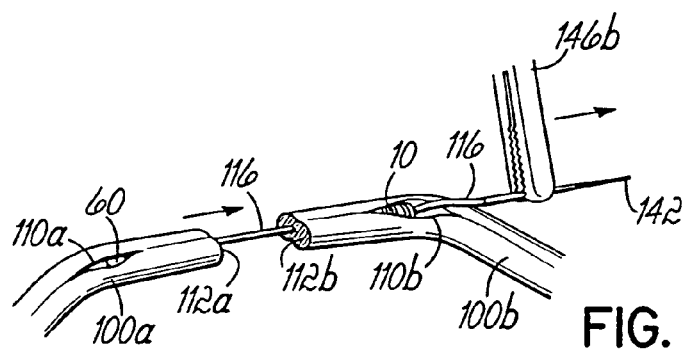

FIGS. 14A-14G illustrate one exemplary method out of many possible methods for utilizing anchor assembly 10 of FIG. 1 to repair a tendon or ligament 100. In this example, two anchor assemblies 10 are respectively driven into tendon or ligament segments 100a, 100b as shown in FIG. 14A and in a manner as described above. An assembly 140 comprising a distal needle 142 coupled with a flexible elongate tensile member 116, such as a multi-filament suture, and a preset stop member, such as crimpable stop 60, crimped onto a proximal end 144 of elongate tensile member 116 is threaded through a first one of the anchor assemblies 10 using a tool 146a until needle 142 is positioned between tendon or ligament segments 100a, 100b as shown in FIG. 14A. Although it may not specifically be stated herein, it is to be understood that passing elongate tensile member 116 through an anchor assembly 10 which has been driven into a tendon or ligament 100 includes passing the elongate tensile member 116 through the tendon or ligament 100. From the opposite side, a second tool 146b is used to thread a capturing member, which may be a conventional syringe or vena-puncture needle 148 having a tip 150, through the second anchor assembly 10 and into the space 152 between tendon or ligament segments 100a, 100b. The first needle 142 is then captured by inserting its end into the hollow interior of the syringe needle 148 and the connected assembly is then withdrawn through the second anchor assembly 10, as shown in FIGS. 14B and 14C. Alternatively, elongate tensile member 116 may be pushed through the second anchor assembly 10 without first being captured in space 152.

Figure 14D:
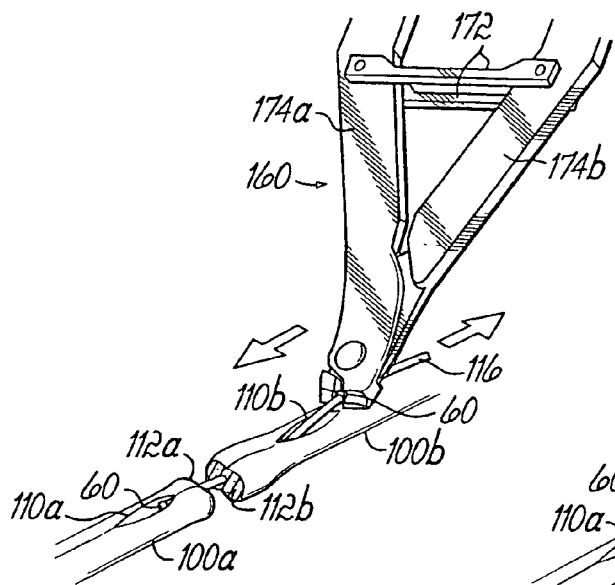
Figure 14E:
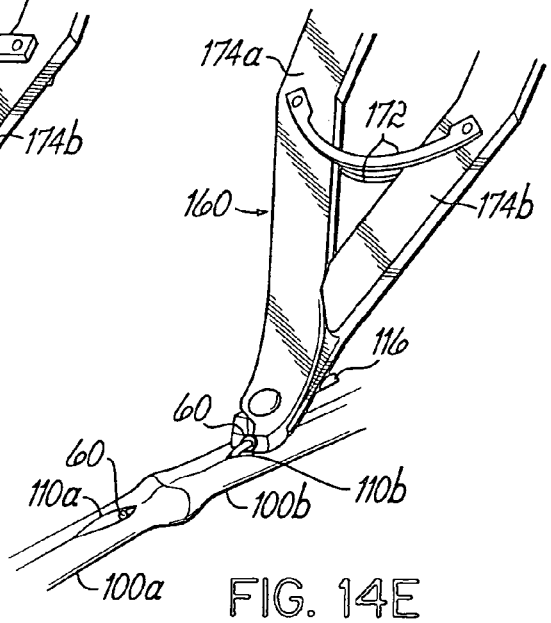
Figure 14F:
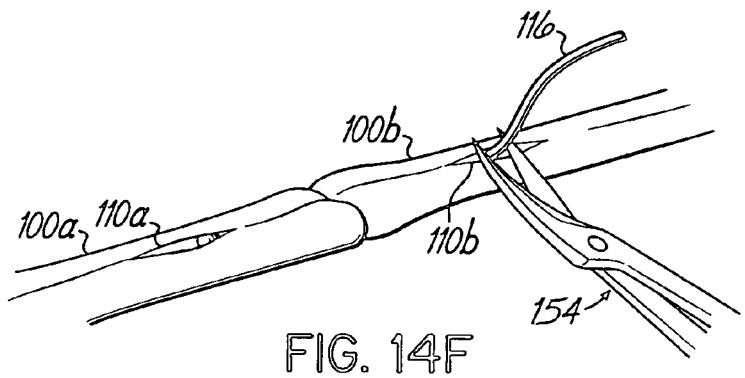
Figure 14G:
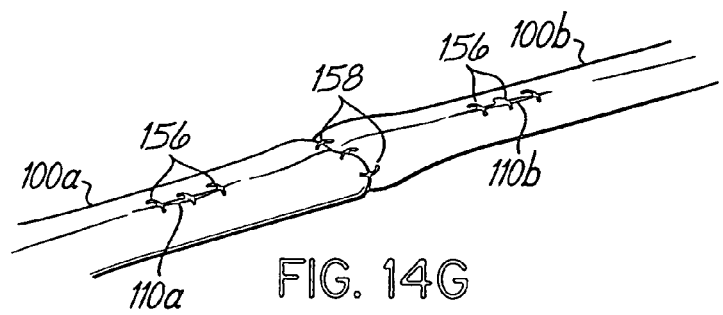

Tendon or ligament segments 100a, 100b are then drawn together using the well-secured anchor assemblies 10 as shown in FIGS. 14D and 14E. Anchor assembly 10 in ligament segment 100a is pulled by preset crimp member 60 as anchor assembly 10 in ligament segment 100b is pushed using a second stop member 60 and a crimp tool 160. Exemplary crimp tool 160 is then used to crimp second stop member 60 onto the flexible elongate tensile member 116 to retain the second anchor assembly 10 in position within segment 100b. The first anchor assembly 10 is retained in position by the preset stop member 60 as previously described. Thus, the tendon or ligament segments 100a, 100b are held at the desired positions relative to each other as determined by the surgeon. The excess length of the elongate tensile member 116 is then cut with a cutting tool 154 at a location adjacent the proximal end of the second stop member 60 as generally shown in FIG. 14F and, as shown in FIG. 14G, the access incisions 110a, 110b are closed, using sutures 156, for example, and an epitendinous suture 158, or other means, may be used to further secure the ends of the tendon or ligament segments 100a, 100b.

Figure 15:
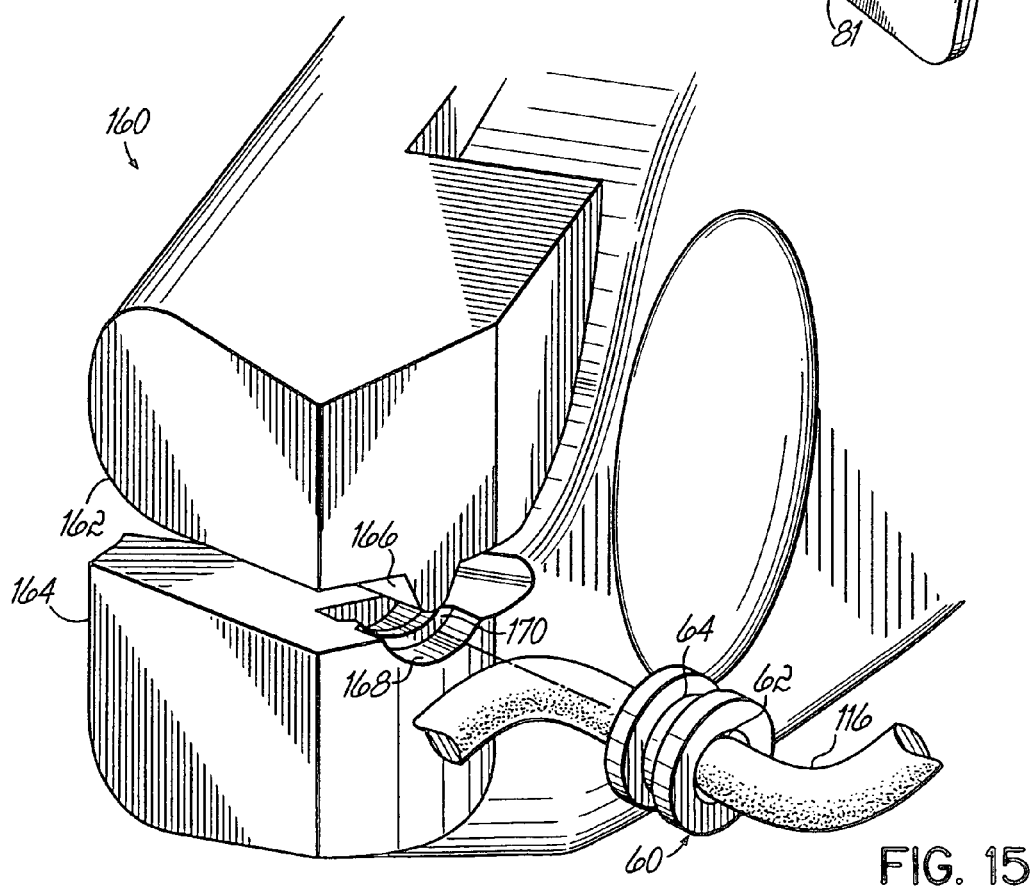
FIG. 15 is an enlarged perspective view showing the jaw portion of a crimp tool and a crimpable stop member, each constructed in accordance with additional aspects of the invention.

FIG. 15 shows the jaws 162, 164 of crimp tool 160 in more detail. A first jaw 162 includes a projection 166 for collapsing stop member 60 against a recess 168 formed in the second jaw 164. The recess 168 in jaw 164 includes a ridge 170 which engages groove 64 on stop member 60 to help retain stop member 60 in place within the jaws 162, 164, such as during shipping and during use by the surgeon. Referring to FIGS. 14D and 14E, one or more flexible bars 172 are provided between opposing handles 174a, 174b of crimp tool 160. These bars 172 retain the jaws 162, 164 at predetermined positions to hold the stop member 60 in place during packaging, shipping and storage, but prevent jaws 162, 164 from coming together during application of relatively light loads which might otherwise prematurely collapse the stop member 60. During use by the surgeon, however, the flexible bar or bars 172 do not prevent manual actuation of the handles 174a, 174b to bring the jaws 162, 164 together to collapse the stop member 60 as shown in FIG. 14E.

Figure 16:
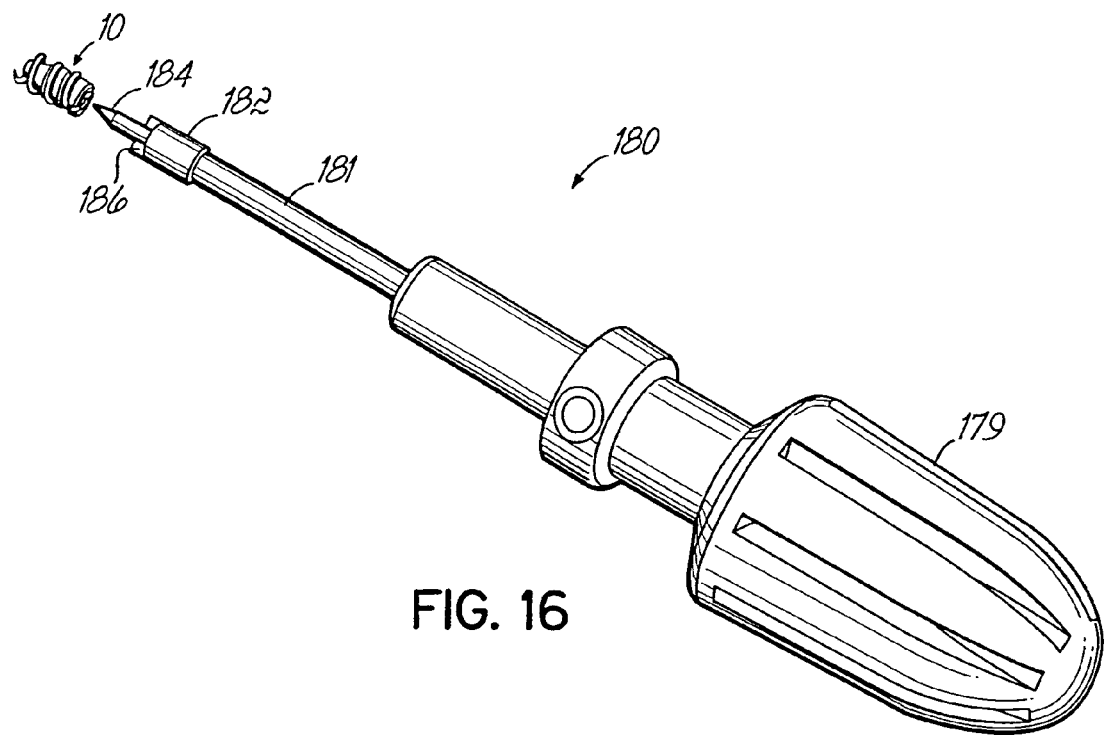
FIG. 16 is a perspective view of an anchor assembly removal tool in accordance with another aspect of the invention.
Figure 17:
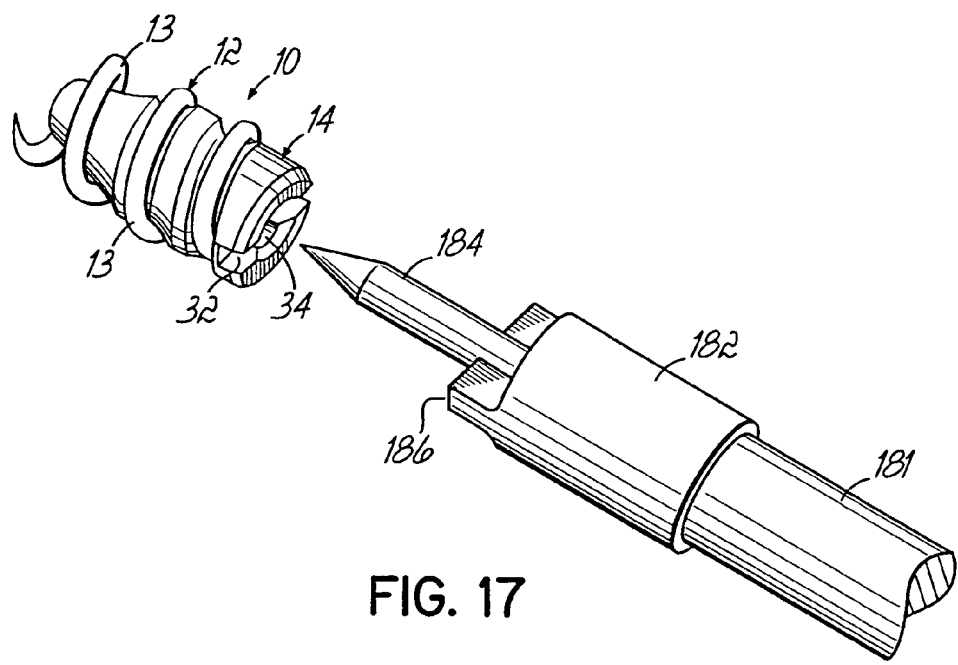
FIG. 17 is an enlarged perspective view of the distal end of the removal tool of FIG. 16 and the unitary anchor assembly of FIG. 1.

FIGS. 16 and 17 illustrate an exemplary removal tool 180 which, in certain cases, may be necessary to remove an anchor assembly 10. Specifically, removal tool 180 is in the general form of a rotatable hand tool, generally similar to a screwdriver, having a handle 179 and shaft 181, which may be flexible. As best shown in FIG. 17, tool 180 further includes a head portion 182 having a needle 184 extending from a drive portion 186. Needle 184 extends through the central bore 34 of anchor assembly 10 and drive portion 186 engages slot 32 of anchor assembly 10 in a manner similar to a screwdriver to thereby allow rotation of anchor assembly 10. In the configuration shown, counterclockwise rotation of tool 180 and anchor assembly 10 will back the anchor assembly 10 out of a tendon or ligament 100, for example, if the anchor assembly 10 is malpositioned.

Figure 18A:
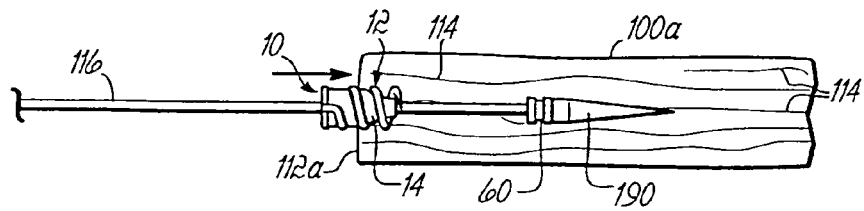
FIGS. 18A-18E are schematic illustrations depicting an exemplary method for repairing a severed tendon or ligament using exemplary apparatus of the invention.

Referring to FIGS. 18A-18E, an exemplary method for repairing a tendon or ligament which has been cut or severed will now be described. This method is particularly useful because the anchor assembly is inserted into the severed end. In surgery, it is frequently advantageous to approach the repair site in this manner. In FIG. 18A, an elongate tensile member 116, such as a multi-filament suture, is inserted into the severed end 112a of a first tendon segment 100a. The elongate tensile member 116 has a needle 190, attached to the distal end which is inserted into the tendon segment 100a, to facilitate insertion of the elongate tensile member 116 into the tendon segment 100a. Alternatively, the end of elongate tensile member 116 may be sharpened to facilitate insertion into the tendon or ligament segment 100a. A crimpable stop member 60 is also provided on the elongate tensile member 116 adjacent the needle 190 so that the crimpable stop member 60 is inserted into the tendon segment 100a with the needle 190. Alternatively, the stop member 60 may be provided pre-clamped to the elongate tensile member 116, or it may be applied to the elongate tensile member 116 for crimping by the surgeon after an end of the elongate tensile member 116 has been extended outside of the tendon segment 100a. Soft tissue anchor 10 is coupled to the elongate tensile member 116 and is inserted into the severed end 112a of the first tendon segment 100a using, for example, insertion tool 70.

Figure 18B:
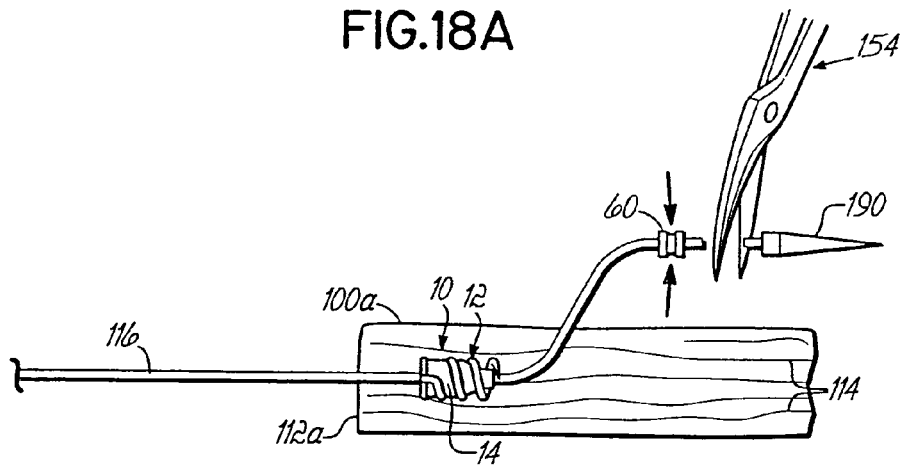
Figure 18C:
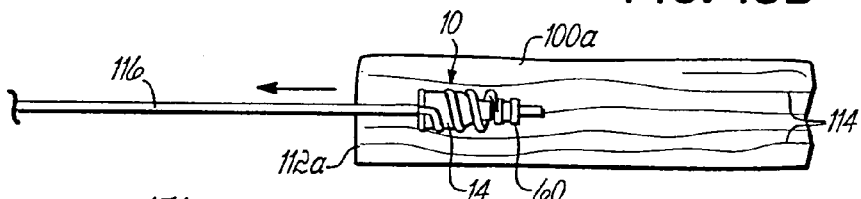
Figure 18D:
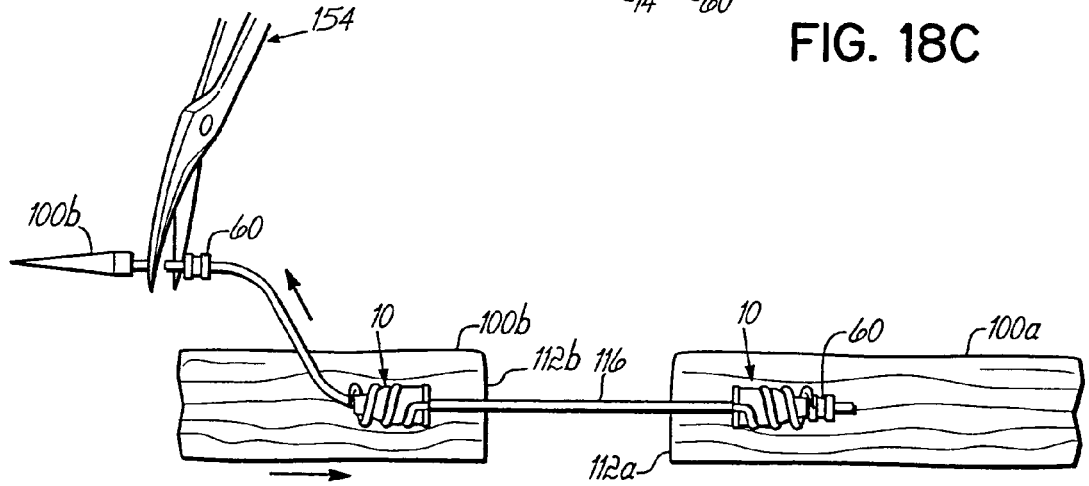

Referring to FIG. 18B, soft tissue anchor 10 is driven into tendon segment 100a to grip fibers 114 of the tendon segment. The needle 190 and elongate tensile member 116 are directed along the tendon segment 100a and then outside of a longitudinal sidewall of the tendon segment 100a so that the end of the elongate tensile member 116 extends beyond the sidewall of the tendon segment 100a, as depicted in FIG. 18B. The needle 190 is removed by cutting the elongate tensile member 116 using a cutting tool 154 and the stop member 60 may then be crimped to the elongate tensile member 116 using a tool, such as crimp tool 160 previously described. Tension is then applied to the elongate tensile member 116 to draw the extended portion of the elongate tensile member 116 and the stop member 60 back within the tendon segment 100a and to seat the stop member 60 against the soft tissue anchor 10, as shown in FIG. 18C.

Figure 18E:
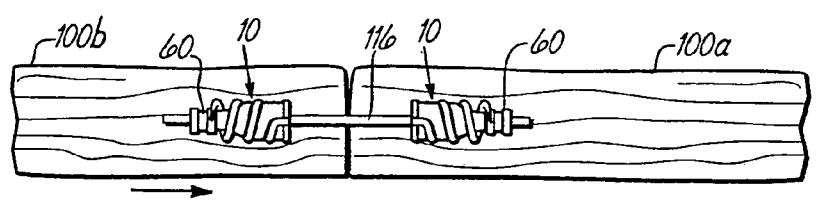

A second soft tissue anchor 10 is coupled to the elongate tensile member 116 and the opposite end of the elongate tensile member 116 is inserted into a second tendon segment 100b, following the procedure described above, as depicted in FIG. 18D. After the second needle 190 has been removed, tension is applied to the elongate tensile member 116 while urging a second stop member 60 along the elongate tensile member 116 to seat against the second tissue anchor 10. Tension is continued to be applied to the elongate tensile member 116 while applying force to the stop member 60 and second tissue anchor 10 to approximate the tendon segments 100a, 100b, as shown in FIG. 18E, using for example, crimp tool 160, as previously described with respect to FIGS. 14D and 14E. After the tendon segments 100a, 100b have been approximated and stop member 60 has been crimped, the elongate tensile member 116 may be cut using a cutting tool 154 and sutures may be applied as was described with respect to FIGS. 14F and 14G.

While the method for repairing a tendon or ligament has been described above with respect to using one soft tissue anchor 10 in each segment of the tendon or ligament, it will be recognized that two or more soft tissue anchors may be used in each segment, as may be desired, to repair a tendon or ligament.

Figure 19:
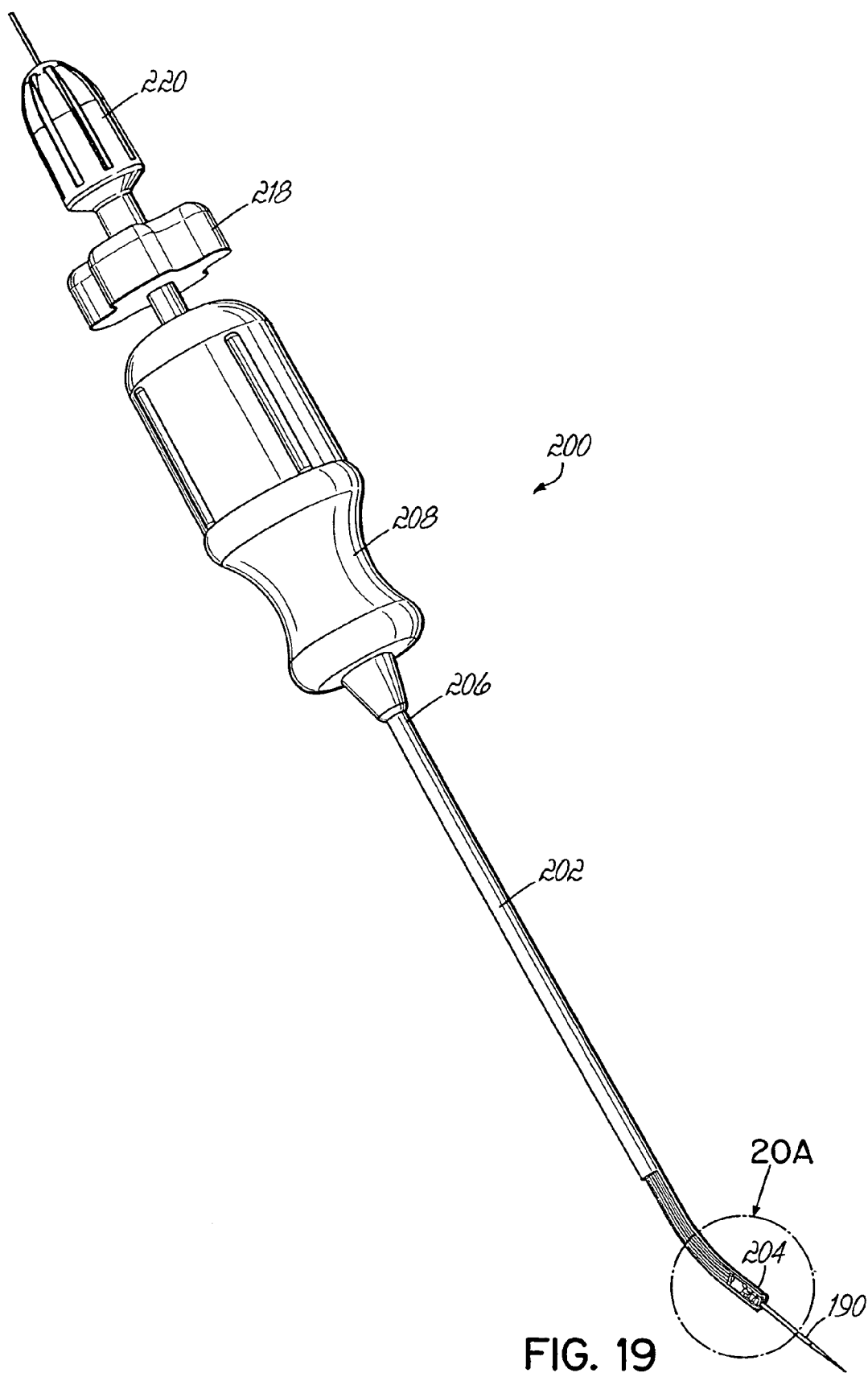
FIG. 19 is a perspective view of an exemplary tool for inserting a soft tissue anchor into, and driving a tensile member through, a tendon or ligament.

Referring to FIGS. 19 and 20A, there is shown an exemplary tool 200 for installing a soft tissue anchor into a tendon or ligament and driving a needle and elongate tensile member into the tendon or ligament. The tool 200 includes an elongate tubular housing 202 having a first end 204 and a second end 206. The first end 204 of the housing 202 is configured to receive a soft tissue anchor 10 and a handle 208 is provided at the second end 206. As shown in FIG. 20A, a tubular shaft 210 is disposed within the housing 202 and is coupled with a first knob 218 (FIG. 19) provided on handle 208 at an end opposite the housing 202. Shaft 210 extends through the housing 202 to the first end 204 and is coupled to a drive head 212 having a projecting portion 214 near the first end 204 of the housing 202. The projecting portion 214 is configured to engage the drive slot 32 on a soft tissue anchor 10 and first knob 218 may be manipulated to rotate the shaft 210 while advancing the shaft 210 to extend beyond the first end 204 of the housing 202 in a manner similar to the operation of the anchor insertion tool 70 described above. Accordingly, the soft tissue anchor 10 received in the first end 204 of the housing 202 is driven into a tendon or ligament by the drive head 212 when the first knob 218 is manipulated.

The tool 200 further includes a tubular inner member 216 disposed concentrically within the shaft 210 and having an inner channel sized to receive an elongate tensile member 116 such as a multi-filament suture. The tubular inner member 216 is coupled at one end to a second knob 220 located on handle 208 adjacent first knob 218 (see FIG. 19). When the second knob 220 is manipulated, either by rotation or, alternatively, by axial movement, the inner member 216 is advanced along the inner bore 222 of the tubular shaft 210 to extend beyond the first end 204 of the housing 202. Advantageously, when an elongate tensile member 116 disposed within the tubular inner member 216 is provided with a needle 190, the tubular inner member 216 may be used to advance the needle 190 and elongate tensile member 116 into a tendon or ligament as the second knob 220 is manipulated to advance the inner member 216. Referring to FIG. 20E, there is shown an alternative exemplary embodiment of tool 200, wherein housing 202a is configured to include anti-rotation structure for preventing the tendon 100 from rotating with anchor assembly 10 during installation of the anchor assembly. In the embodiment shown, the anti-rotation structure includes spikes 224 which flare outwardly into a tendon from the first end 204 of housing 202a when extended from a retracted position within housing 202a, as disclosed in PCT application PCT/US99/24098, filed Oct. 18, 1999 and herein incorporated by reference in its entirety.

FIGS. 20B-20D illustrate operation of tool 200 to insert a soft tissue anchor assembly 10 within a tendon or ligament 100 and to advance an elongate tensile member 116 into the tendon 100. In FIG. 20B, the first end 204 of the housing 202 has been inserted through an incision in the tendon 100 and the first knob 218 has been manipulated to rotate and advance the shaft 210 along the housing 202 so that the anchor assembly 10 is advanced from within the first end 204 of the housing 202 and into the interior of the tendon 100. As the soft tissue anchor assembly 10 moves forward into the tendon 100 while rotating, the fibers 114 of the tendon 100 are captured between the coils 13 of the helical anchor 12 and the retaining member 14, as previously described.

In FIG. 20C, the needle 190 and elongate tensile member 116 are advanced beyond the first end 204 of the housing 202 and through the tendon 100, being urged by the inner member 216 which is advanced by manipulation of the second knob 220. The needle 190 and elongate tensile member 116 are extended by the inner member 216 until they protrude from the severed end 112 of the tendon 100. Once the needle 190 and elongate tensile member 116 have protruded through the severed end 112 of the tendon 100, the housing 202 of tool 200 is withdrawn from the tendon 100 through the incision, leaving the soft tissue anchor assembly 10 embedded in the tendon 100 and coupled to the elongate tensile member 116, as depicted in FIG. 20D. A stop member 60 may then be coupled to the elongate tensile member 116 and the elongate tensile member 116 pulled to seat the stop member 60 against the soft tissue anchor assembly 10, similar to the process described above for FIGS. 18B and 18C.

Referring to FIGS. 21 and 22A-22C, an exemplary tool 230 for crimping a crimpable stop member 60 and cutting an elongate tensile member 116 will now be described. The crimp-and-cut tool 230, shown in FIG. 21, includes an elongate housing member 232 having a first end 234 and a second end 236. The first end 234 of the tool 230 has a crimp jaw 238 for receiving a crimpable stop member 60 therein. An aperture 239 adjacent crimp jaw 238 permits the elongate tensile member 116, to which the stop member 60 will be secured, to pass through the housing 232 and holds the elongate tensile member 116 for cutting. A handle 240, which may include a thumb brace 242, is provided at the second end 236 of the housing 232. Tool 230 further includes a crimp bit 244, having a crimping edge 246, and a cutting member 248, having a cutting edge 250, disposed proximate the first end 234 of the housing 232. The crimp bit 244 and cutting member 248 are moveable with respect to the housing 232 to engage stop member 60 and elongate tensile member 116, respectively, retained in the crimp jaw 238 and aperture 239.

An actuating structure 252, shown in this exemplary embodiment in the form of a lever 252, is pivotally attached by a pin 254 near the second end 236 of the housing 232. The lever 252 is coupled to the crimp bit 244 and the cutting member 248, whereby rotation of the lever 252 toward the handle 240 moves the crimp bit 244 and cutting member 248 in a direction toward the crimp jaw 238 and aperture 239 so that stop member 60 is crimped by the crimp bit 244 and elongate tensile member 116 is then cut by cutting member 248 after stop member 60 has been crimped. A biasing member 253 between the handle 240 and the actuating lever 252 keeps the lever 252 in a position relative to the handle 240 whereby the crimping edge 246 and cutting edge 250 of the tool 230 are maintained at a desired position with respect to a stop member 60 retained in crimp jaw 238. While the actuating structure of crimp-and-cut tool 230 has been depicted and described as a pivotable lever 252, the actuating structure may have other configurations, such as a sliding lever, a gear train, a push button, or any other structure suitable to initiate movement of crimp bit 244 and cutting member 248 for crimping stop member 60 and cutting elongate tensile member 116.

In the exemplary embodiment shown, the actuating lever 252 is coupled to the crimp bit 244 by a crimp bit engagement arm 256 and to the cutting member 248 by a cutting member engagement arm 258. The tool 230 may further include a spring element 245 disposed between crimp bit 244 and crimp bit engagement arm 256 to bias crimp bit 244 toward first end 234 and thereby hold a stop member 60 in jaw 238 without crimping the stop member 60. In an exemplary embodiment, the biasing member 253 maintains the crimp bit engagement arm 256 at a position where crimping edge 246 abuts the stop member 60, while spring element 245 provides a pressure sufficient to retain the stop member 60 in the crimp jaw 238 without crimping the stop member 60. Biasing member 253 also helps to prevent premature actuation of actuating lever 252 to crimp stop member 60. In the exemplary embodiment depicted in FIG. 21, engagement of biasing member 253 with protrusion 251 on actuating lever 252 creates a threshold force which must be overcome to cause a free end 255 of biasing member 253 to move over the protrusion so that actuating lever 252 can be pivoted about pin 254 toward handle 240.

Figure 22A:
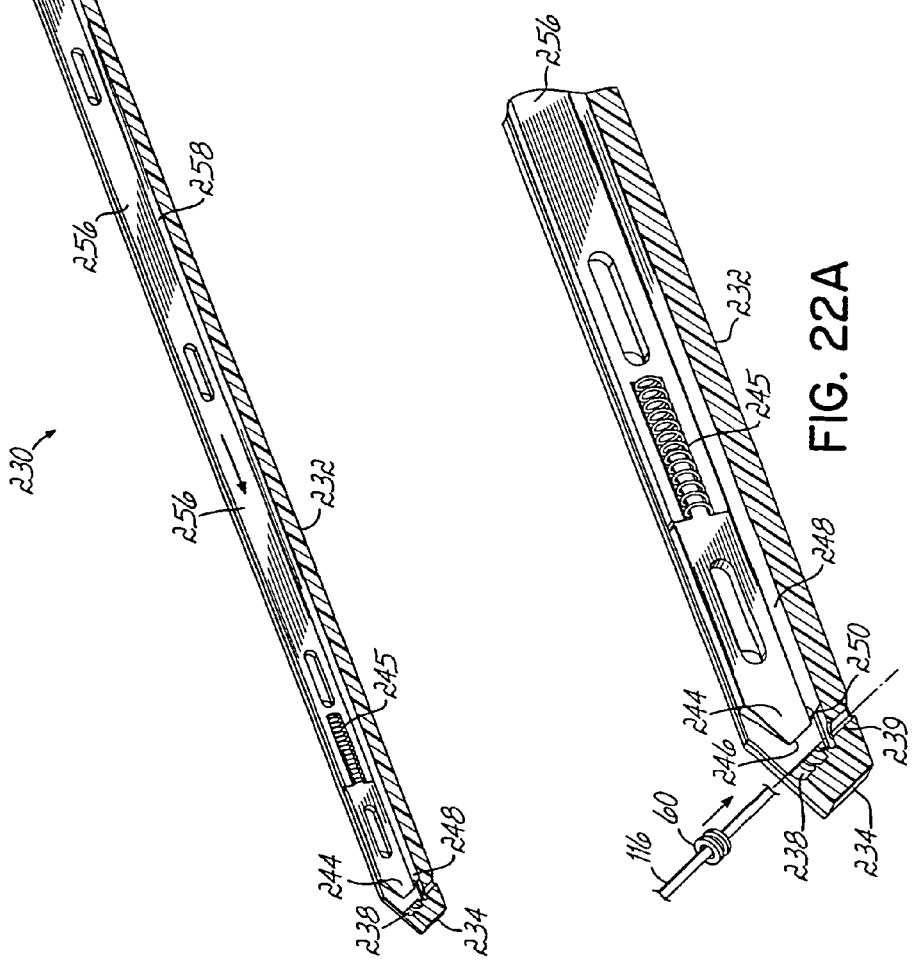
FIGS. 22A-22C are cross-sectional detail views of the exemplary tool of FIG. 21, illustrating use of the tool to crimp a stop member and cut a tensile member.
Figure 22B:
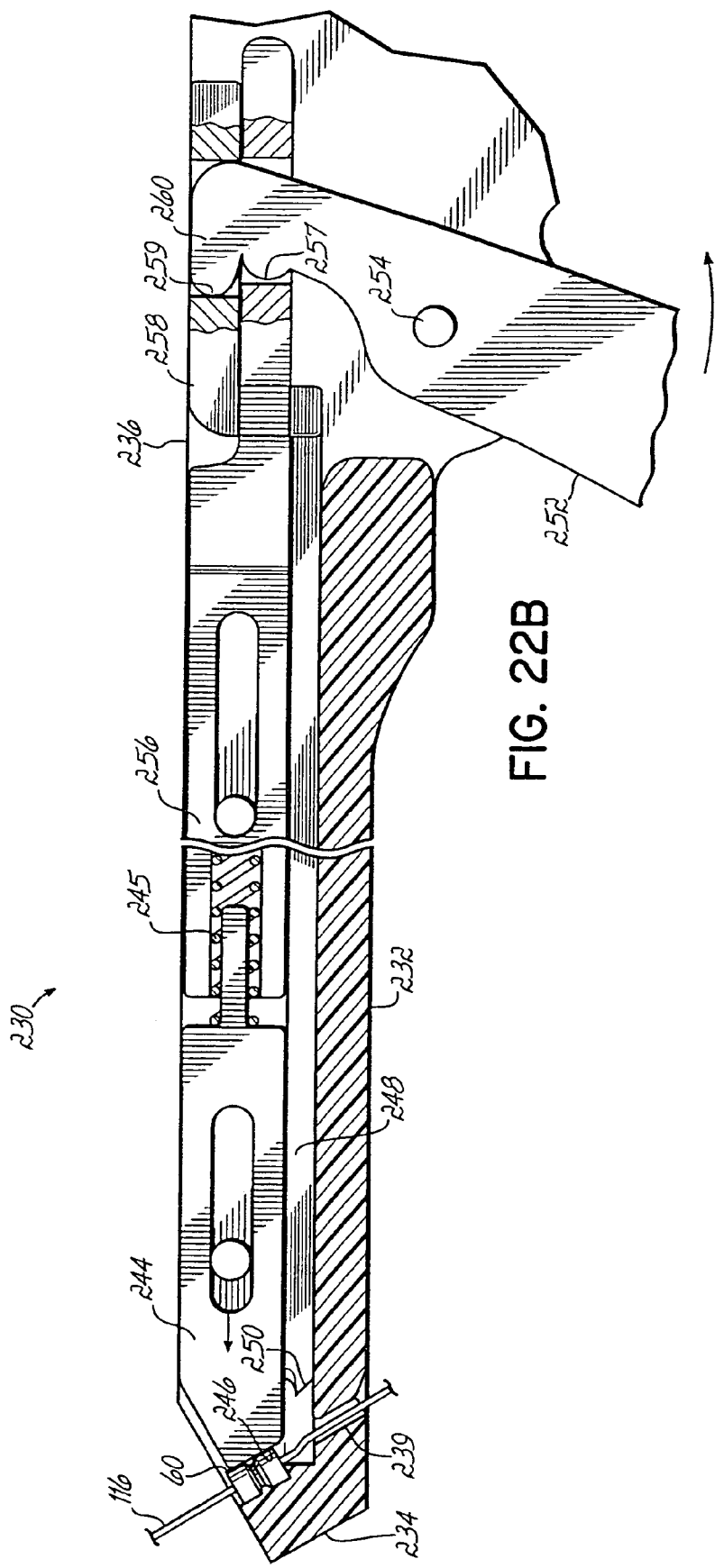

Operation of the exemplary cut-and-crimp tool 230 to crimp a stop member 60 and simultaneously cut an elongate tensile member 116 will now be described with respect to FIGS. 22A-22C. Referring to FIGS. 22A-22B, a crimpable stop member 60 is installed into the crimp jaw 238 of the tool 230 and elongate tensile member 116 coupled to the stop member 60 extends through aperture 239 in the housing 232. In FIG. 22B, actuating lever 252 is shown in an extended position, away from the handle 240, whereby the crimping edge 246 of crimp bit 244 abuts stop member 60 and cutting member 248 is spaced from the elongate tensile member 116. Spring element 245 urges crimp bit 244 toward first end 234 with a force sufficient to retain stop member 60 in jaw 238.

Figure 22C:
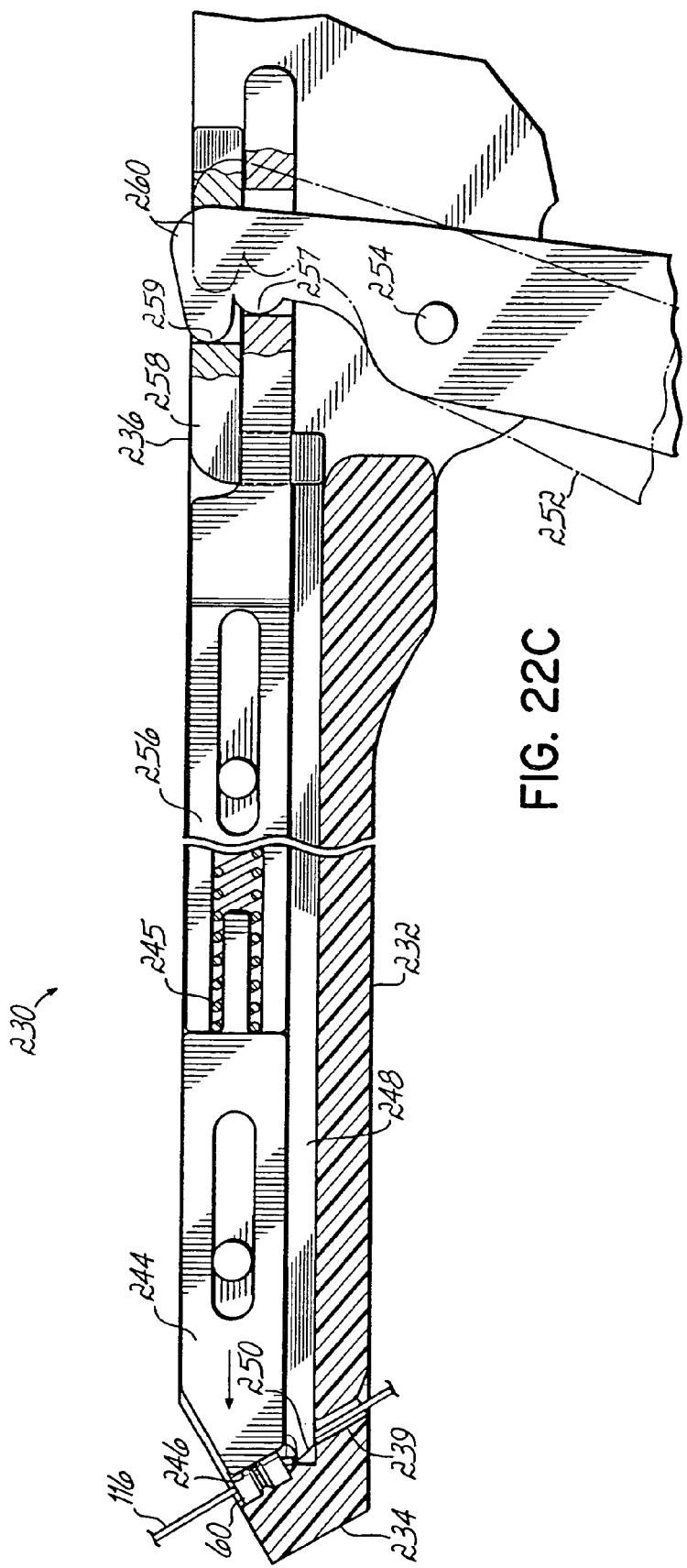

In FIG. 22C, the actuating lever 252 has been pivoted about pin 254, in a direction toward the handle 240, whereby first and second cam surfaces 257, 259 located at a driving end 260 of the actuating lever 252 urge the crimp bit engagement arm 256 and the cutting member engagement arm 258, respectively, in a direction toward the first end 234 of housing 232.

As the crimp bit engagement arm 256 and the cutting member engagement arm 258 are moved forward, the crimp bit 244 and cutting member 248 are forced into engagement with the stop member 60 and elongate tensile member 116, respectively, whereby the crimping edge 246 of the crimp bit 244 crimps the stop member 60 and the cutting edge 250 of cutting member 248 severs the elongate tensile member 116 adjacent the stop member 60. In an exemplary embodiment, the cam surfaces 257, 259 on driving end 260 are configured such that crimp bit 244 crimps stop member 60 immediately before cutting edge 250 cuts elongate tensile member 116. Advantageously, the first end 234 of the housing 232 may be inserted within a tendon or ligament to facilitate the crimping of a stop member 60 and cutting of an elongate tensile member 116 during the repair of a tendon or ligament.

Figure 21:
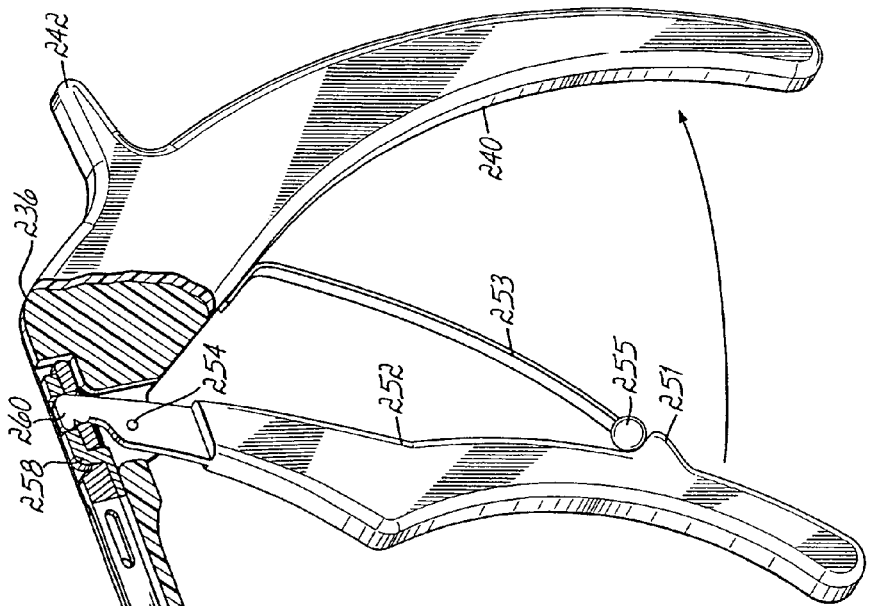
FIG. 21 is perspective view, partially cross-sectioned, of an exemplary tool for crimping a stop member on a tensile member and cutting the tensile member.
Figure 23C:
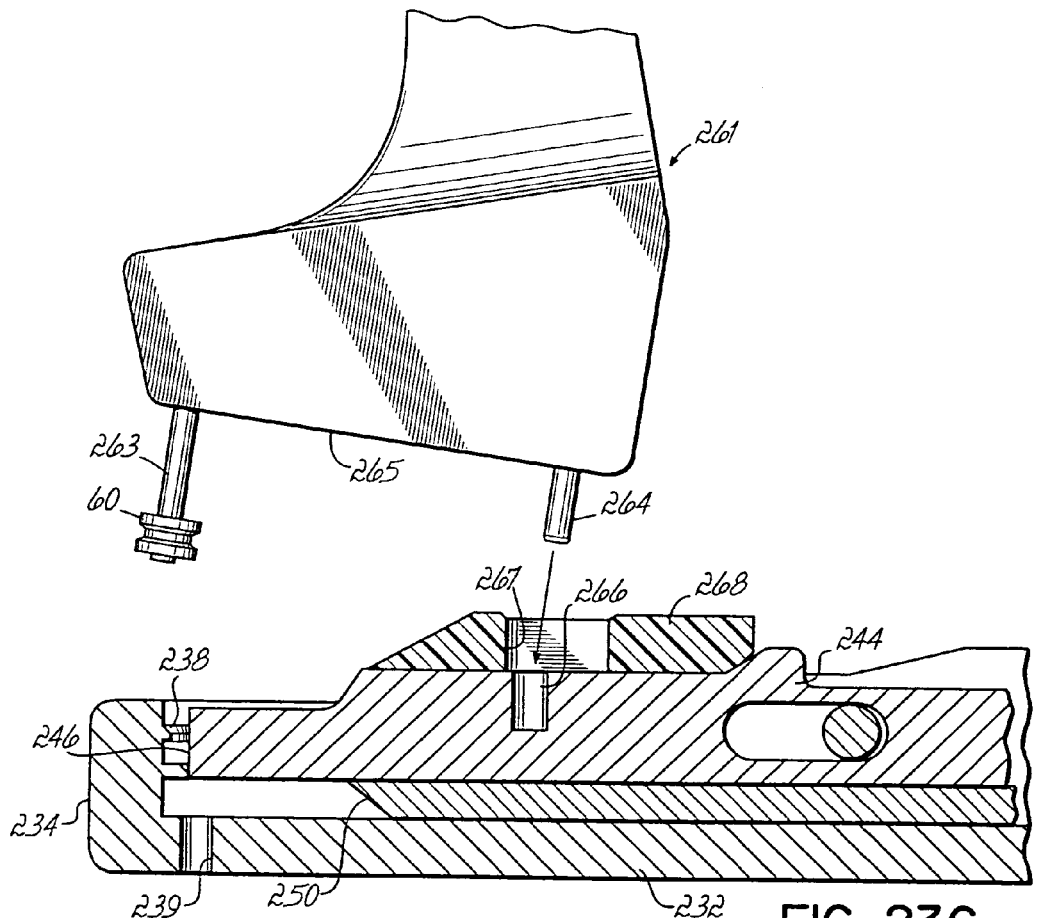
FIGS. 23C-23E are enlarged, cross-sectional views of the crimping tool and loading tool of FIG. 23A, illustrating use of the loading tool to load a stop member into the crimping tool.
Figure 23D:
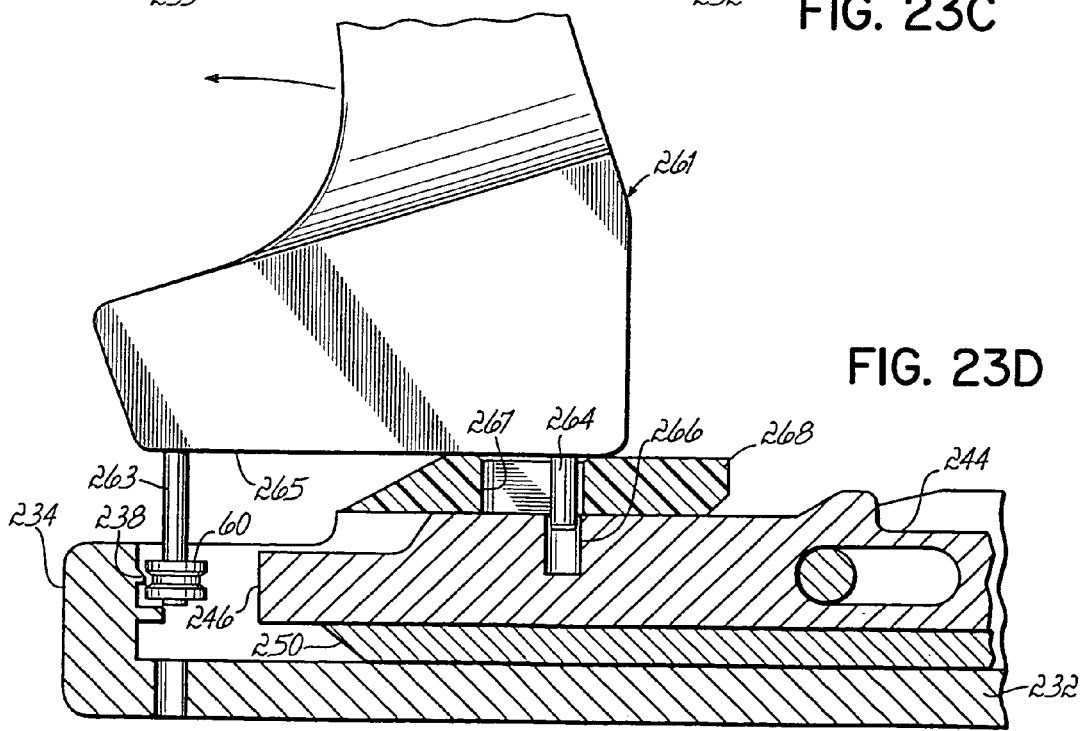
Figure 23E:
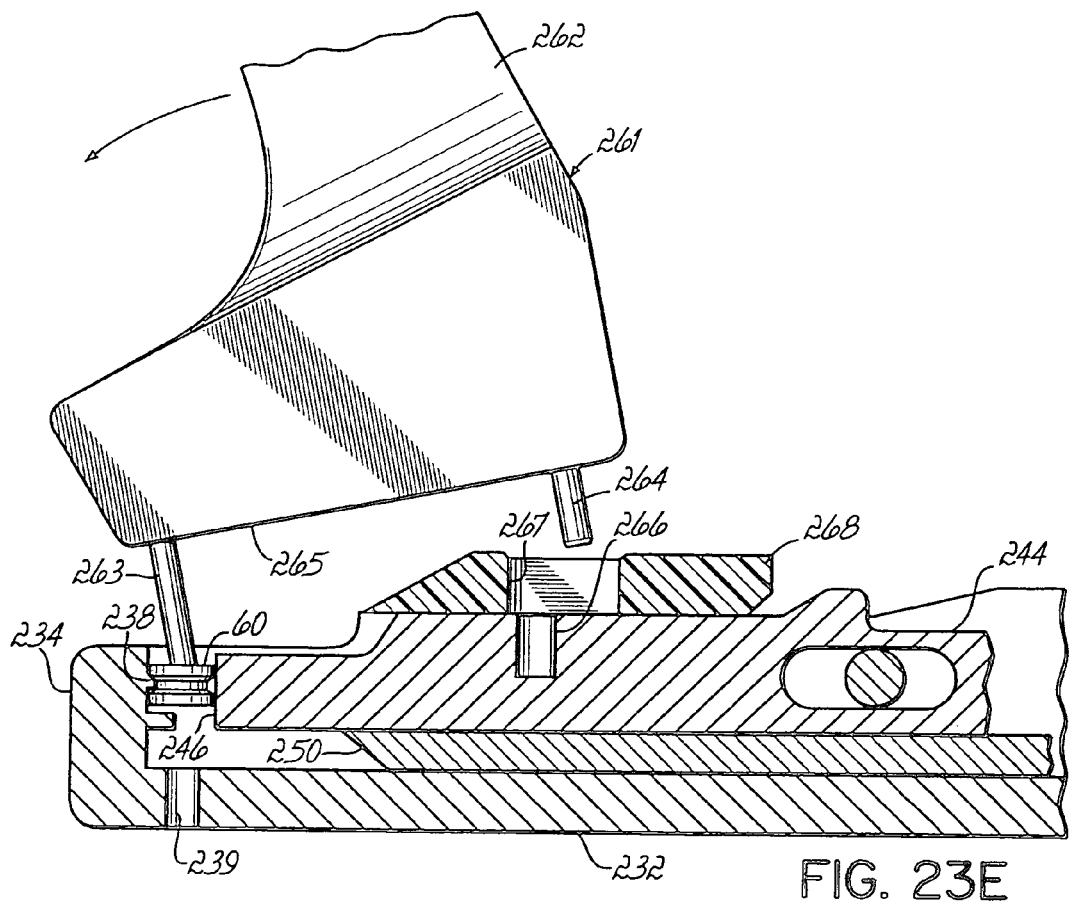
Figure 23F:
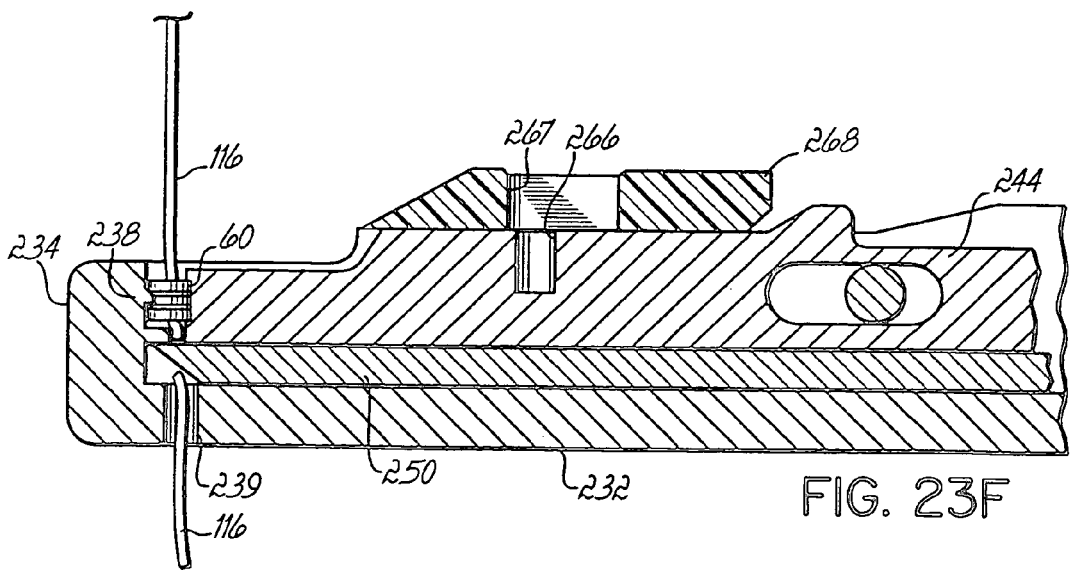
FIG. 23F is an enlarged cross-sectional view of the crimping tool of FIG. 23A, illustrating use of the tool to crimp a stop member and cut a tensile member.

FIGS. 23A-23F depict an alternative embodiment of the exemplary crimp-and-cut tool 230a, similar to the crimp-and-cut tool 230 of FIGS. 21 and 22, but having an alternate tip configuration proximate first end 234. FIGS. 23A-23E further illustrate a stop member loading device 261, which may be used to load stop members 60 into the crimp jaw 238 of the crimp-and-cut tool 230, 230a. Loading tool 261 includes an elongate handle 262 with first and second pins 263, 264 positioned on a proximal end 265 of the handle 262, as best depicted in FIG. 23C. The first pin 263 is configured to receive a stop member 60 and the second pin 264 is configured to engage a recess 266 in the crimp bit 244 whereby the proximal end 265 of the loading tool 261 may be coupled with the first end 234 of the crimp-and-cut tool 230, 230a to move crimp bit 244 away from crimp jaw 238 and insert stop member 60 into the crimp jaw 238. Specifically, the second pin 264 is inserted into the recess 266 in the crimp bit 244 through an aperture 267 in a cap plate 268 located near the first end 234 of housing 232, as illustrated in FIG. 23D. With the second pin 264 inserted within the recess 266, the loading tool 261 may be used to slide the crimp bit 244 in a direction toward the second end 236, against the bias force created by spring member 245, thereby moving the crimping edge 246 away from the crimp jaw 238 so that stop member 60 positioned on first pin 263 may be placed within the crimp jaw 238, as shown in FIG. 23D. After stop member 60 has been inserted within crimp jaw 238, handle 262 may be rotated in the direction of the arrow in FIG. 23D, such that second pin 264 is withdrawn from recess 266 in the crimp bit 244 whereby crimp bit 244 is urged toward the first end 234 of housing 232 under the action of the spring member 245 to engage stop member 60 with a pressure sufficient to retain the stop member 60 between the crimp jaw 238 and the crimping edge 246, as illustrated in FIG. 23E. When it is desired to crimp the stop member 60 on an elongate tensile member 116 which has been coupled with stop member 60, the first end 234 of crimp-and-cut tool 230, 230a may be positioned proximate a tendon repair location and the actuating lever 252 moved in a direction toward handle 240 to crimp the stop member 60 and sever the elongate tensile member 116, as illustrated in FIG. 23F and described in detail above.

FIG. 23G depicts another exemplary loading tool 261a, similar to loading tool 261 of FIG. 23A, but further including a downwardly extending arm 269 located at the proximal end 265 adjacent first pin 263. Arm 269 is configured to register against the first end 234 of the crimp-and-cut tool 230, 230a to facilitate installation of stop member 60 into crimp jaw 238.

Figure 24A:
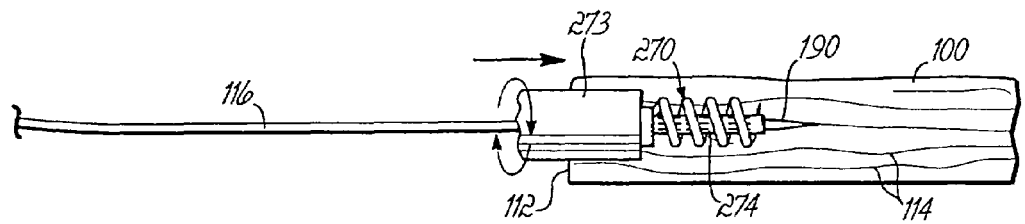
FIGS. 24A-24D are schematic illustrations depicting another exemplary soft tissue anchor assembly of the present invention and a method of installing the anchor assembly in a tendon or ligament.
Figure 24B:
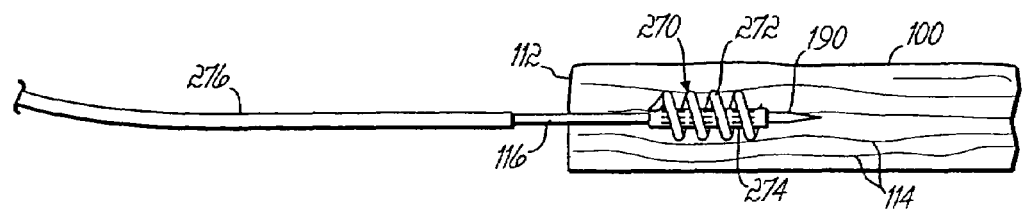

With reference to FIGS. 24A-24D, there is shown another exemplary soft tissue anchor assembly 270 of the present invention, described in conjunction with a method of inserting the soft tissue anchor assembly 270 within a tendon or ligament 100. As best shown in FIG. 24B, the exemplary soft tissue anchor assembly 270 comprises a helical coil anchor 272 and an expandable retaining member 274. The retaining member 274 may be expanded from a first state (see FIGS. 24A, 24B) wherein the outer surface of the retaining member 274 is spaced from the interior of the helical anchor 272 to a second, expanded state (see FIGS. 24C-24E) wherein the outer surface of the expandable retaining member 274 engages the interior of the helical anchor 272. Advantageously, the anchor assembly 270 may be inserted within a ligament or tendon 100 whereby the fibers 114 of the ligament or tendon 100 may be captured between helical anchor 272 and the contracted retaining member 274, whereafter, upon expansion of the retaining member 274, the fibers 114 will be captured and held between the helical anchor 272 and the expanded retaining member 274. FIG. 24E illustrates the retaining member 274 expanded against helical anchor 272 to capture fibers 114 therebetween.

With further reference to FIGS. 24A-24D, a method of installing the anchor assembly 270 will now be described. In FIG. 24A, the anchor assembly 270 is coupled to an elongate tensile member 116, having a needle 190 coupled to its leading end, and is inserted into the severed end 112 of a ligament or tendon 100 using an appropriate insertion tool 273, similar to those previously described. As the tissue anchor 270 is inserted within the tendon 100, fibers 114 of the tendon 100 are gathered between the helical coil 272 and the contracted retaining member 274 as the helical coil 272 is rotated and advanced into the tendon 100. In FIG. 24B, the insertion tool 273 is removed and an expansion actuator 276, such as a hollow tube installed over elongate tensile member 116, is positioned proximate the anchor assembly 270.

Figure 24C:
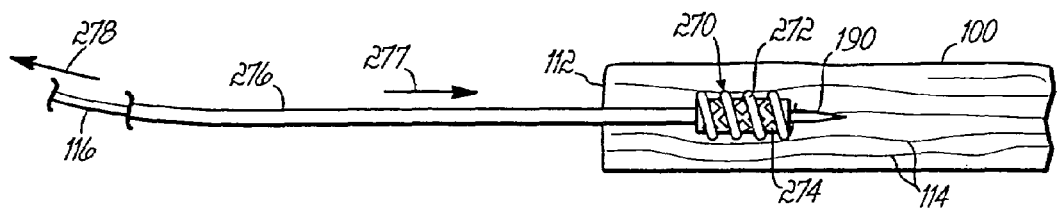
Figure 24E:
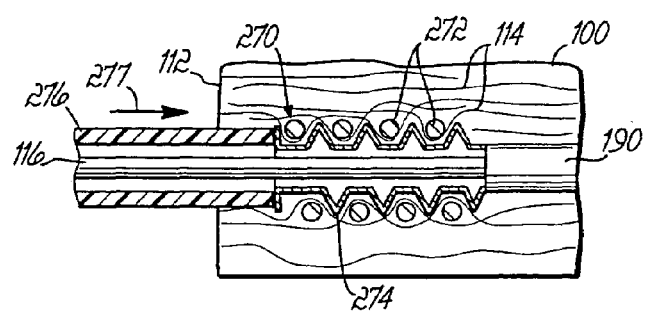
FIG. 24E is a schematic illustration of a cross-section of the soft tissue anchor assembly of FIGS. 24A-24D, depicting a retaining member of the anchor assembly in an expanded condition.
Figure 24F:
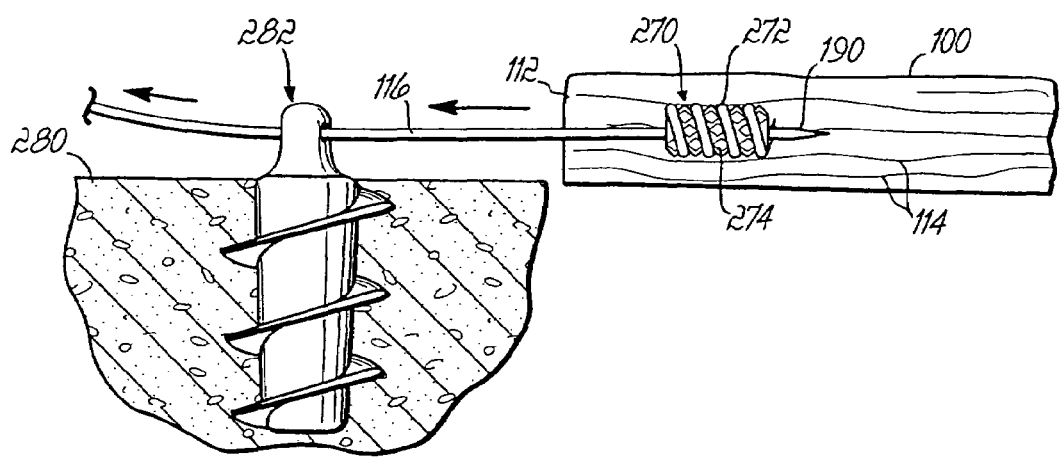
FIG. 24F is a schematic illustration of the soft tissue anchor assembly of FIGS. 24A-24E being used with a bone anchor to approximate a tendon or ligament.
Figure 24D:
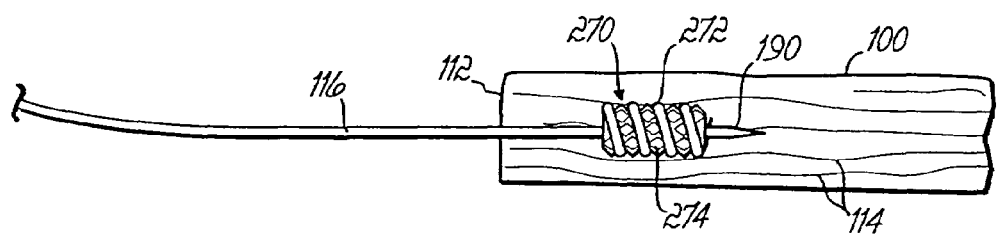

In FIG. 24C, the expansion actuator 276 is placed into engagement with the retaining member 274 to expand the retaining member 274 and thereby capture fibers 114 as described above. Specifically, the actuator 276 is moved along the elongate tensile member 116 in the direction of arrow 277 while tension is applied to the elongate tensile member 116 in the direction of arrow 278 to compress the retaining member 274 between the needle 190 and the actuator 276 and thereby expand the retaining member 274. After the retaining member 274 has been expanded, the actuator 276 may be removed from the elongate tensile member 116 as depicted in FIG. 24D. The opposite end of the elongate tensile member 116 may then be attached to another tendon or ligament segment using methods, for example, similar to those previously described, or to a bone 280 using a bone anchor 282, as depicted in FIG. 24F.

Figure 25A:
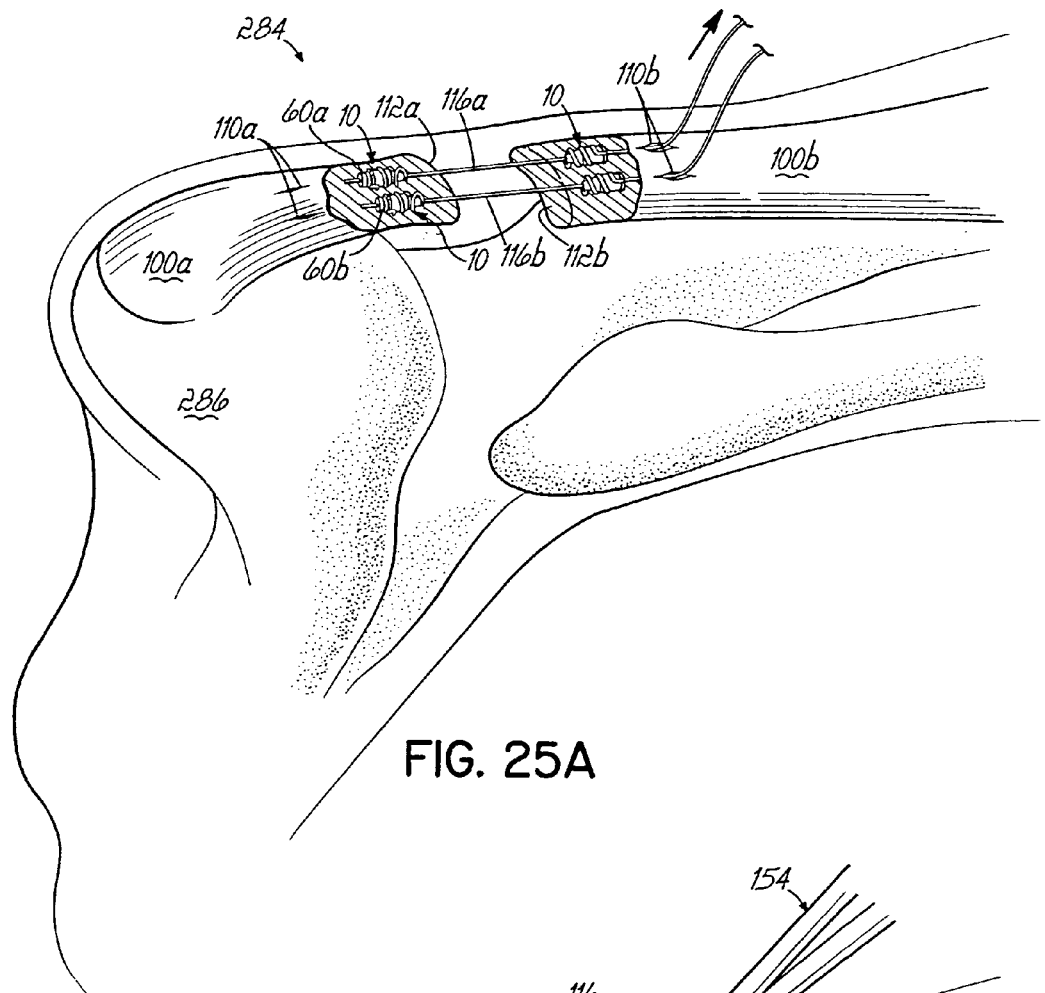
FIGS. 25A-25B are schematic illustrations depicting an exemplary method of repairing a torn Achilles tendon using exemplary apparatus of the present invention.

With reference to FIGS. 25-26, methods for repairing a torn Achilles tendon using exemplary anchor assemblies of the present invention will now be described. Referring to FIG. 25A, there is shown an Achilles tendon which has been severed such that a first tendon segment 100a, attached to the calcaneus, or heel bone, 286 has separated from a second tendon segment 100b which is connected to the gastrocnemius (not shown) of the calf muscle. In one exemplary method, the severed tendon segments 100a, 100b may be repaired by inserting first and second soft tissue anchor assemblies 10 within the first segment of the tendon 100a through incisions 110a which have been made in the surface of the tendon segment 100a and installing third and fourth soft tissue anchor assemblies 10 into the second tendon segment 100b through corresponding incisions 110b. Soft tissue anchor assemblies 10 may be inserted into the respective tendon segments 100a, 100b using, for example, any of the installation tools and methods previously described. If the tissue anchors 10 are installed using insertion tool 70, then elongate tensile members 116 may be subsequently coupled to the tissue anchors 10, such as by the method previously described with respect to FIGS. 14A-14E. If insertion tool 200 is used to install at least some of the anchor assemblies 10, these anchor assemblies will be installed with elongate tensile members 116 already coupled to them and the elongate tensile members 116 need only be coupled to corresponding anchor assemblies 10 in the other tendon segment, such as by the method described above with respect to FIGS. 14A-14E.

Figure 25B:
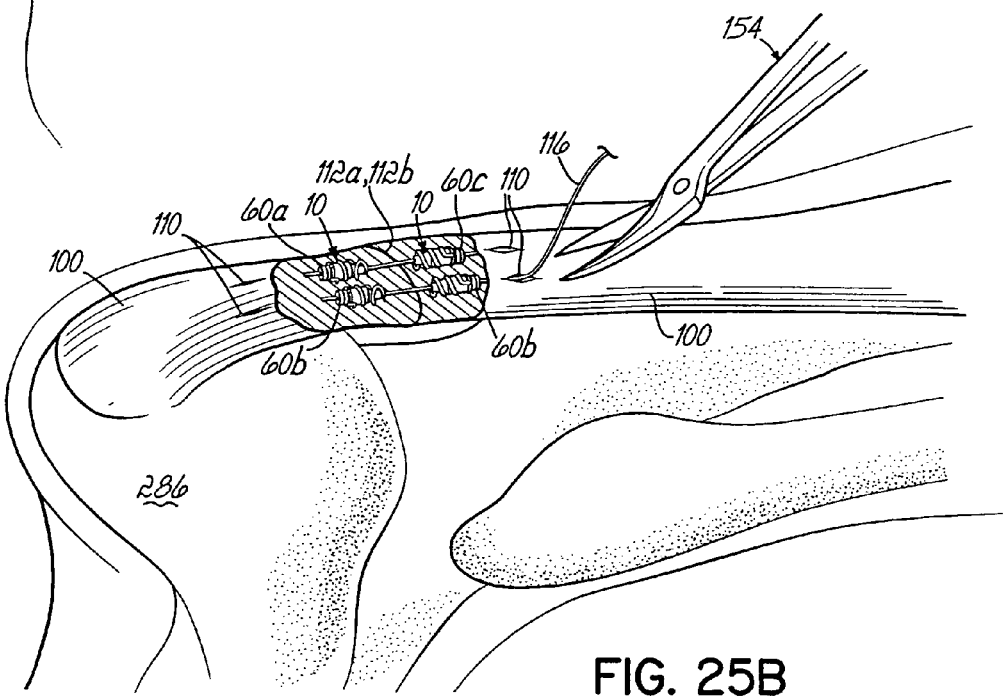

In the exemplary method illustrated in FIGS. 25A-25B, two elongate tensile members 116a, 116b are coupled to anchor assemblies 10 and are inserted within tendon segments 100a, 100b. First and second stop members 60a, 60b may be provided pre-secured to elongate tensile members 116a, 116b or they may be coupled to the elongate tensile members 116a, 116b after installation of the elongate tensile members, as previously described. After the anchor assemblies 10 and elongate tensile members 116 have been installed within the respective tendon segments 100a, 100b, the first and second elongate tensile members 116a, 116b may be tensioned to approximate the severed ends 112a, 112b of the tendon segments 100a, 100b as shown in FIG. 25B. After the tendon segments 100a, 100b have been approximated, third and fourth stop members 60a, 60b are coupled to the elongate tensile members 116a, 116b and secured to the elongate tensile members 116a, 116b using, for example, crimp tool 160 or crimp-and-cut tool 230, as previously described.

Figure 26A:
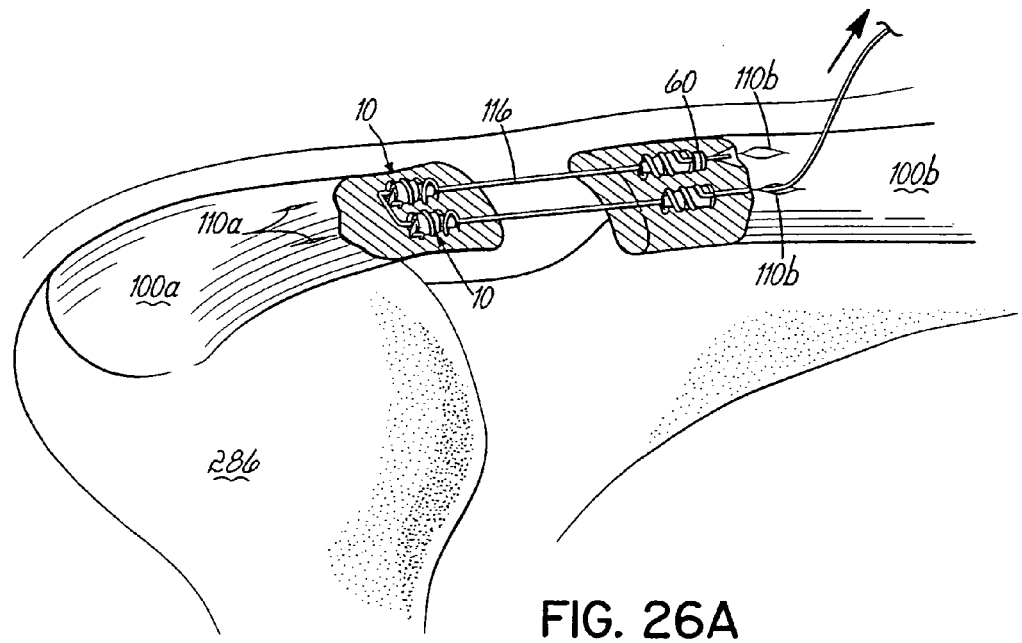
FIGS. 26A-26B are schematic illustrations depicting another exemplary method of repairing a torn Achilles tendon using exemplary apparatus of the present invention.
Figure 26B:
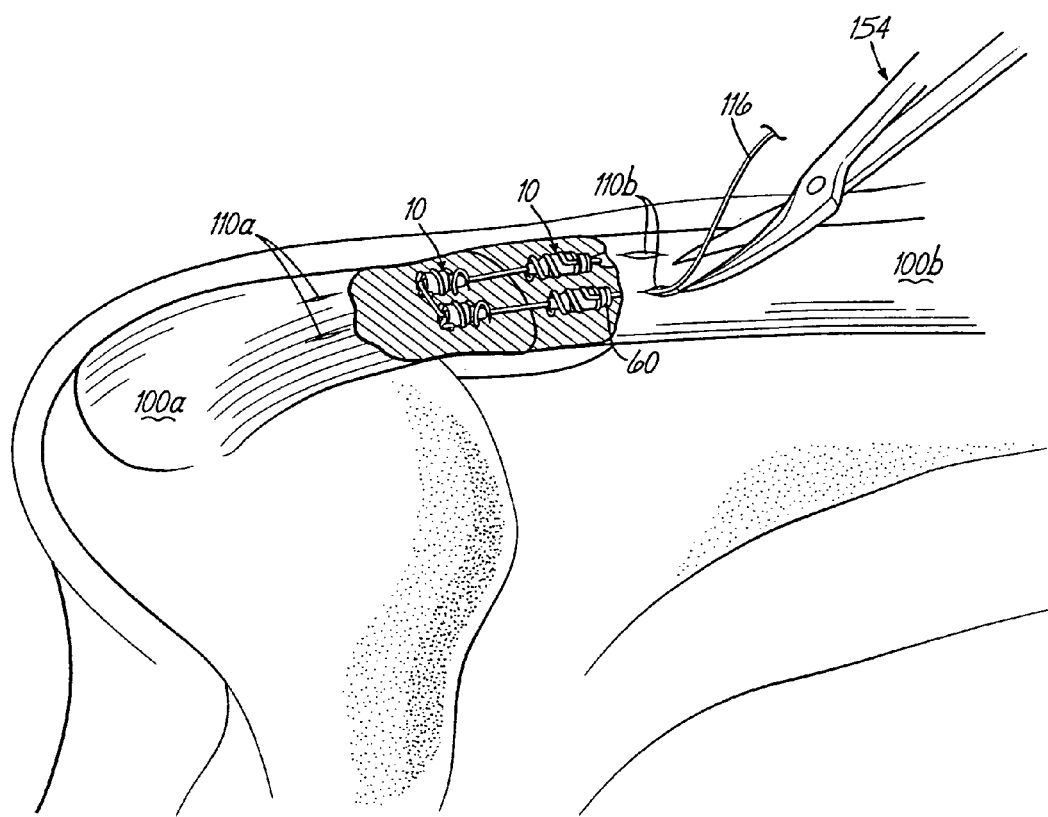

In another exemplary method, the corresponding soft tissue anchor assemblies 10 in the respective tendon segments 100a, 100b may be joined using a single elongate tensile member 116 looped through each of the anchor assemblies 10, as depicted in FIG. 26A. When the tendon segments 100a, 100b are attached using this method, the elongate tensile member 116 may be provided with a stop member 60 pre-secured to an end of the elongate tensile member 116, or the stop member 60 may be secured to the elongate tensile member 116 in situ using either crimp tool 160 or crimp-and-cut tool 230. After the elongate tensile member 116 has been coupled to each of the anchor assemblies 10, tension is applied to the elongate tensile member 116 to approximate the severed ends 112a, 112b of the tendon segments 100a, 100b, as depicted in FIG. 26B. A second stop member 60 may then be secured to the elongate tensile member 116 and the excess portion of the elongate tensile member 116 trimmed using a cutting tool 154. Alternatively, crimp-and-cut tool 230 may be used to secure the second stop member 60 and to cut the elongate tensile member 116.

While FIGS. 25 and 26 have depicted methods for repairing an Achilles tendon through incisions which have been made on the lateral sides of tendon segments 100a, 100b, it will be recognized that the soft tissue anchor assemblies 10 and elongate tensile members 116 may alternatively be inserted through the severed ends 112a, 112b of the tendon segments 100a, 100b as described above with respect to FIGS. 18A-18E. Furthermore, while the methods described above have utilized four soft tissue anchors 10, it will be recognized that a greater number or a fewer number of soft tissue anchors 10 may be used to repair an Achilles tendon, as may be desired.

The foregoing methods have focused on tendon repair between severed segments of a tendon or ligament, however, it is sometimes desired to reattach a tendon or ligament to a bone, such as during the repair of a rotator cuff. Accordingly, FIGS. 27-29 illustrate exemplary methods of attaching a ligament or tendon 100 to the humerus bone 290 during a rotator cuff repair. To attach a tendon or ligament 100 to the humerus 290 using elongate tensile members 116 and soft tissue anchor assemblies 10, the elongate tensile members 116 must be secured to the head 292 of the humerus 290. In one exemplary method, the surface of the humeral head 292 is prepared, such as by abrading the surface or forming a trough 294, using a bone burr for example, and holes 296 are drilled through a segment of the humeral head 292, as depicted in FIG. 27A.

Figure 27A:
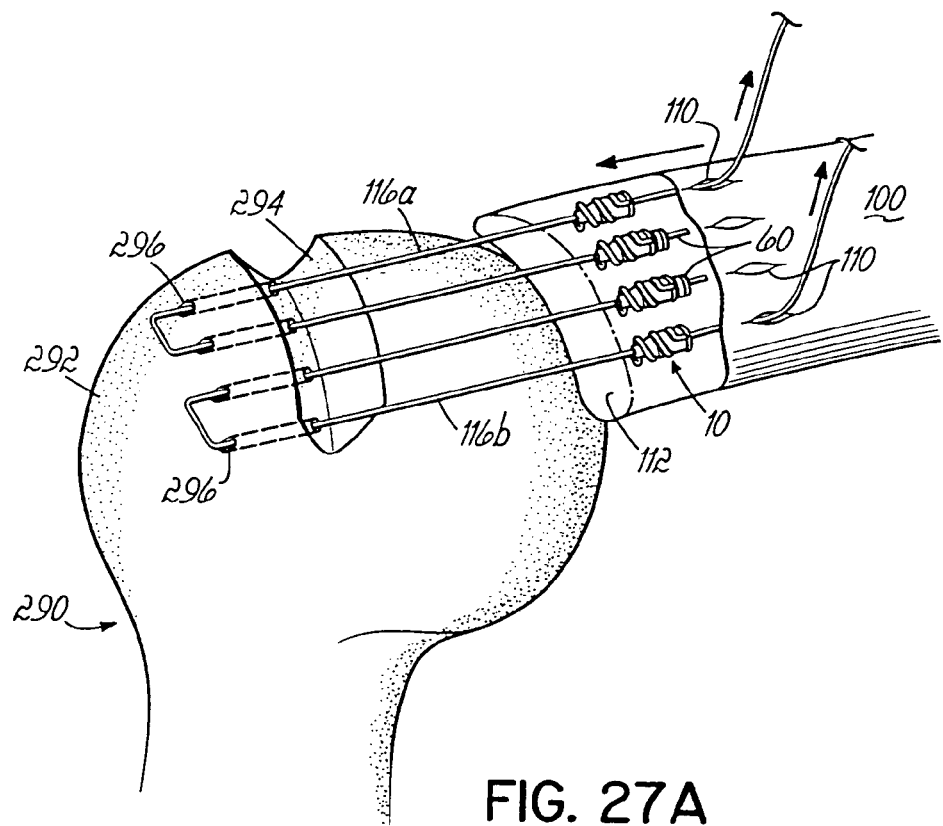
FIGS. 27A-27B are schematic illustrations depicting an exemplary method of repairing a rotator cuff using exemplary soft tissue anchors of the present invention.
Figure 27B:
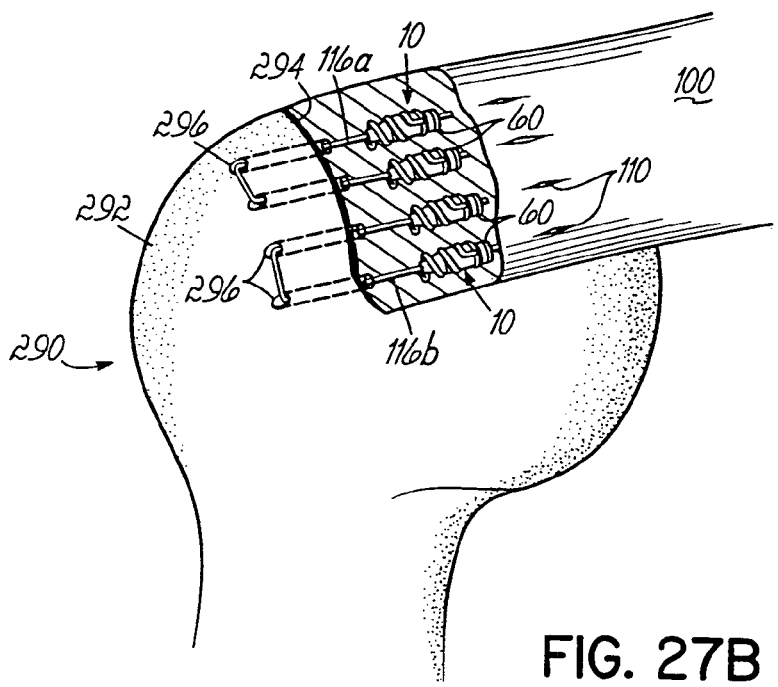

With continued reference to FIG. 27A, first, second, third and fourth soft tissue anchor assemblies 10 are inserted within the tendon or ligament 100, such as through incisions 110 formed in a surface of the tendon 100 and using an installation tool such as those previously described. Elongate tensile members 116 may either be coupled to at least some of the anchor assemblies 10 prior to installation and driven by an installation tool through the tendon 100, or elongate tensile members 116 may be coupled to the tissue anchors after installation of the anchor assemblies 10, as previously described. In the exemplary embodiment depicted in FIG. 27A, two elongate tensile members 116a, 116b are used to secure the tendon 100 to the humeral head 292 whereby each elongate tensile member 116a, 116b is coupled to two of the anchor assemblies 10, near the ends of the elongate tensile members 116a, 116b, and intermediate portions of the elongate tensile members 116a, 116b are routed through the holes 296 in the humeral head 292. The elongate tensile members 116a, 116b are tensioned to approximate the tendon 100 to the humeral head 292 such that the severed end 112 of the tendon 100 seats in the trough 294, as depicted in FIG. 27B. Stop members 60 are then secured to the free ends of elongate tensile members 116a, 116b, as previously described.

Figure 28A:
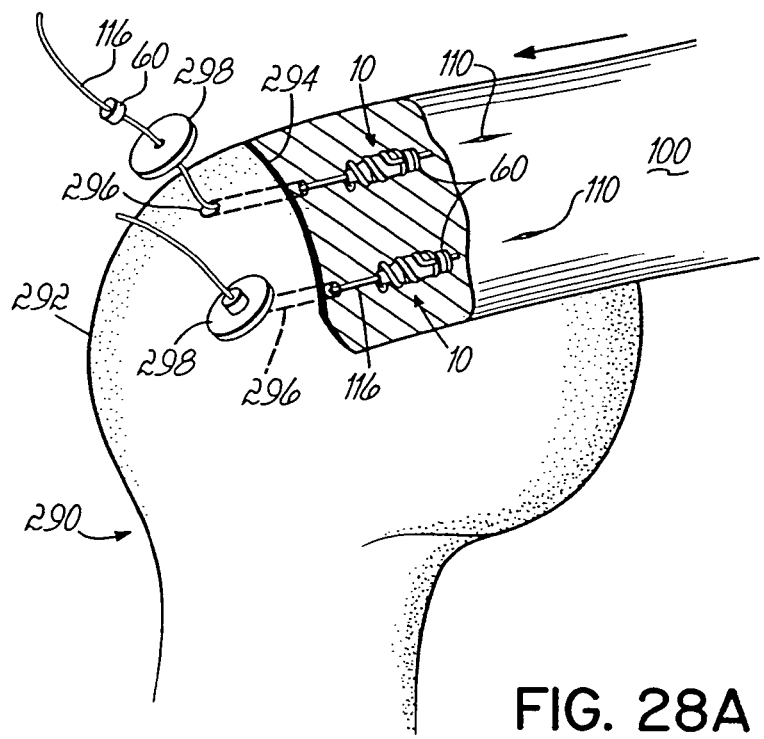
FIGS. 28A-28B are schematic illustrations depicting other exemplary methods of repairing a rotator cuff using exemplary soft tissue anchors of the present invention.
Figure 28B:
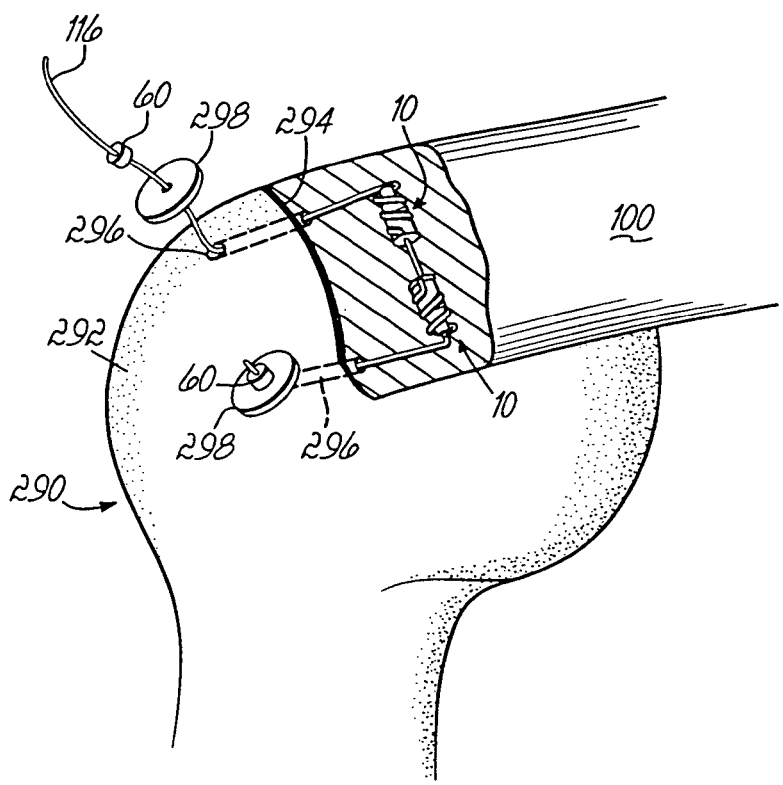

FIGS. 28A and 28B depict methods of securing a rotator cuff tendon 100 wherein the elongate tensile members 116 are secured to the humeral head 292 using stop members 60 and load distributing members, such as washers 298. Referring to FIG. 28A, two holes 296 are formed through a segment of the humeral head 292 and two soft tissue anchor assemblies 10 are inserted within the tendon 100 similar to the method described above for FIG. 27A. An elongate tensile member 116 is routed through each of the anchor assemblies 10 and through the holes 296 such that tension applied to the elongate tensile members 116 approximates the tendon 100 to the humeral head 292. Washers 298 are coupled to each of the elongate tensile members 116 and are secured to the elongate tensile members 116 using stop members 60. While the load distributing members have been illustrated and described as flat washers 298, it will be recognized that other types of load distributing members may also be used, such as Belleville washers.

In FIG. 28B, another exemplary method of securing the rotator cuff tendon 100 to the humeral head 292 comprises installing first and second soft tissue anchor assemblies 10 within the tendon 100 such that the longitudinal axes of the anchor assemblies 10 are aligned substantially transverse to the longitudinal direction of the tendon 100. A single elongate tensile member 116 is inserted within the tendon 100 and routed through both anchor assemblies 10. The ends of the elongate tensile member 116 extend from the tendon 100 and are routed through the holes 296 and secured by washers 298 and stop members 60, as described above with respect to FIG. 28A.

Figure 29A:
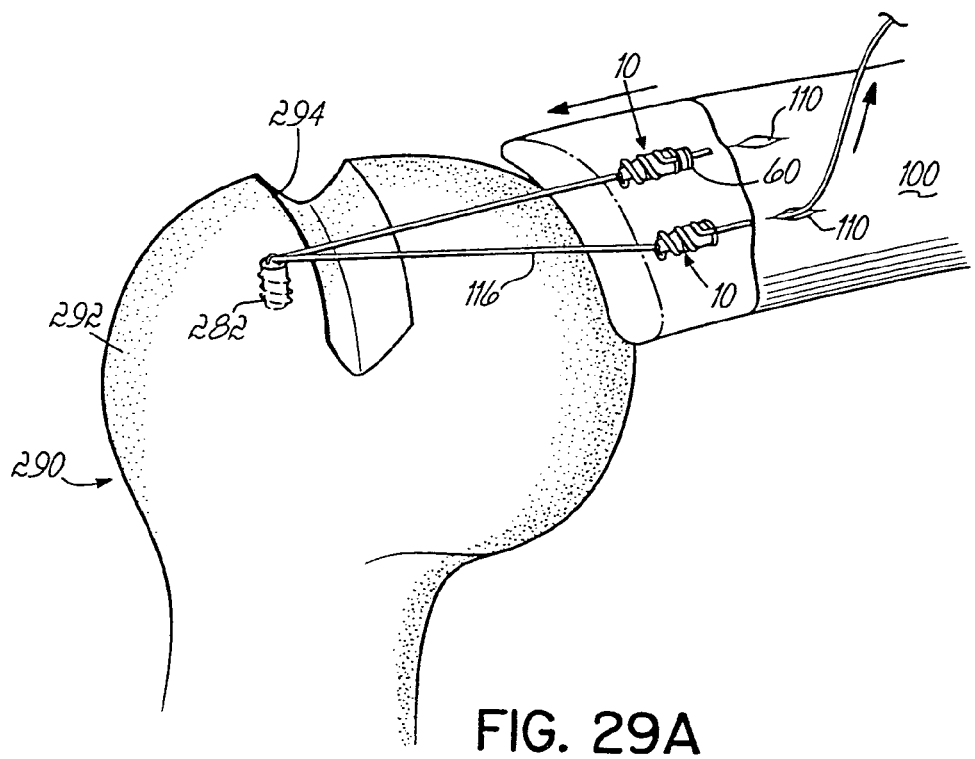
FIGS. 29A-29B are schematic illustrations depicting an exemplary method of repairing a rotator cuff using a bone anchor and exemplary soft tissue anchors of the present invention.
Figure 29B:
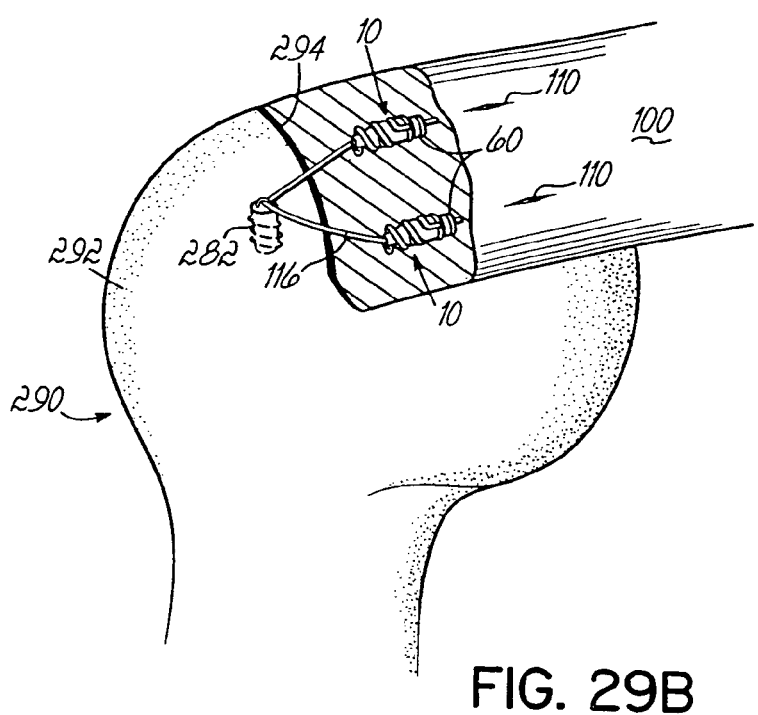

FIGS. 29A-29B illustrate another exemplary method of securing a rotator cuff tendon 100 to the humeral head 292 wherein a bone anchor 282 is installed proximate the desired attachment site, as depicted in FIG. 29A. The surface of the humeral head 292 may be prepared at the attachment site, such as by abrading the surface or forming a trough 294, as previously described. According to this method, one or more soft tissue anchor assemblies 10 are installed within the tendon 100 and at least one elongate tensile member is coupled between the bone anchor 282 and the soft tissue anchor assemblies 10. Tension is applied to the elongate tensile member 116 to approximate the tendon 100 to the attachment site and stop members 60 are secured to the elongate tensile member 116 to fix the position of the tendon 100 proximate the attachment site, as depicted in FIG. 29B. While the foregoing methods of securing a rotator cuff tendon 100 to the humeral head 292 have been described with respect to FIGS. 27-29 as utilizing specific quantities of soft tissue anchor assemblies 10, elongate tensile members 116, bone anchors 282, and other implantable devices, it will be recognized that the quantities of these implantable devices may be varied, as may be desired, to secure the tendon 100 to the humeral head 292, in the general manner described herein, without departing from the present invention.

Figure 30A:
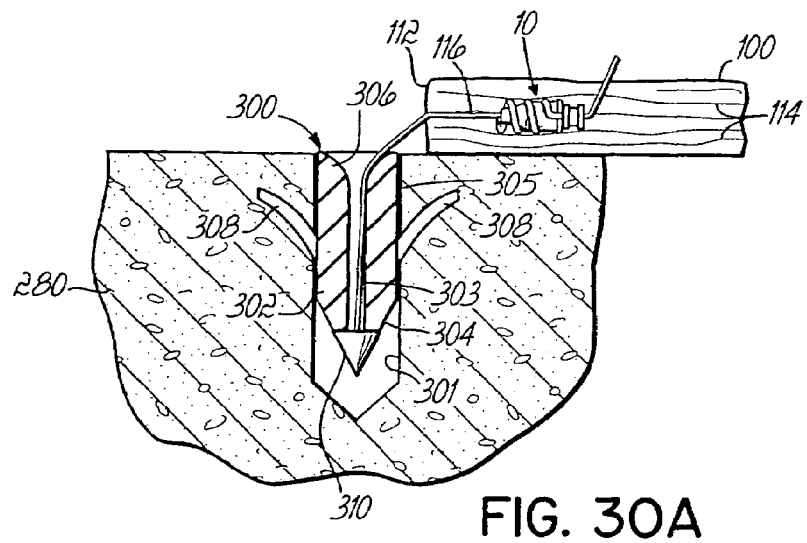
FIGS. 30A-30B are cross-sectional views depicting exemplary bone anchors of the present invention and exemplary methods for approximating a tendon or ligament to a bone using the bone anchors.
Figure 30B:
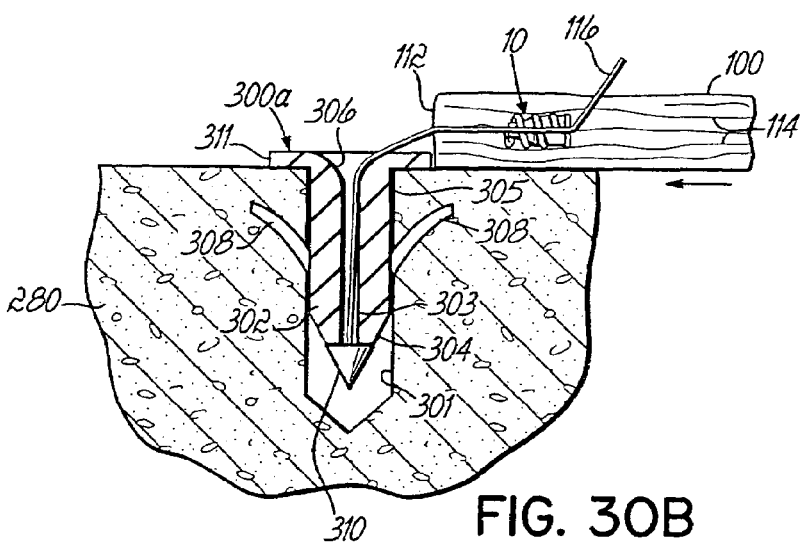
Figure 31:
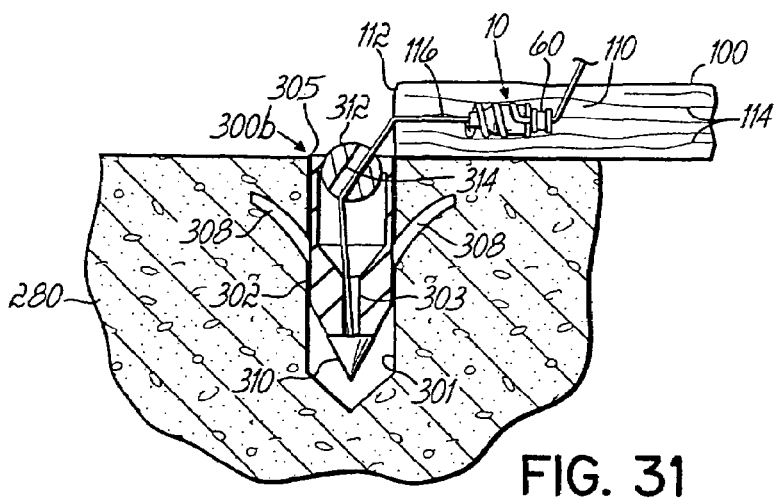
FIG. 31 is a cross-sectional view of another exemplary bone anchor of the present invention, illustrating a method of approximating a tendon or ligament to a bone using the anchor.

Referring to FIGS. 30-32, methods and apparatus for securing soft tissue to bones using bone anchors will now be described. In FIG. 30A there is shown an exemplary bone anchor 300 of the present invention. The bone anchor 300 is configured to be secured within a hole 301 which has been formed in a bone 280. The bone anchor 300 has a generally cylindrically-shaped body 302 with a tapered first end 304 and a second end 305 having a flared aperture 306. A central bore 303 extends along the body 302 between the tapered end 304 and the flared aperture 306. The bore 303 is sized to receive an elongate tensile member 116, such as a multifilament suture. The elongate tensile member 116 is secured near the tapered end 304 by a pointed tip 310 and extends through bore 303 to exit the anchor 300 through flared aperture 306. One or more lateral projections 308 extend outwardly from the body 302 and in a direction toward the flared aperture 306. The lateral projections 308 are configured to engage the cancellous bone after the anchor 300 has been inserted into the hole 301 to thereby secure the anchor within the bone 280.

Advantageously, the flared aperture 306 permits a tendon 100 to be secured substantially perpendicular to the longitudinal axis of the bone anchor 300 using an elongate tensile member 116, while protecting the elongate tensile member 116 from exposure to sharp corners which may damage the elongate tensile member 116. As further depicted in FIG. 30A, the elongate tensile member 116 may be secured at an opposite end to a tendon 100 using a soft tissue anchor, such as anchor assembly 10, or any of the soft tissue anchors described herein, and a stop member 60, as previously described.

FIG. 30B depicts another exemplary bone anchor 300a, similar to bone anchor 300 of FIG. 30A, but further including a flange 311 at second end 305 and extending radially outward from flared aperture 306. Advantageously, flange 311 helps to position bone anchor 300a at an appropriate depth within hole 301 formed into bone 280.

FIG. 31 depicts another exemplary bone anchor 300b, similar to the bone anchors 300a, 300b depicted in FIGS. 30A and 30B, but having a swivel member 312 provided at the second end 305 of the anchor 300b. The elongate tensile member 116 extends through a bore 314 in the swivel member 312, whereby a tendon or ligament 100 may be attached substantially perpendicular to the longitudinal axis of the bone anchor 300b without damaging the elongate tensile member 116. Specifically, swivel member 312 accommodates orientation of the elongate tensile member 116 between the bone anchor 300b and the tendon or ligament 100, and may also permit movement of the tendon or ligament 100 without exposing elongate tensile member 116 to sharp edges.

Figure 32A:
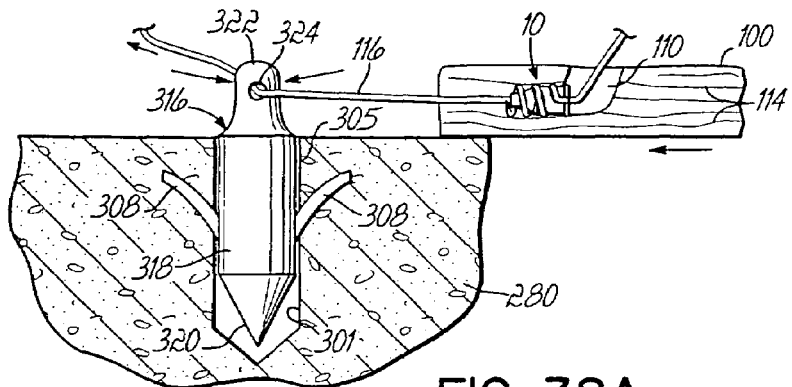
FIGS. 32A-32B is a schematic illustration depicting yet another bone anchor of the present invention, and an exemplary method of using the bone anchor to approximate a tendon or ligament to a bone.
Figure 32B:
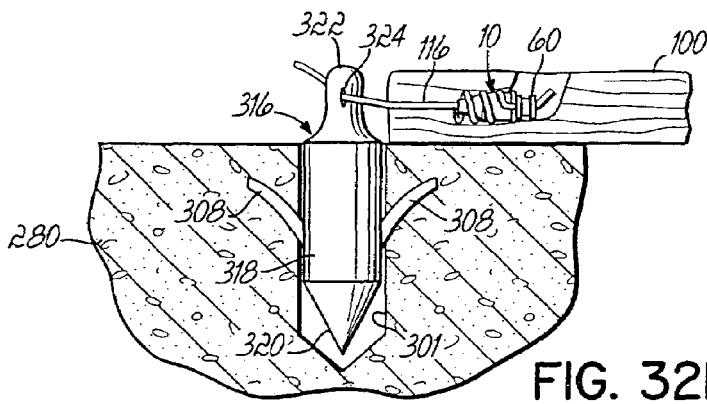

Referring now to FIGS. 32A and 32B, there is shown yet another exemplary bone anchor 316 of the present invention. Bone anchor 316 is similar to the bone anchors 300, 300a, 300b depicted in FIGS. 30 and 31. The anchor 316 has a generally cylindrically-shaped body 318 with a first end having a pointed tip 320. Lateral projections 308 extend outwardly from the body 318 to engage the cancellous bone 280 after the anchor 316 has been inserted into a hole 301 in the bone 280. A second end 305 of the bone anchor 316, opposite the pointed tip 320, includes a crimp member 322 having an aperture 324 sized to receive an elongate tensile member 116 therethrough. As depicted in FIG. 32B, the crimp member 322 may be crimped to secure the elongate tensile member 116 within the aperture 324 after elongate tensile member has been tensioned to approximate the tendon or ligament 100 to a desired position adjacent the bone anchor 316.

Figure 32C:
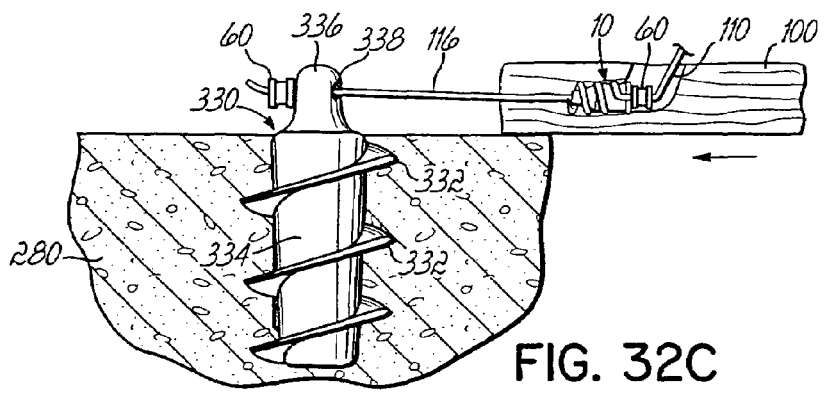
FIG. 32C is a schematic illustration of another exemplary bone anchor of the present invention, having screw threads for attachment to a bone.

FIG. 32C depicts another exemplary bone anchor 330 and a method for securing a tendon or ligament 100 to a bone 280. In this embodiment, a bone anchor 330 includes lateral projections in the form of screw threads 332 disposed along a generally cylindrical body 334. The bone anchor 330 further includes a projection 336 which preferably extends beyond the surface of the bone 280 and has an aperture 338 sized to receive an elongate tensile member 116 therethrough. After the elongate tensile member 116 has been tensioned to position the tendon or ligament 100 at a desired location adjacent the bone anchor 330, a stop member 60 may be secured to the elongate tensile member 116 to attach the tendon or ligament 100. The opposite end of the elongate tensile member is secured to the tendon or ligament 100 using a soft tissue anchor, such as anchor assembly 10, or any of the soft tissue anchors described herein, and a stop member 60, as previously described.

Figure 32D:
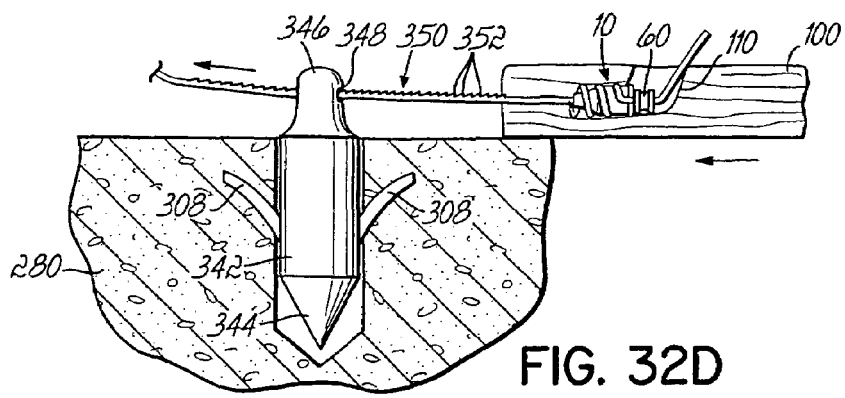
FIG. 32D is a schematic illustration depicting yet another exemplary bone anchor of the present invention, configured to be secured to a tensile member having a series of teeth disposed along its length.

FIG. 32D depicts yet another exemplary bone anchor 340 having a generally cylindrical body 342 and a pointed tip 344. Lateral projections 308 extend outwardly from the cylindrical body 342 to engage the cancellous bone 280 as previously described. The anchor 340 further includes a projection 346 having an aperture 348 configured to receive elongate tensile member 350 that has a series of serrations 352 or other similarly contoured surface along its length, whereby engagement of the serrations 352 with the aperture 348 secures the elongate tensile member 350 to the bone anchor 340. The opposite end of the elongate tensile member 352 may be secured to a tendon or ligament 100, using a soft tissue anchor assembly 10, or any other soft tissue anchor such as those described herein, and a stop member 60, in a manner similar to that previously described with respect to elongate tensile member 116.

While the projections are depicted in the figures as elongate members and screw threads, the projections may alternatively be barbs, screw threads, spikes, or other structure which is capable of engaging the bone 280 upon insertion into the hole 301, or after insertion.

Referring to FIG. 33, there is shown another exemplary anchor 360 of the present invention which is configured to attach a soft tissue directly to a hard tissue. The anchor 360 has a first portion 362 figured to engage hard tissue, such as bone, and a second portion 364 configured to engage soft tissue. The first portion 362 includes an elongate shaft 366 having screw threads 368 disposed along its length and configured to bore into hard tissue to securely attach the anchor 360 within the hard tissue. Alternatively, a plurality of barbs (not shown) may be disposed along shaft 366 to permit secure attachment of the anchor 360 within the hard tissue. The second portion 364 of anchor 360 comprises a soft tissue anchor assembly similar to the anchor assembly 10 of FIGS. 1 and 2, wherein the second portion 364 includes a helical anchor 370 and a retaining member 372. Second portion 364 further includes a slot 373 formed into proximal end 374 and configured to engage a drive tool, whereby the anchor 360 may be driven into hard tissue. Other features of the second portion 364 are similar to the anchor assembly 10 of FIGS. 1 and 2. As depicted in FIG. 33, the pitch P1 of the first portion 362 of the anchor 360 is greater than the pitch P2 of the second portion 364 to allow soft tissue engaged by the second portion 364 to be compressed while the anchor 360 is being screwed into hard tissue.

FIG. 34 depicts a top section view of a shoulder joint and illustrates an exemplary use of the anchor 360 to stabilize the shoulder. The anchor 360 is inserted into the scapula 380 near the glenoid socket 382 and through the glenoid labrum 384 to reattach the labrum 384 to near glenoid socket 382.

FIGS. 35A-35C illustrate another apparatus 390 which may be used to reattach the glenoid labrum 384 to the glenoid socket 382. With reference to FIG. 35A, the apparatus 390 includes a flexible cable 392 having a tip 394 which is adapted to bore through bone and tissue as the cable 392 is rotated about its longitudinal axis. Advantageously, the apparatus 390 may be used to install the cable 392 through the glenoid socket 382, from a position inside the shoulder capsule, and subsequently through the glenoid labrum 384 as depicted in FIG. 35B. Once the cable 392 has been extended through the glenoid labrum 384, a soft tissue anchor, such as anchor assembly 10 or any other soft tissue anchor described herein, may be coupled to the cable 392 and inserted into the glenoid labrum 384 to be secured with a stop member 60 according to methods previously described. The opposite end of the cable 392 which extends through the glenoid socket 382 may be secured using a load distributing member, such as washer 396, having a crimpable portion 396a. Alternatively, a flat washer 298 and stop member 60 may be used to secure cable 392 in a manner similar to that depicted in FIGS. 28A-28B. Other types of load distributing members may be used as well.

In an exemplary embodiment, cable 392 is configured to have elasticity in the longitudinal direction, whereby cable 392 may be tensioned to compress the glenoid labrum 384 against the glenoid socket 382 with a desired spring force. Alternatively, a relatively inextensible cable 392 may be coupled with a spring element, such as a Belleville washer 397, to create a desired spring force, as depicted in FIG. 35C. In this embodiment, Belleville washer 397 may be secured to the end of the cable 392 using, for example, a stop member 60.

Figure 36:
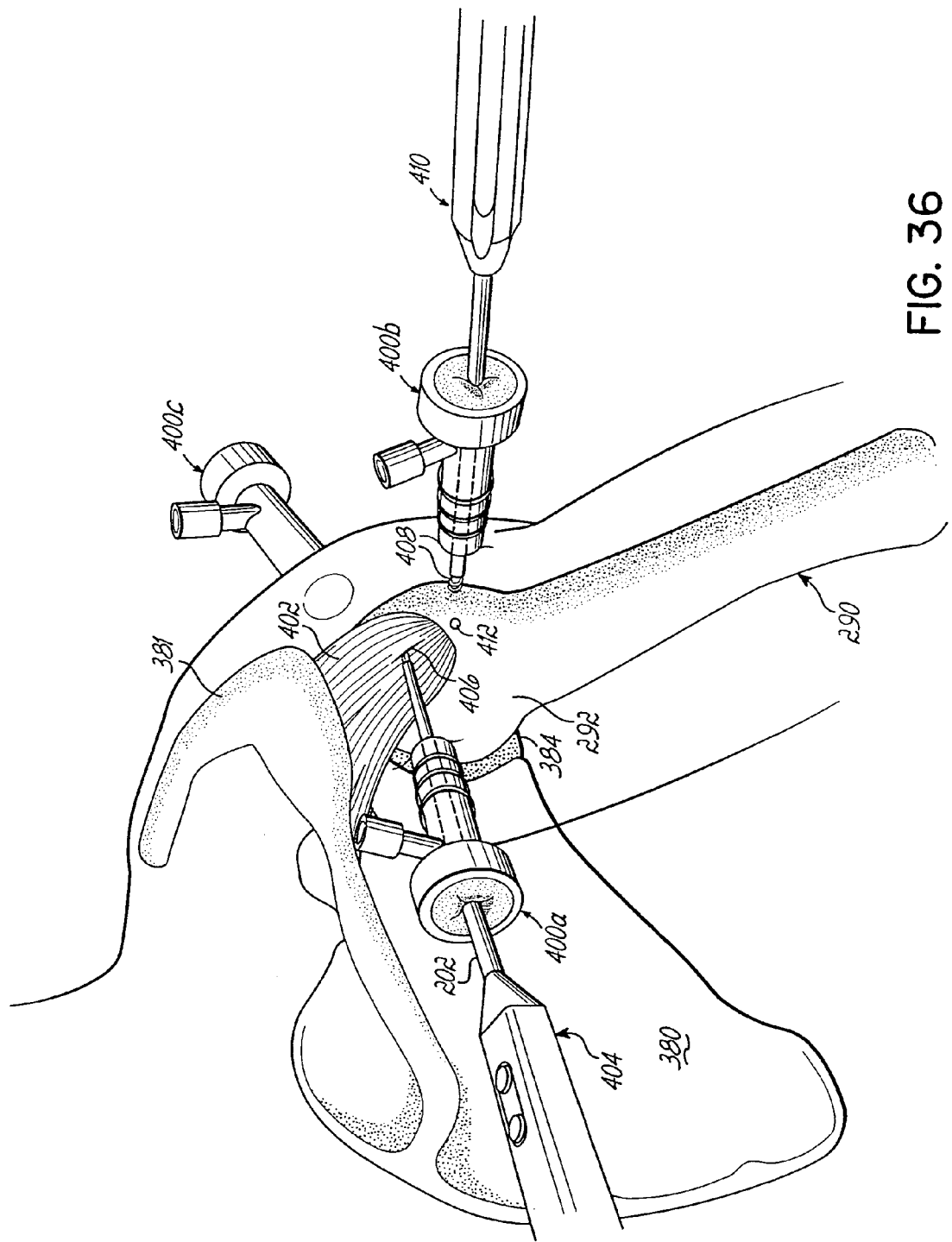
FIG. 36 is a schematic illustration depicting the repair of rotator cuff according to an exemplary method of the present invention.
Figure 37:
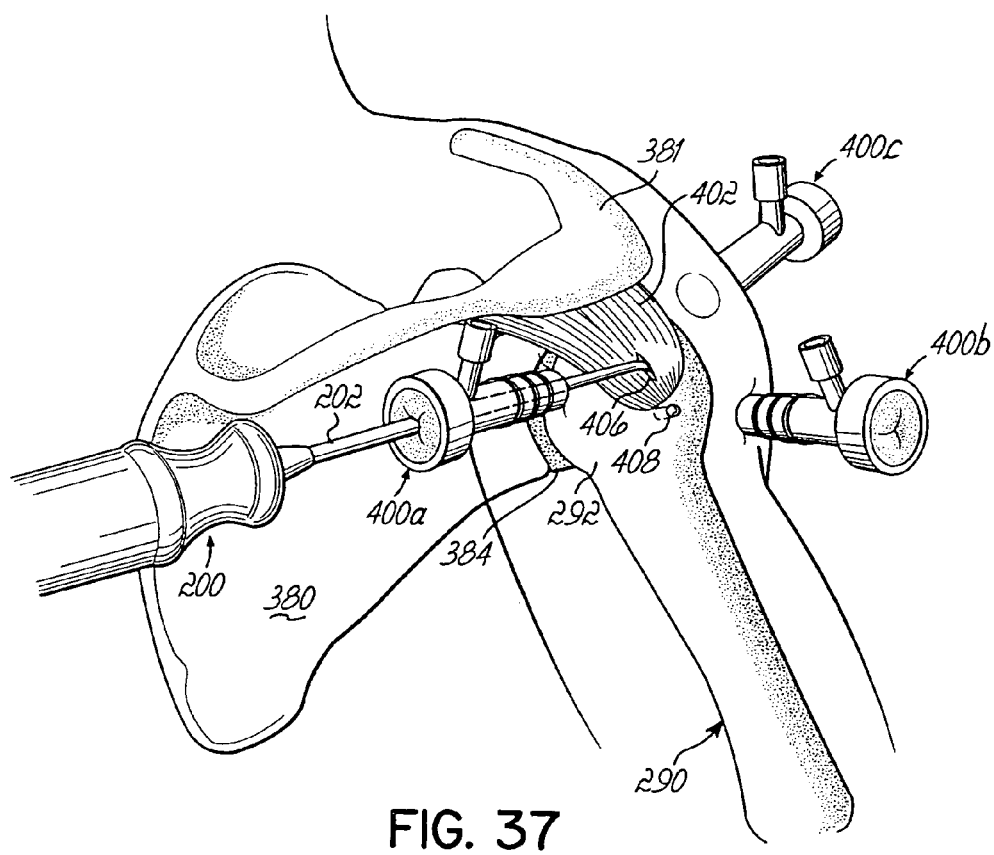
FIG. 37 is a schematic illustration depicting the tool of FIG. 19 being used to install a soft tissue anchor, according to the exemplary method of rotator cuff repair.
Figure 38:
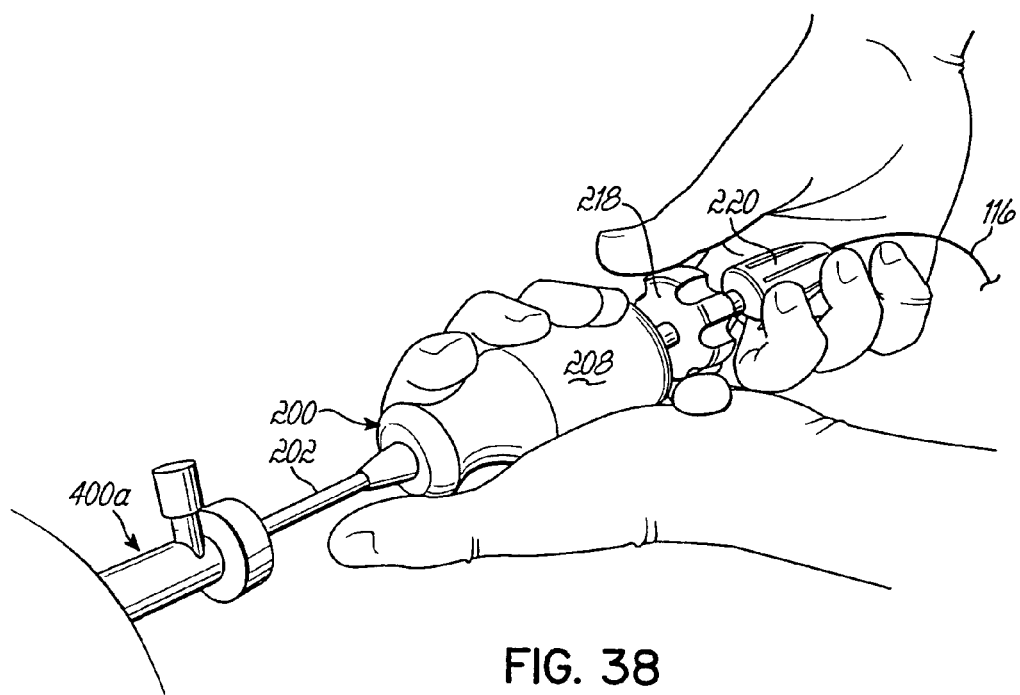
FIG. 38-39 are perspective views further illustrating use of the tool of FIG. 19 according to the exemplary method of rotator cuff repair.

With reference to FIGS. 36-46, a method of reattaching a rotator cuff ligament 402 to the humeral head 292 of the humerus 290 will now be described. In preparation for repairing a torn rotator cuff, one or more cannulas 400a, 400b, 400c may be inserted into the shoulder of a patient near the humeral head 292 of the humerus bone 290, as depicted in FIG. 36. While the method below is described with respect to using cannulas, it will be recognized that the attending surgeon may alternatively reattach the rotator duff ligament 402 through incisions at appropriate locations without using cannulas and in a manner similar to that herein described. FIG. 36 also illustrates relevant anatomy of the patient, such as the scapula 380, the acromium 381 and the glenoid labrum 384. To reattach the rotator cuff tendon 402 to the humeral head 292, a scalpel 404, or any other cutting device, such as an electro-surgical cutting device, is inserted through a first cannula 400a and is used to make an incision, or tenotomy, 406 at a location where it is desired to install a soft tissue anchor. A bone anchor 408, which may be a conventional bone anchor or any of the bone anchors described herein, is inserted through a second cannula 400b and is installed to a pre-drilled hole 412 using a bone anchor installation tool 410. After the incision 406 has been made in the rotator cuff tendon 402, a soft tissue anchor assembly may be installed within the tendon 402 using installation tool 200 inserted through the first cannula 400a as depicted in FIG. 37. As illustrated in FIG. 38, the attending surgeon manipulates first knob 218 of tool 200 to rotate the soft tissue anchor assembly (not shown) while advancing the anchor assembly into the tendon 402, as was previously described with respect to FIGS. 20A-20B.

Figure 39:
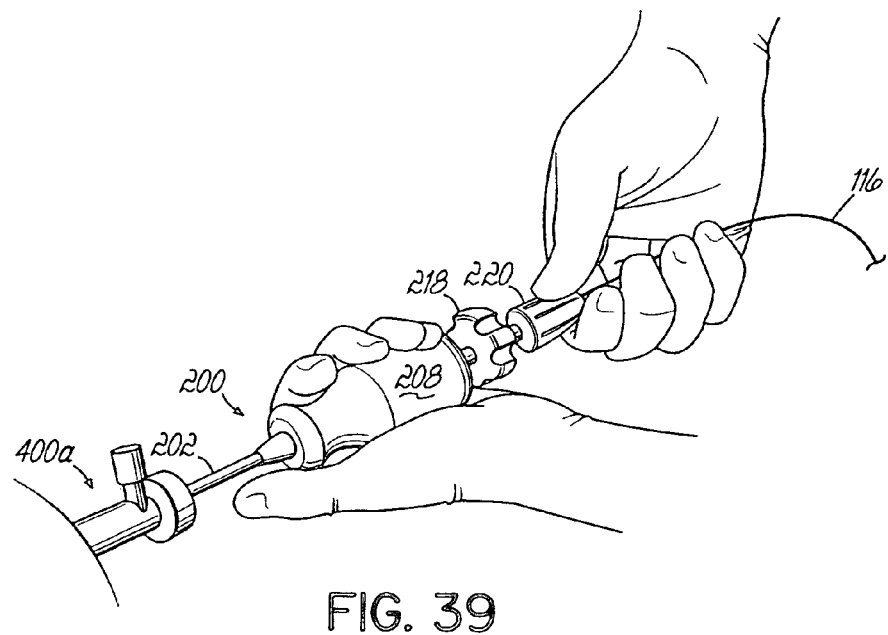
Figure 40:
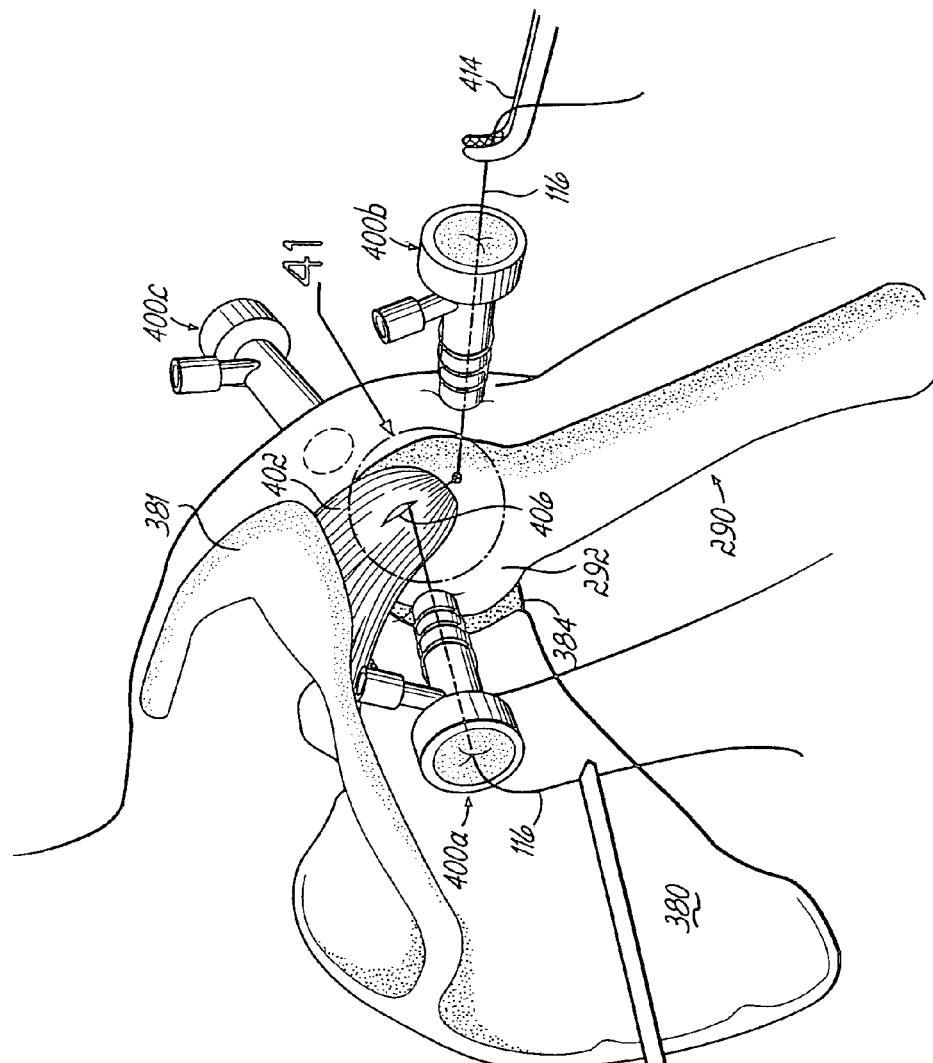
FIG. 40 is a schematic illustration further depicting the exemplary method of rotator cuff repair and use of the tool of FIG. 21 to secure a stop member to a tensile member according to the method.
Figure 41:
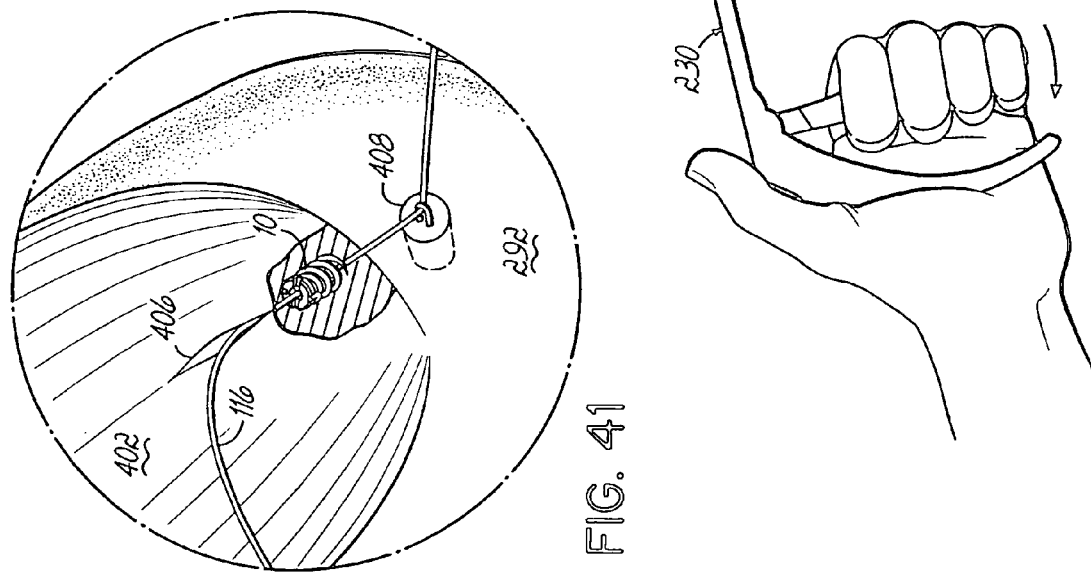
FIG. 41 is an enlarged detail view of the repair site FIG. 40, illustrating the routing of a tensile member through a bone anchor and tissue anchor, according to the exemplary method.

After the soft tissue anchor assembly has been secured within the tendon 402, the attending surgeon may then manipulate the second knob 220 of the installation tool 200 to advance an elongate tensile member 116, such as a multi-filament suture, through the tendon 402 as illustrated in FIG. 39 and previously described with respect to FIG. 20C. Stop member 60 may be applied to the elongate tensile member 116 by the attending surgeon using, for example, the crimp-and-cut tool 230, previously described above, as illustrated in FIG. 40. The elongate tensile member 116 is routed from the end of the tendon 402 to couple with the bone anchor 408 and is pulled out through the second cannula 400b using forceps 414 or any other appropriate tool as illustrated in FIGS. 40 and 41.

Once the elongate tensile member 116 has been routed through second cannula 400b, it may then be drawn tight to approximate the tendon 402 to a desired location adjacent the bone anchor 408 and a second stop member 60 may be applied to the elongate tensile member 116 using, for example, the cut-and-crimp installation tool 230 as illustrated in FIGS. 42 and 43. As shown in FIG. 43, the tendon 402 is thus fixed to the humeral head 292 in a secure attachment which utilizes the natural strength of the collagen fibers of the tendon 402 while minimizing the amount of foreign material external to the tendon 402 at the repair site.

Figure 44A:
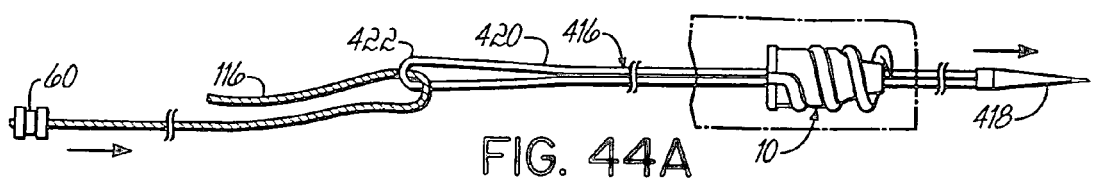
FIGS. 44A-44B are schematic illustrations depicting another exemplary method for repairing a rotator cuff, wherein a tensile member is routed through a bone anchor and a tissue anchor using a shuttle suture.
Figure 44B:
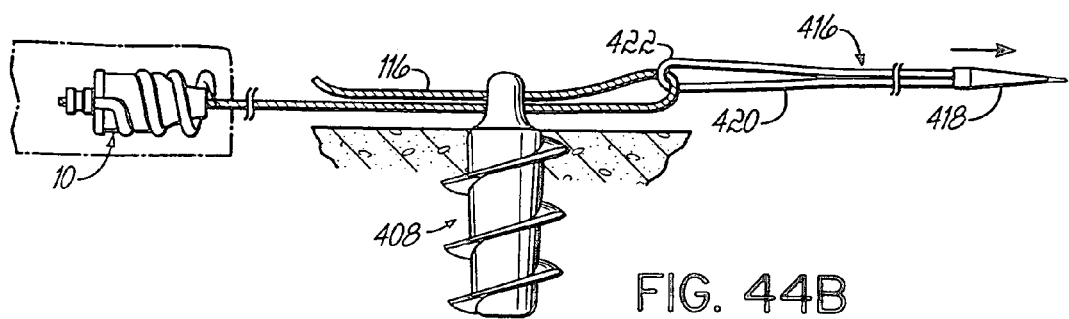
Figure 45:
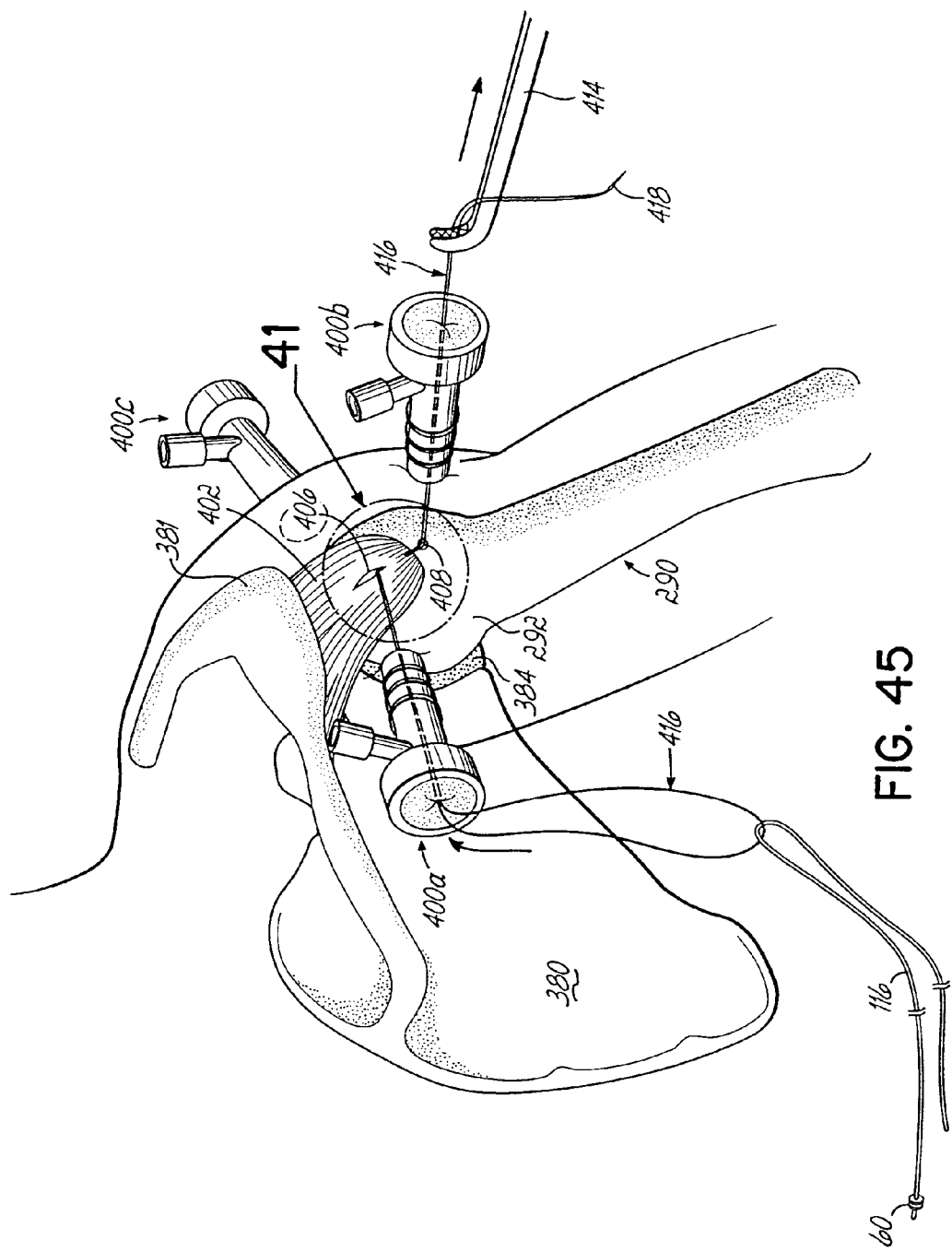
FIG. 45 is a schematic illustration further depicting use of the shuttle suture of FIGS. 44A-44B to route the tensile member according to the exemplary method.
Figure 46:
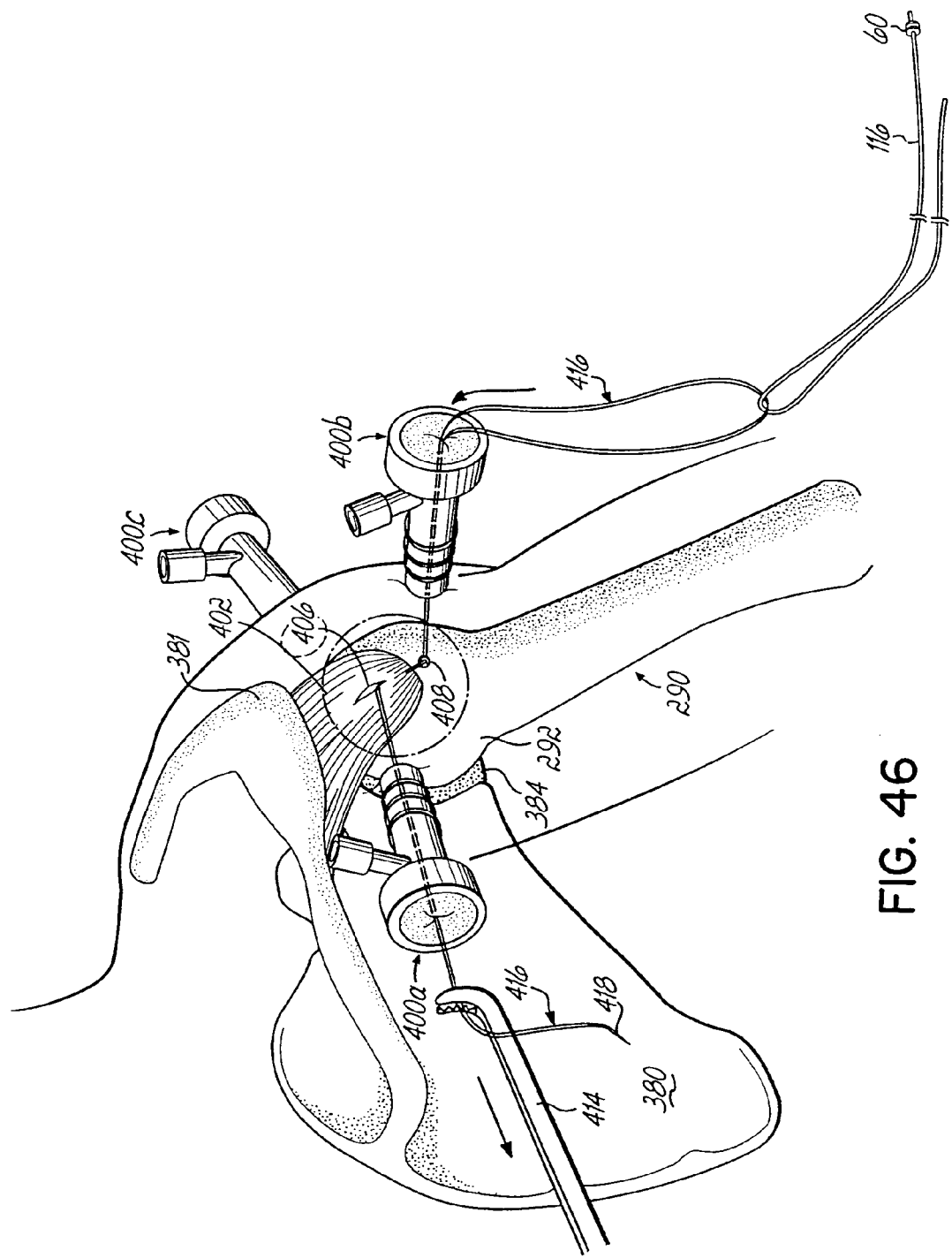
FIG. 46 is a schematic illustration depicting yet another method of using a shuttle suture to route a tensile member during a rotator cuff repair.

While elongate tensile member 116 may be coupled to anchor assembly 10 prior to installation of the tissue anchor 10 into the tendon 402 and subsequently routed through bone anchor 408 as described above with respect to FIGS. 40 and 41, elongate tensile member 116 may alternatively be routed through the soft tissue anchor 10 and bone anchor 408 using a shuttle suture 416 which has been coupled to the soft tissue anchor 10 and installed, for example, using installation tool 200 as previously described with respect to FIGS. 37-39. As illustrated in FIG. 44A, shuttle suture 416 includes a needle tip 418 and a flexible suture member 420. The shuttle suture 416 is configured to have a loop 422 through which one end of the elongate tensile member 116 may be inserted. After the shuttle suture 416 has been driven through tendon 402 and routed through bone anchor 408, it is withdrawn through the second cannula 400b to shuttle the elongate tensile member 116 through the first cannula 400a, the soft tissue anchor (FIG. 41), the bone anchor 408 (see FIG. 44B), and the second cannula 400b using forceps 414, as illustrated in FIG. 45. Alternatively, shuttle suture 416 may be routed in the opposite direction, entering through second cannula 400b and being withdrawn from first cannula 400a, as depicted in FIG. 46.

While the foregoing methods have been described with regard to the installation of a single soft tissue anchor assembly 10 of the present invention, it will be recognized that more than one anchor assembly 10 may be installed into the tendon 402 to affect the repair. For example, FIGS. 47A and 47B illustrate two alternative configurations wherein two anchor assemblies 10 may be inserted into a tendon 402 and coupled to a single bone anchor 408. In FIG. 47A, each anchor assembly 10 is coupled to the bone anchor 408 using a separate elongate tensile member 116. In FIG. 47B, two anchor assemblies 10 are coupled to a bone anchor 408 using a common elongate tensile member 116. In a similar fashion, it will be recognized that a single soft tissue anchor assembly 10 may be coupled to two or more bone anchors 408 to affect a tendon repair. Furthermore, it will be recognized that, in certain instances, the various steps of methods described herein may be performed in orders other than those described. Accordingly, the methods are not limited to being performed in any particular order of steps.

Figure 48:
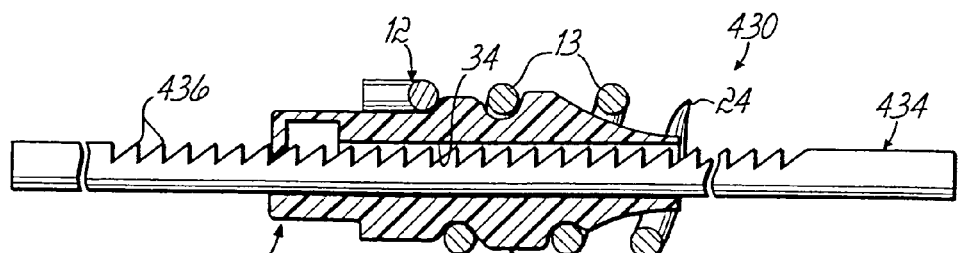
FIGS. 48-50 are a partial section views depicting other exemplary soft tissue anchors of the present invention.
Figure 49:
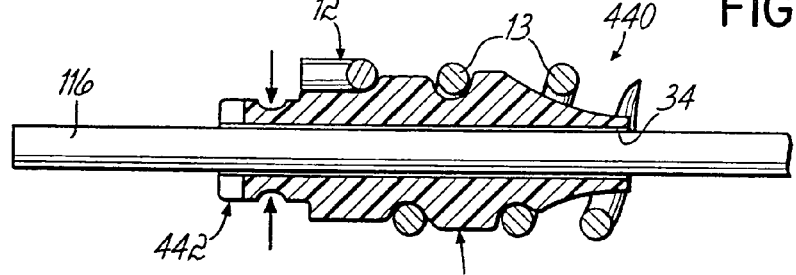

Referring now to FIGS. 48 and 49, there are shown exemplary soft tissue anchor assemblies similar to the anchor assembly 10 of FIGS. 1 and 2, wherein the anchor assemblies are further configured to be secured to an elongate tensile member and wherein like components are similarly numbered. In FIG. 48, there is shown an exemplary soft tissue anchor assembly 430 having a stop member 432 integral with the retaining member 146 and configured to engage a contoured surface of an elongate tensile member 434, which may be coupled to the anchor assembly 430. In the exemplary embodiment shown, the contour of elongate tensile member 434 includes a series of serrations 436 and integral stop member 432 is configured to engage the serrations 436 to securely fix the anchor assembly 430 to the elongate tensile member 434.

In FIG. 49, there is shown an exemplary soft tissue anchor assembly 440 wherein the retaining member 14c includes an integral stop member 442 which is configured to be secured to an elongate tensile member 116 by crimping the integral stop member 442 in a manner similar to the crimping of stop members 60 previously described.

Figure 50:
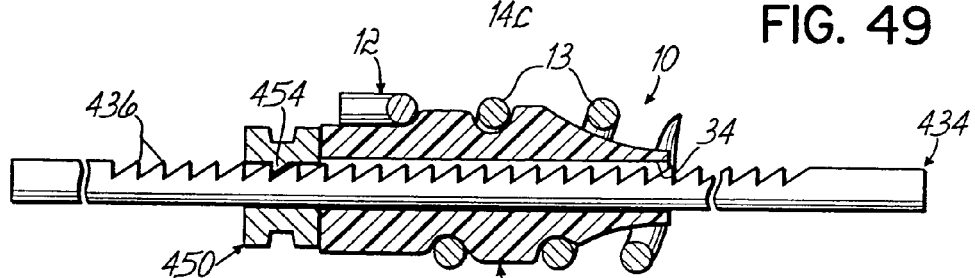

Referring to FIG. 50, there is shown yet another exemplary apparatus for repairing a tendon or ligament. The apparatus includes a soft tissue anchor assembly 10, as depicted in FIGS. 1 and 2, and a stop member 450 which may be secured to a contoured surface of an elongate tensile member 434. In the exemplary embodiment shown, the stop member 450 is similar to the stop member 60 previously described, and further includes an integral engagement member 454 configured to engage serrations 436 in the elongate tensile member 434 to thereby secure the stop member 450 to the elongate tensile member 434.

Figure 51:
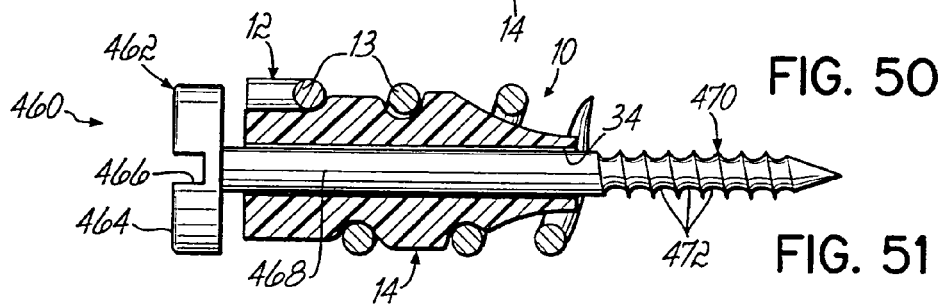
FIG. 51 is a partial section view depicting another exemplary anchor of the present invention configured to secure soft tissue to bone.

Referring now to FIG. 51, there is shown an exemplary anchor assembly 460 for attaching soft tissue to bone. The anchor assembly 460 is similar to the anchor assembly 360 of FIG. 33 and includes first and second portions which may be coupled together to form the anchor assembly 460. The first portion 462 includes an elongate shaft 468 having an enlarged head 464 at one end and bone engaging structure 470 at an opposite end. The enlarged head 464 includes a slot 466 for receiving a drive tool which facilitates installation of the anchor assembly 460. In the exemplary embodiment shown, the bone engaging structure 470 includes screw threads 472, but may alternatively include other structure for engaging the bone, such as barbs (not shown) extending outwardly from the shaft 468. The second portion of the anchor assembly 460 comprises a soft tissue anchor 10, previously described with respect to FIGS. 1 and 2. As shown in FIG. 51, the first portion 462 may be coupled to the anchor assembly 10 such as through bore 34 in anchor assembly 10. Advantageously, the anchor assembly 460 may be used to secure soft tissue to a bone in a manner similar to that described for anchor assembly 360 of FIG. 33.

Figure 52A:
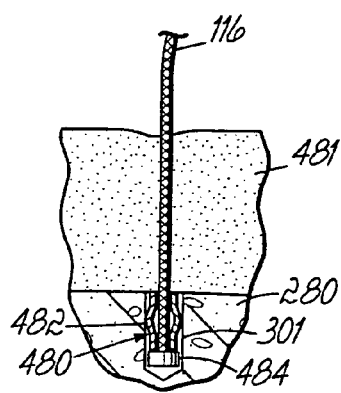
FIGS. 52A-52C are schematic illustrations depicting another exemplary apparatus and method for securing soft tissue to bone and including an expandable bone anchor.
Figure 52B:
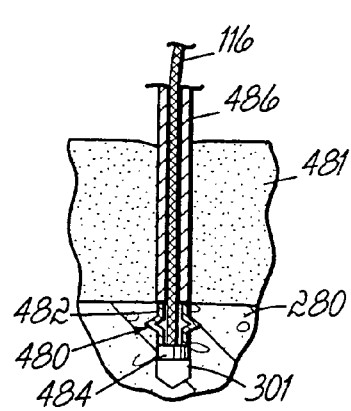
Figure 52C:
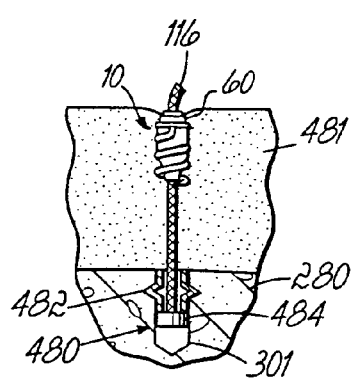
Figure 53:
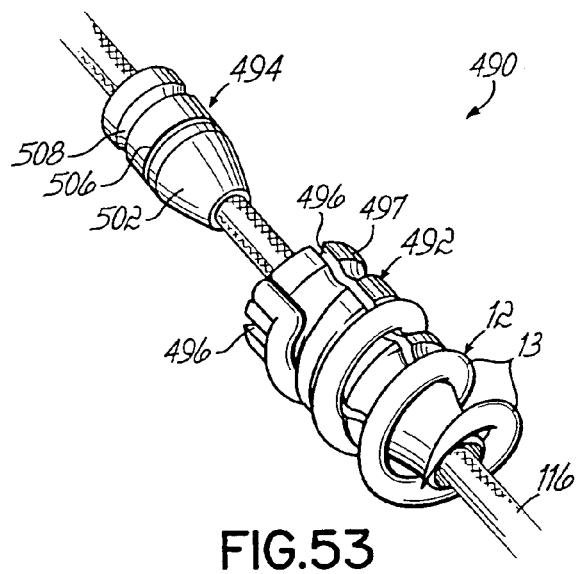
FIG. 53 is a perspective view of yet another exemplary apparatus of the present invention, including a soft tissue anchor having an expandable retaining member.

FIGS. 52A-52C illustrate another apparatus for securing soft tissue to a bone. As shown in FIG. 52A, the apparatus includes a bone anchor 480 which may be inserted into a cavity, such as a drilled hole 301, formed in a bone 280. The bone anchor assembly 480 includes a collapsible member 482 which is configured to expand in a direction substantially normal to a lengthwise direction of the member to thereby securely engage the anchor assembly 480 to the bone 280. In the embodiments illustrated in FIGS. 52A and 52B, the collapsible member 482 is made up of one or more buckling elements which extend outwardly to engage the bone 280 as the anchor assembly 480 is collapsed along its lengthwise direction. The apparatus further includes an elongate tensile member 116 coupled to the bone anchor assembly 480 such as by an end member 484 integral with said collapsible member 482. Alternatively, end member 484 may be secured to elongate tensile member 116 to abut collapsible member 482 as tension is applied to elongate tensile member 116. To facilitate expanding collapsible member 482, an actuating member, such as a tube 486 installed over elongate tensile member 116, may be inserted through the soft tissue 481 to abut the anchor assembly 480 while tension is applied to elongate tensile member 116 to collapse the collapsible member 482. As illustrated in FIG. 52C, the elongate tensile member may be secured to the soft tissue 481 using, for example, a soft tissue anchor 10 and a stop member 60, as previously described.

With reference to FIGS. 53 and 54A-54C, there is shown another exemplary soft tissue anchor assembly 490 similar to the anchor assembly 10 of FIGS. 1 and 2, and including an expandable retaining member 492. The retaining member 492 is coupled to a helical anchor 12 in the manner previously described, whereby the retaining member and helical anchor may be simultaneously driven into a tendon or ligament to receive fibers of the tendon or ligament between the helical anchor 12 and the retaining member 492. An expansion member 494 is configured to engage the retaining member 492 to thereby expand the retaining member to grip the fibers of the tendon or ligament between the helical anchor 12 and the retaining member 492. In the exemplary embodiment shown, retaining member 492 includes one or more slots 496 formed longitudinally along the retaining member 492 to separate the retaining member 492 into outwardly expandable portions 497. As shown most clearly in FIGS. 54A and 54B, retaining member 492 further includes a bore 34 extending through the retaining member and sized to receive an elongate tensile member 116 therethrough. The retaining member 492 further includes an aperture 498 which is configured to receive expansion member 494.

Figure 54A:
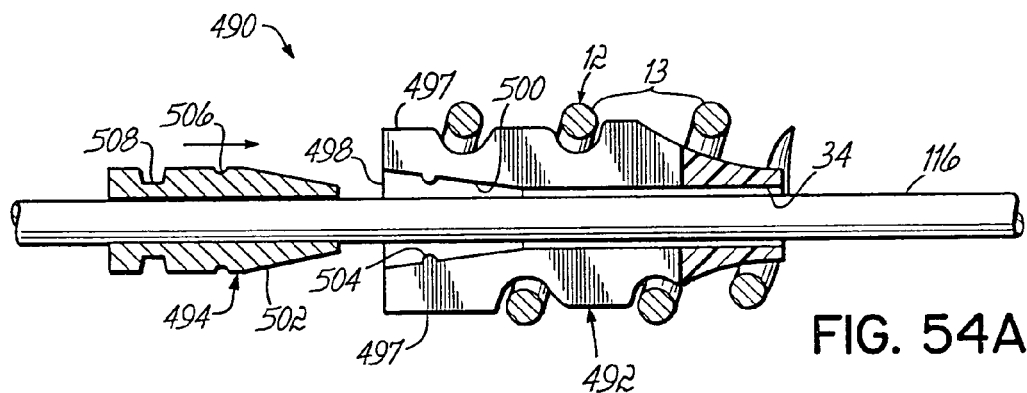
FIGS. 54A-54B are partial section views of the apparatus of FIG. 53, illustrating operation of the expandable retaining member.
Figure 54B:
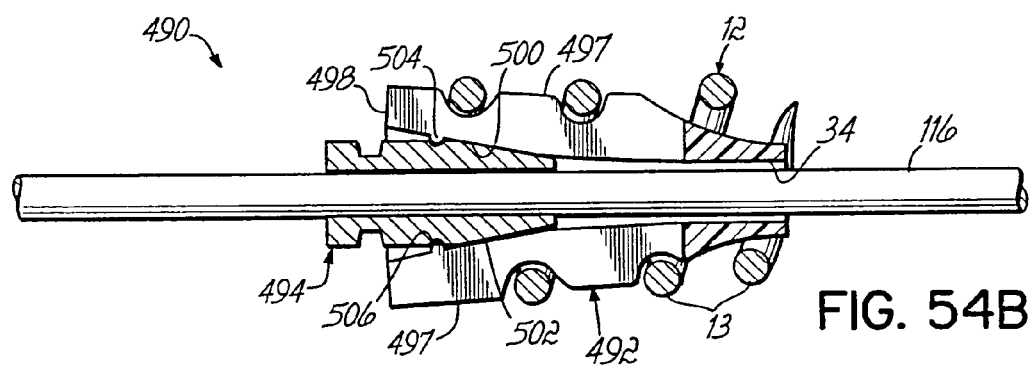

Aperture 498 has a tapered surface 500 which is configured to mate with a corresponding tapered surface 502 on the expansion member 494, whereby the expandable portions 497 may be driven outward by the interaction between the tapered surfaces 500, 502 when expansion member 494 is urged into engagement with retaining member 492 as depicted in FIG. 54B. In an exemplary embodiment, retaining member 492 further includes an annual detent disposed within aperture 498 and configured to engage a corresponding groove 506 formed into expansion member 494. Advantageously, the annular detent 504 engages the groove 506 on the expansion member 494 to secure the expansion member 494 to the retaining member 492 after expandable portions 497 have been expanded outwardly against the helical anchor 12.

Figure 55:
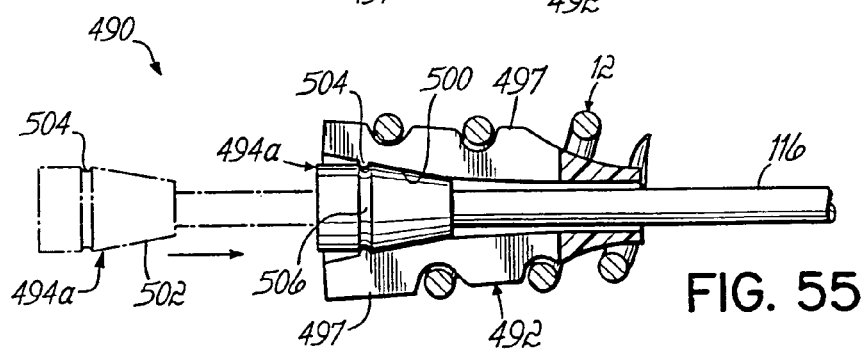
FIG. 55 is a partial section view of an alternative embodiment of the apparatus of FIG. 53.

Anchor assembly 490, including expansion member 494, may be secured to an elongate tensile member 116 using a stop member 60 in a manner such as previously described. Alternatively, the expansion member 494 may include a crimpable portion 508 that permits the anchor assembly 490 to be secured to an elongate tensile member 116, as depicted in FIGS. 54A and 54B. Alternatively, expansion member 494*a* may be provided pre-secured to an elongate tensile member 116 whereby the retaining member 492 may be expanded by applying tension to elongate tensile member 116 to urge expansion member 494*a* into engagement with expandable retaining member 492 to expand the expandable portions 497 as described above and as depicted in FIG. 55.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. An apparatus for repairing soft tissue, comprising:
   an elongate housing having a first end and a second end, said first end configured to receive a soft tissue anchor;
   a handle disposed proximate said second end of said housing;
   a tubular shaft disposed within said housing, said shaft rotatable within and movable along a longitudinal axis of said housing and having an inner bore extending lengthwise through at least a portion of said shaft;
   a driving member coupled with said shaft for rotation therewith and configured to engage the soft tissue anchor, whereby rotation of said shaft imparts rotation to the soft tissue anchor via said driving member;
   an inner member disposed within said shaft and movable along said inner bore independently of said shaft and the soft tissue anchor, said inner member having an inner channel sized to receive an elongate tensile member or a shuttle member;
   a first actuating member coupled to said shaft and configured to translate said shaft along said longitudinal axis of said housing when manipulated by a user; and
   a second actuating member coupled to said inner member and configured to move said inner member along said inner bore between an extended position wherein said inner member extends beyond said first end of said housing and a retracted position wherein said inner member is substantially within said housing.

2. The apparatus of claim 1, wherein said first and second actuating members are disposed proximate said second end of said housing, said apparatus further comprising a passage for receiving an elongate tensile member therethrough, said passage extending through said inner member, said handle, and said first and second actuating members.

3. The apparatus of claim 1, wherein said elongate tensile member is disposed within said inner member, and manipulation of said second actuating member extends said elongate tensile member and said inner member beyond said first end of said housing.

4. The apparatus of claim 3, further comprising a needle coupled proximate a distal end of said elongate tensile member, said inner member engageable with said needle to extend said elongate tensile member and said needle past said first end of said housing when said second actuating member is manipulated.

5. The apparatus of claim 1, further comprising a soft tissue anchor operatively coupled with said driving member.

6. An apparatus for repairing soft tissue, comprising:
   a tubular housing having a first end and a second end, said first end configured to receive a soft tissue anchor;
   a handle disposed proximate said second end of said housing;
   a shaft disposed and rotatable within said housing, said shaft movable along a longitudinal axis of said housing and configured to extend beyond said first end;
   a driving member coupled with said shaft for rotation therewith and having a distal end configured to engage the soft tissue anchor when the soft tissue anchor is installed within the first end of the housing, whereby rotation of said shaft imparts rotation to the soft tissue anchor via said driving member; and
   a first actuating member coupled to said shaft and configured to move said shaft along said longitudinal axis of said housing and rotate said shaft about said longitudinal axis.

7. An apparatus for repairing soft tissue, comprising:
   an elongate housing having a first end and a second end, said first end configured to receive a soft tissue anchor;
   a tubular shaft disposed within said housing, said shaft rotatable within and movable along a longitudinal axis of said housing and having an inner bore extending lengthwise through at least a portion of said shaft, whereby rotation of said shaft imparts rotation to the soft tissue anchor; and
   an inner member disposed within said shaft and movable along said inner bore independently of said shaft and the soft tissue anchor, said inner member having an inner channel sized to receive an elongate tensile member or a shuttle member.

8. The apparatus of claim 7, further comprising:
   a driving member coupled with said shaft for rotation therewith and configured to engage the soft tissue anchor.

9. The apparatus of claim 8, further comprising:
   a first actuating member coupled to said shaft and configured to translate said shaft along said longitudinal axis of said housing when manipulated by a user; and
   a second actuating member coupled to said inner member and configured to move said inner member between an extended position wherein said inner member extends beyond said first end of said housing and a retracted position wherein said inner member is further within said housing.

10. The apparatus of claim 9, wherein said elongate tensile member is disposed within said inner member, the apparatus further comprising:
    a needle coupled proximate a distal end of said elongate tensile member, said inner member engageable with said needle to extend said elongate tensile member and said needle past said first end of said housing when said second actuating member is manipulated.

11. An apparatus for repairing soft tissue, comprising:
    an elongate housing having a first end and a second end, said first end configured to receive a soft tissue anchor;
    a tubular shaft disposed within said housing, said shaft rotatable within and movable along a longitudinal axis of said housing and having an inner bore extending lengthwise through at least a portion of said shaft, whereby rotation of said shaft imparts rotation to the soft tissue anchor;
    an inner member disposed within said shaft and movable along said inner bore independently of said shaft and the soft tissue anchor;

a first actuating member coupled to said shaft and configured to move said shaft along said longitudinal axis of said housing and rotate said shaft about said longitudinal axis, said first actuating member being rotatable relative to said housing; and a second actuating member coupled to said inner member and configured to move said inner member along said inner bore and rotate said inner member within said inner bore, said second actuating member being rotatable relative to said housing.

12. The apparatus of claim 11, further comprising:
a driving member coupled with said shaft for rotation therewith and configured to engage the soft tissue anchor.

13. The apparatus of claim 11, wherein said inner member includes an inner channel sized to receive an elongate tensile member or a shuttle member.

14. The apparatus of claim 13, wherein said elongate tensile member is disposed within said inner member, and manipulation of said second actuating member extends said elongate tensile member and said inner member beyond said first end of said housing.

15. The apparatus of claim 14, further comprising a needle coupled proximate a distal end of said elongate tensile member, said inner member engageable with said needle to extend said elongate tensile member and said needle past said first end of said housing when said second actuating member is manipulated.

16. An apparatus for repairing soft tissue, comprising:
a tubular housing having a first end and a second end, said first end configured to receive a soft tissue anchor;
a shaft disposed within said housing, said shaft movable along a longitudinal axis of said housing;
a driving member coupled to said shaft for rotation therewith, said driving member having a projecting distal portion configured to engage the soft tissue anchor when the soft tissue anchor is installed within the first end of the housing and a proximal portion received over at least a portion of said shaft, whereby rotation of said shaft imparts rotation to the soft tissue anchor via said driving member; and
a first actuating member coupled to said shaft and configured to move said shaft along said longitudinal axis of said housing.

17. The apparatus of claim 16, further comprising a soft tissue anchor operatively coupled with said driving member.

18. The apparatus of claim 17, wherein said soft tissue anchor includes a distal end, a proximal end, and a recess defined in said proximal end, and wherein said projecting portion of said driving member is configured to be received within said recess.

19. The apparatus of claim 16, wherein said shaft is flexible.

* * * * *

UNITED STATES PATENT AND TRADEMARK OFFICE
CERTIFICATE OF CORRECTION

PATENT NO. : 7,611,521 B2
APPLICATION NO. : 10/816725
DATED : November 3, 2009
INVENTOR(S) : Lubbers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1376 days.

Signed and Sealed this

Twelfth Day of October, 2010

David J. Kappos
*Director of the United States Patent and Trademark Office*